United States Patent
Jiang et al.

(10) Patent No.: US 9,328,367 B2
(45) Date of Patent: May 3, 2016

(54) ENGINEERED LOWER EUKARYOTIC HOST STRAINS FOR RECOMBINANT PROTEIN EXPRESSION

(71) Applicant: MERCK SHARP & DOHME CORP., Rahway, NJ (US)

(72) Inventors: Bo Jiang, Norwich, VT (US); Rebecca D. Argyros, Hartford, VT (US); Stephanie Nelson, White River Junction, VT (US); Robert C. Davidson, Enfield, NH (US); Ronghua Chen, Needham Heights, MA (US); Jun Zhuang, Wellesley, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/354,628

(22) PCT Filed: Oct. 23, 2012

(86) PCT No.: PCT/US2012/061432
§ 371 (c)(1),
(2) Date: Apr. 28, 2014

(87) PCT Pub. No.: WO2013/062940
PCT Pub. Date: May 2, 2013

(65) Prior Publication Data
US 2014/0302557 A1    Oct. 9, 2014

Related U.S. Application Data

(60) Provisional application No. 61/552,674, filed on Oct. 28, 2011.

(51) Int. Cl.
*C12P 21/00* (2006.01)
*C12N 15/80* (2006.01)
*C07K 16/32* (2006.01)
*C07K 14/39* (2006.01)

(52) U.S. Cl.
CPC .............. *C12P 21/00* (2013.01); *C07K 14/39* (2013.01); *C07K 16/32* (2013.01); *C12N 15/80* (2013.01); *C12P 21/005* (2013.01); *C07K 2317/14* (2013.01)

(58) Field of Classification Search
None
See application file for complete search history.

(56) References Cited

U.S. PATENT DOCUMENTS

2006/0211085 A1 *    9/2006    Bobrowicz .................. 435/69.1

FOREIGN PATENT DOCUMENTS

WO    WO2013062940    5/2013

OTHER PUBLICATIONS

Krijger et al., A Novel Lactase based selection and strain improvement strategy for recombinant protein expression in Kluyveromyces lactis, Microb. Cell Fact., 2012, pp. 1-12, 11.
Kuberl et al., Pichia Pastoris CBS 7435 Chromosome 1 Complete replicon Sequence, GenBank Accession No. FR839628, 2011, relevant pp. 1-3, 19-20, 21, 37, 38 and 39, None.
International Search Report—Mail date—Jan. 7, 2013.
Zachariae et al., Glucose repression of lactose/galactose metabolism inKluyv/eromyces lactis is determined by the concentration ofthe transcriptional activator LA1 9 (KiGAL4), Nucleic Acids Res., 1993, pp. 69-77, 21.

* cited by examiner

*Primary Examiner* — Nancy T Vogel
(74) *Attorney, Agent, or Firm* — Gloria Fuentes; Immac Thampoe

(57) ABSTRACT

The present invention relates to novel engineered lower eukaryotic host cells for expressing heterologous proteins and to methods of generating such strains.

9 Claims, 47 Drawing Sheets

```
                1                                                    50
PpATT1     (1)  MHHKERLIDHISSESNFSLSTSSMPSFSHESNQSPNPMLIEQACDSCRKR
ScGAL4     (1)  ----------------------------------MKLLSSIEQACDICRLK
                51                                                  100
PpATT1    (51)  KLRCSKEYPKCSKQVTHKNSCVYSPRTVRSPLTRAHLTKVENRVRMLEDL
ScGAL4    (18)  KLKCSKEKPKCAKCLKNNWECRYSPKTKRSPLTRAHLTEVESRLERLEQL 101                                                 150
PpATT1   (101)  LERVFPTQSVDQLLEKRTSLSGNSTGHSPSYPNSNSVSPQNSSPKVSDSS
ScGAL4    (68)  FLLIFPREDLDMILKMDSLQDIKALLTGLFVQDN------------VNKD 151                                                 200
PpATT1   (151)  STTAEPAPVLPSKPKSSFRPIVPDDYFLNDEINGFDWEEEDTPDQLLVMQ
ScGAL4   (106)  AVIDRLASVETDMP--------------------------------LTLR
                201                                                 250
PpATT1   (201)  QPPTSVDSTNVSHSYWNHSRRSQKNSVTSLNSLAEHEQSGCSSLITSPSL
ScGAL4   (124)  QHRISATSSSEES-----SNKGQRQLTVSIDSAAHHDNSTIPLDFMPRDA
                251                                                 300
PpATT1   (251)  QPLSQTTTNDSHPDGMAALSVNLKGGSCYFCFSSSSGLLRALKLGQFDSA
ScGAL4   (169)  LHGFDWSEEDDMSDGLPFLKTDPNN-NCFFCDGSLLCILRSIGFK-----
                301                                                 350
PpATT1   (301)  SISPMSSVRNSVSKTNTEPTEPQSIRSLLGDPNDFLEPEKKAEFPGYDSH
ScGAL4   (213)  ---PENYTNSNVNRLPTMITDR------------------------YT
                351                                                 400
PpATT1   (351)  LNDPNNQSQYLQAYFKYYITSYPFILKGSFLKHYAGELPIKNENHWQILL
ScGAL4   (234)  LASRSTTSRLLQSYLNNFHPYCPIVHSPTLMMLYNNQIEIASKDQWQILF
                401                                                 450
PpATT1   (401)  NVVLALGCWCLNGESSSIDLCYYNRAKMLLKQVGIFECGNIMLLESLIIL
ScGAL4   (284)  NCILAIGAWCIEGESTDIDVFYYQNAKSHLTSK-VFESGSIILVTALHLL
                451                                                 500
PpATT1   (451)  SNYTQKRNKPNTGWSYLGIAIRMAMSLGLYKEFNLDHTEKDHYLNLEIRR
ScGAL4   (333)  SRYTQWRQKTNTSYNFHSFSIRMAISLGLNRDLPSSFSDSS---ILEQRR
                501                                                 550
PpATT1   (501)  RLWWGLYIFDAGASITFGRPITLPSRDSCDIQLCSNINDAELEELIEIKS
ScGAL4   (380)  RIWWSVYSWEIQLSLLYGR------------------SIQLSQNTISFP
```

FIG.1A

```
           551                                            600
PpATT1  (551) DSITTEDLNKPYPTAYSGLIQQTQFTELSMKIYNRLVSKPAP----TVEE
ScGAL4  (411) SSVDDVQRTTTGPTIYHGIIETARLLQVFTKIYELDKTVTAEKSPICAKK
           601                                            650
PpATT1  (597) CLDMNMEIENFIKGLPAYFHESNEIAMSQFYKVTPSKYYDYDSNKQVDYT
ScGAL4  (461) CLMICNETEEVSRQAPKFLQ-----------------MDISTTALTNLL
           651                                            700
PpATT1  (647) RLPQWFDLSRSRLIWRYKNLQITLFRAFIWQRVIGVTNPKVLQQCKTS-R
ScGAL4  (493) KEHPWLSFTRFELKWKQLSLIIYVLRDFFTNFTQKKSQLEQDQNDHQSYE
           701                                            750
PpATT1  (696) GKECRTICLRVAHETILSIQQFVNIDDDDDFSRLSVIGQWYATYFLFQAV
ScGAL4  (543) VKRCSIMLSDAAQRTVMSVSSYMDNHN------VTPYFAWNCSYYLFNAV
           751                                            800
PpATT1  (746) LIPTACLCSEPDSKYAP-IWIEDIQISKKIFLKLNKLN----SLASKFAN
ScGAL4  (587) LVPIKTLLSNSKSNAENNETAQLLQQINTVLMLKKLATFKIQTCEKYIQ
           801                                            850
PpATT1  (791) VIDRSMSQVMPQFDTTSAKDSPLNINDLIDMHGLMGNS-------P-APG
ScGAL4  (637) VLEEVCAPFLLSQCAIPLPHISYNNSNGSAIKNIVGSATIAQYPTLPEEN
           851                                            900
PpATT1  (833) SNNNSNTKSSPSTTNNTRTPNTINKNNSNMNNNSINNYFNNNS-----NN
ScGAL4  (687) VNNISVKYVSPGSVGPSPVPLKSGASFSDLVKLLSNRPPSRNSPVTIPRS
           901                                            950
PpATT1  (878) NNSFSSSKAGPVKQEFEDYCLKLDP--------------EDEDMSALEF
ScGAL4  (737) TPSHRSVTPFLGQQQQLQSLVPLTPSALFGGANFNQSGNIADSSLSFTFT
           951                                           1000
PpATT1  (913) TAVRFPNFSATTTAPPPTPVNCNSPENIKTSTVDDFLKATQDP-NNKEIL
ScGAL4  (787) NSSNGPNLITTQTNSQALSQPIASSNVHDNFMNNEITASKIDDGNNSKPL
          1001                                           1045
PpATT1  (962) NDIYSLIFDDSMDPMSFGSMEPRNDLEVPDTIMD----------
ScGAL4  (837) SPGWTDQTAYNAFGITTGMFNTTTMDDVYNYLFDDEDTPPNPKKE
```

FIG.1B

PpATT1 Deletion of Truncations Led
to Increased Thermal Tolerance

PpATT1 Deletion of Truncations Led
to Increased Thermal Tolerance

PpATT1 Deletion of Truncations Led
to Increased Thermal Tolerance

| A | YGLY17172 | PpATT1 UV derived mutant |
|---|---|---|
| B | YGLY1708 | WT PpATT1 control (temperature-sensitive) |
| C | YGLY27611 | ATT1 complete deletion |
| D | YGLY27601 | ATT1 (1-107aa + 5bp insertion at 31aa) |
| E | YGLY27602 | ATT1 (1-164aa + 5bp insertion at 31aa) |
| F | YGLY27603 | ATT1 (1-655aa + 5bp insertion at 31aa) |
| G | YGLY27606 | ATT1 (1-107aa) fragment |
| H | YGLY27608 | ATT1 (1-164aa) fragment |
| I | YGLY27610 | ATT1 (1-655aa) fragment |

FIG.6C

| Run | Strain | M24 clone | Description | ind time (h) | Lysis | PicoGreen | HPLC Titer |
|---|---|---|---|---|---|---|---|
| D113325 | YGLY27927 | M1130-06 A1 | YGLY13979 + AOX1-ATT1 | 111 | 2.5 | 23 | 707 |
| D113326 | YGLY27928 | M1130-06 A2 | YGLY13979 + AOX1-ATT1 | 64 | 4.25 | 28 | 605 |
| D113327 | YGLY27929 | M1130-06 A3 | YGLY13979 + AOX1-ATT1 | 112 | 1.25 | 4.5 | 1974 |
| D113328 | YGLY27930 | M1130-06 A4 | YGLY13979 + AOX1-ATT1 | 113 | 1 | 5.2 | 1960 |
| D113329 | YGLY27931 | M1130-06 A5 | YGLY13979 + AOX1-ATT1 | 67 | 3.5 | 7.4 | 648 |
| D113330 | YGLY27932 | M1130-06 A6 | YGLY13979 + AOX1-ATT1 | 66 | 4.25 | 38.9 | 837 |
| D113331 | YGLY13979 | N/A | YGLY13979 | 66 | 4.25 | 26 | 671 |
| D113332 | YGLY27638 | N/A | YGLY13979 att1::URA5 | 106 | 0.75 | 1.2 | 1256 |

FIG.17

PpATT1 Homologous to Saccharomyces Transcription
Factor GAL4 and H. polymorpha ATT1-like

```
                1                                                                                                   100
HpATT1 aa    (1) MEGISKPVGFGENKESMVKRELSDEDLFVLESRLSESASSANLTNSPSPPQNSNLSNGHSTKPTISRTTSSGSSYVHRQHTPSHGSRHLAHHHHNNSV
PpATT1 aa    (1) ------------------------------------------------------------------------------------------MHHKERL
ScGAL4 aa    (1) ----------------------------------------------------------------------------------------------------
Consensus    (1)                                                                                           MHHKERL 101                                                                                                   200
HpATT1 aa  (101) FPQRTIKREPSDSLEDDAIEEAEGYEMKSHSRNKPLIEQACDSCRRKLRCTKELPKCSKQMDHQMECVYSPRAVRSPLTRAMITKVENRVMKQLETFLLK
PpATT1 aa    (8) IDHISS--ESNFSLSTSSMPSFSHESNQSP--NPMLIEQACDSCRKRKLRCSKEYPKCSKCVTHKWSCVYSPRTVRSPLTRAHLTKVENRVRMLEDLLER
ScGAL4 aa    (1) ----------------MKLLSSIEQACDICRLKKLKCSKEKPKCAKCLKNNWECRYSPKTKRSPLTRAHLTEVESRLERLEQLFLL
Consensus  (101) IDHISS   ESNFSLSTSSMPSFSHESNQSP   NPMLIEQACDSCRKRKLRCSKEYPKCSKCVTHKWSCVYSPRTVRSPLTRAHLTKVENRVMLEDLLER 201                                                                                                   300
HpATT1 aa  (201) AFPGEDLEQMLGGFSRTGSSIQSLCNSPNMSAYSLLSQNKQHCDNTSSTQTMQDFSLDASSTSIFKKETPQQILSRLPDEFMATDLSNNTNFDWSEDDEE
PpATT1 aa  (104) VFPTQSVDQLL----EKRTSLSGNSTGHSPSYPNSNSVSPQN---------SSPKVSDSSSTTAEPAPVLPSKPKSSFRPIVPDDYFLNDEIN--GFDWEEEDTP
ScGAL4 aa   (71) IFPREDLDMILKMDSLQDIKALLTG---------------------------------------------------------LFVQDNVN---KDAVT
Consensus  (201) VFPTQSVDQLL    EKRTSLSGNSTGHSPSYPNSNSVSPQN         SSPKVSDSSSTTAEPAPVLPSKPKSSFRPIVPDDYFLNDEIN  GFDWEEEDTP 301                                                                                                   400
HpATT1 aa  (301) REKGLMANGSPSSPSSITSLHEPKNSVISFNSLDHLHTSQAQSSTISTKTNNSSLCTSPMLRAVAPSFSTDGMGVNPTTKSGFILGVGSSSSFLRVMKIDK
PpATT1 aa  (194) DQLLVMQQ--P---PTSVDSTNVSHSYWNHSRRSQKNSVTSLNSLAEHEQSGCSSLITSPSLQPLSQTTTNDSHPDGMAALSVNLKGGSG-------
ScGAL4 aa  (109) DRLASVETDMP---LITLRQHRISATSSSEESSNKGQRQLITVSIDSAAHHDNSTIPLDFMPRDALHGFDWSEEDMSDGLPFLKTDPN--------
Consensus  (301) DQLLVMQQ  P    PTSVDSTNVSHSYWNHSRRSQKNSVTSLNSLAEHEQSGCSSLITSPSLQPLSQTTTNDSHPDGMAALSVNLKGGSG
```

ENGINEERED LOWER EUKARYOTIC HOST STRAINS FOR RECOMBINANT PROTEIN EXPRESSION

CROSS REFERENCE TO RELATED APPLICATIONS

This application is the National Stage of International Application No. PCT/US2012/61432 filed on Oct. 23, 2012, which claims the benefit under 35 U.S.C. 119(e) of U.S. Provisional Application No. 61/552,674, filed Oct. 28, 2011.

REFERENCE TO SEQUENCE LISTING SUBMITTED ELECTRONICALLY

The sequence listing of the present application is submitted electronically via EFS-Web as an ASCII formatted sequence listing with a file name "23132_US_PCT_SEQLIST.txt", creation date of 27 Mar., 2014, and a size of 253 KB. This sequence listing submitted via EFS-Web is part of the specification and is herein incorporated by reference in its entirety.

FIELD OF THE INVENTION

The present invention relates to novel engineered lower eukaryotic host cells for expressing heterologous proteins and to methods of generating such strains.

BACKGROUND OF THE INVENTION

Lower eukaryotic host cells can be engineered to produce heterologous proteins. Further, lower eukaryotic host cells can be glyco-engineered to produce glycoproteins where the N- or O-linked glycosylation are modified from their native forms.

Engineered *Pichia* strains have been utilized as an alternative host system for producing recombinant glycoproteins with human-like glycosylation. However, the extensive genetic modifications have also caused fundamental changes in cell wall structures in many glyco-engineered yeast strains, predisposing some of these strains to cell lysis and reduced cell robustness during fermentation. Certain glyco-engineered strains have substantial reductions in cell viability as well as a marked increase in intracellular protease leakage into the fermentation broth, resulting in a reduction in both recombinant product yield and quality.

Current strategies for identifying robust glyco-engineered production strains rely heavily on screening a large number of clones using various platforms such as 96-deep-well plates, 5 ml mini-scale fermenters and 1 L-scale bioreactors to empirically identify clones that are compatible for large-scale (40 L and above) fermentation processes (Barnard et al. 2010). Despite the fact that high-throughput screening has been successfully used to identify several *Pichia* hosts capable of producing recombinant monoclonal antibodies with yields in excess of 1 g/L (Potgieter et al. 2009; Zhang et al. 2011), these large-scale screening approach is very resource-intensive and time-consuming, and often only identify clones with incremental increases in cell-robustness.

Therefore, lower eukaryotic host strains that have improved robustness and the ability to produce high quality proteins with human-like glycans would be of value and interest to the field. Here, we present engineered *Pichia* host strains having a deletion, truncation or nonsense mutation in a novel gene ATT1 (acquiring thermal tolerance) which under relevant bioprocess conditions exhibit improved viability, stability, and protein production. Surprisingly, engineered *Pichia* host strains over-expressing ATT1 or fragments thereof under relevant bioprocess conditions also exhibit improved viability, stability, and protein production. These strains are especially useful for heterologous gene expression.

SUMMARY OF THE INVENTION

The invention relates to engineered lower eukaryotic host cells that have been modified to reduce or eliminate the activity of the ATT1 gene. The activity of the ATT1 gene can be reduced by any means. In one embodiment, the activity of the ATT1 gene is reduced or eliminated by reducing or eliminating the expression of the ATT1 gene (for example by using interfering RNA or antisense RNA). In another embodiment, the activity of the ATT1 gene is reduced or eliminated by mutating the ATT1 gene or its product. In another embodiment, the activity of the ATT1 gene is reduced or eliminated by degrading the ATT1 polypeptide. In another embodiment, the activity of the ATT1 gene is reduced or eliminated by using an inhibitor of ATT1, for example a small molecule inhibitor or an antibody inhibitor. The invention encompasses any means of inactivating the ATT1 gene or its protein including transcriptionally, translationally, or post-translationally means (for example, using repressible promoter, interfering RNA, antisense RNA, inducible protein degradation, and the like). In one embodiment, the lower eukaryotic cell is a glyco-engineered lower eukaryotic host cells. In one embodiment, the lower eukaryotic cell is a lower eukaryotic host cell that lacks OCH1 activity. In one embodiment, the lower eukaryotic host cell is a fungal host cell. In one embodiment, the lower eukaryotic cell is a fungal host cell that lacks OCH1 activity. In one embodiment, the lower eukaryotic host cell is a yeast host cell. In one embodiment, the lower eukaryotic cell is a yeast host cell that lacks OCH1 activity. In one embodiment, the lower eukaryotic host cell is a *Pichia* sp. In one embodiment, the lower eukaryotic cell is a *Pichia* sp. host cell that lacks OCH1 activity. In another embodiment, the host cell is *Pichia pastoris* and the ATT1 gene encodes a polypeptide comprising the amino acid of SEQ ID NO:7 or a polymorph thereof. In another embodiment, the host cell is *Hansenula polymorpha* and the ATT1 gene encodes a polypeptide comprising the amino acid sequence of SEQ ID NO:23 or a polymorph thereof.

In other embodiments, the present invention relates to an engineered lower eukaryotic host cell that has been modified to express a mutated form of the ATT1 gene. The mutation could be a single nucleotide mutation, a frame-shift mutation, an insertion, a truncation or a deletion of one or more nucleotides. In one embodiment, said mutation is a deletion of the entire ATT1 gene. In another embodiment, said mutation is a deletion of a fragment of the ATT1 gene. In one embodiment, the lower eukaryotic cell is a glyco-engineered lower eukaryotic host cell. In one embodiment, the lower eukaryotic cell is a lower eukaryotic host cell that lacks OCH1 activity. In one embodiment, the lower eukaryotic host cell is a fungal host cell. In one embodiment, the lower eukaryotic cell is a fungal host cell that lacks OCH1 activity. In one embodiment, the lower eukaryotic host cell is a yeast host cell. In one embodiment, the lower eukaryotic cell is a yeast host cell that lacks OCH1 activity. In one embodiment, the lower eukaryotic host cell is a *Pichia* sp. In one embodiment, the lower eukaryotic cell is a *Pichia* sp. host cell that lacks OCH1 activity. In another embodiment, the host cell is *Pichia pastoris* and the ATT1 gene encodes a polypeptide comprising the amino acid of SEQ ID NO:7 or a polymorph thereof. In one embodiment, said mutated form of the ATT1 gene is a deletion of a fragment comprising amino acids 32-995 of SEQ ID NO:7. In one embodiment, said mutated form of the ATT1 gene is a deletion of fragment comprising amino acids 165-995 of SEQ ID NO:7. In another embodiment, said mutated form of the ATT1 gene is a deletion of fragment comprising amino acids 277-995 of SEQ ID NO:7. In another embodiment, said mutated form of the ATT1 gene is a deletion of fragment comprising amino acids 540-995 of SEQ ID NO:7. In another embodiment, said mutated form of the ATT1 gene is a deletion of fragment comprising amino acids 729-995 of SEQ ID NO:7. In another embodiment, said mutated form of the ATT1 gene is an insertion or a frameshift mutation in the nucleic acid encoding SEQ ID NO:7. In another embodiment, said mutated form of the ATT1 gene is a single nucleotide mutation in the nucleic acid sequence encoding SEQ ID NO:7. In another embodiment, said mutated form of the ATT1 gene results in a single amino acid change in SEQ ID NO:7. In another embodiment, the host cell is *Hansenula polymorpha* and the ATT1 gene encodes a polypeptide comprising the amino acid sequence of SEQ ID NO:23 or a polymorph thereof.

In some embodiments, the engineered lower eukaryotic host cell of the invention exhibits an increase in culture stability, thermal tolerance and/or improved fermentation robustness compared with an ATT1 naïve parental host cell under similar culture conditions. In one embodiment, said engineered host cell is capable of surviving in culture at 32° C. for at least 80 hours of fermentation with minimal cell lysis. In one embodiment, said engineered host cell is capable of surviving in culture at 32° C. for at least 80 hours of fermentation after induction (for example, methanol induction) with minimal cell lysis. In one embodiment, said engineered host cell is capable of surviving in culture at 32° C. for at least 100 hours of fermentation with minimal cell lysis. In one embodiment, said engineered host cell is capable of surviving in culture at 32° C. for at least 100 hours of fermentation after induction with minimal cell lysis.

In some embodiments, the engineered lower eukaryotic host cell of the invention further comprises a mutation, disruption or deletion of one or more of functional gene products. In one embodiment, the host cell comprises a mutation, disruption or deletion of one or more genes encoding: protease activities, alpha-1,6-mannosyltransferase activities, alpha-1,2-mannosyltransferase activities, mannosylphosphate transferase activities, β-mannosyltransferase activities, O-mannosyltransferase (PMT) activities, and/or dolichol-P-Man dependent alpha(1-3) mannosyltransferase activities. In one embodiment, the host cell comprises a mutation, disruption or deletion in the OCH1 gene. In one embodiment, the host cell comprises a mutation, disruption or deletion in the BMT1, BMT2, BMT3, and BMT4 genes. In one embodiment, the host cell comprises a mutation, disruption or deletion in the PNO1, MNN4, and MNN4L1 genes. In one embodiment, the host cell comprises a mutation, disruption or deletion in the PEP4 and PRB1 genes. In another embodiment, the host cell comprises a mutation, disruption or deletion of the ALG3 gene (as described in US Patent Publication No. US2005/0170452). In one embodiment, the host cell further comprises a mutation, disruption or deletion of all of the following genes: OCH1, BMT1, BMT2, BMT3, BMT4, PNO1, MNN4, and MNN4L1. In one embodiment, the host cell further comprises a mutation, disruption or deletion of all of the following genes: OCH1, BMT1, BMT2, BMT3, BMT4, PNO1, MNN4, MNN4L1, PEP4 and PRB1. In one embodiment, the host cell further comprises a mutation, disruption or deletion of all of the following genes: OCH1, BMT1, BMT2, BMT3, BMT4, PNO1, MNN4, MNN4L1, ALG3, PEP4 and PRB1. In one embodiment, the engineered lower eukaryotic host cell of the invention further comprises a mutation, disruption or deletion of a gene selected from the group consisting of: SSK2, RRT12, SDS23, NOT5, DRS1, CRZ1, CTK1, RGD2, AVO2, YMR196W, PEX1, TYW1, POM152, YPR84W, MAK5, AZF1.

In yet additional embodiments, the engineered lower eukaryotic host cell of the invention further comprises one or more nucleic acid sequences of interest. In certain embodiments, the nucleic acid sequences of interest encode one or more glycosylation enzymes. In certain embodiments, the glycosylation enzymes are selected from the group consisting of glycosidases, mannosidases, phosphomannosidases, phosphatases, nucleotide sugar transporters, nucleotide sugar epimerases, mannosyltransferases, N-acetylglucosaminyltransferases, CMP-sialic acid synthases, N-acetylneuraminate-9-phosphate synthases, galactosyltransferases, sialyltransferases, and oligosaccharyltransferases. In yet additional embodiments, the engineered lower eukaryotic host cell of the invention further comprises a nucleic acid sequences encoding one or more recombinant proteins. In one embodiment, the recombinant protein is a therapeutic protein. The therapeutic protein can contain or lack oligosaccharides. In certain embodiments, the therapeutic proteins are selected from the group consisting of antibodies (IgA, IgG, IgM or IgE), antibody fragments, kringle domains of the human plasminogen, erythropoietin, cytokines, coagulation factors, soluble IgE receptor α-chain, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II, α-feto proteins, insulin, Fe-fusions, HSA-fusions, viral antigens and bacterial antigens. In one embodiment, the therapeutic protein is an antibody or a fragment thereof. In one embodiment, the therapeutic protein is an antibody or antibody fragment (Fe-containing polypeptide) comprising N-glycans. In one embodiment, the N-glycans comprise predominantly $NANA_{(1-4)}Gal_{(1-4)}Man_3GlcNAc_2$. In one embodiment, the N-glycans comprise predominantly $NANA_2Gal_2Man_3GlcNAc_2$.

The present invention further provides an engineered lower eukaryotic host cell comprising a disruption, deletion or mutation of the ATT1 gene in the genomic DNA, and further comprising a nucleic acid encoding an ATT1 polypeptide or a fragment thereof. In one embodiment, the lower eukaryotic cell is glyco-engineered. In one embodiment, the lower eukaryotic cell lacks OCH1 activity. In one embodiment, the lower eukaryotic host cell is a fungal host cell. In one embodiment, the lower eukaryotic cell is a fungal host cell that lacks OCH1 activity. In one embodiment, the lower eukaryotic host cell is a yeast host cell. In one embodiment, the lower eukaryotic cell is a yeast host cell that lacks OCH1 activity. In one embodiment, the lower eukaryotic host cell is a *Pichia* sp. In one embodiment, the lower eukaryotic cell is a *Pichia* sp. host cell that lacks OCH1 activity. In one embodiment, the fragment is a "functional fragment" of ATT1 or a "dominant-negative fragment" of ATT1. As used herein, a "functional fragment" of an ATT1 gene or polypeptide, refers to a fragment that has ATT1 activity. A "dominant-negative fragment" of an ATT1 gene or polypeptide, refers to a fragment that negatively interferes with the function of the intact ATT1 gene or its polypeptide product, so that even in the presence of the endogenous naïve ATT1 gene, such a fragment is capable of increasing the cell culture stability, thermal tolerance and/or improved fermentation robustness of a host cell (for example, fragments 1-31 aa and 1-164aa, in Example 11). In one embodiment, host cell is *Pichia pastoris* and the ATT1 polypeptide comprises the amino acid sequence of SEQ ID NO:7 or a polymorph thereof. In one embodiment, the host cell is *Pichia pastoris* and the functional fragment comprises or consists of amino acids 1-296 of SEQ ID NO:7. In one embodiment, the host cell is *Pichia pastoris* and the dominant-negative fragment comprises or consists of amino acids 1-31 of SEQ ID NO:7. In one embodiment, the host cell is *Pichia pastoris* and the dominant-negative fragment comprises or consists of amino acids 1-164 of SEQ ID NO:7. In one embodiment, the host cell is *H. polymorpha* and the ATT1 polypeptide comprises the amino acid sequence of SEQ ID NO:23 or a polymorph thereof. In some embodiments, the engineered host cell comprises an over-expression cassette comprising a nucleic acid sequence encoding SEQ ID NO:7 or a natural variant (polymorph) of said polypeptide.

The invention also relates to an engineered lower eukaryotic host cell, wherein the host cell has been modified to increase expression of a nucleic acid sequence encoding an ATT1 polypeptide or a fragment thereof. In one embodiment, the lower eukaryotic host cell is glyco-engineered. In one embodiment, the lower eukaryotic cell lacks OCH1 activity. In one embodiment, the lower eukaryotic host cell is a fungal host cell. In one embodiment, the lower eukaryotic cell is a fungal host cell that lacks OCH1 activity. In one embodiment, the lower eukaryotic host cell is a yeast host cell. In one embodiment, the lower eukaryotic cell is a yeast host cell that lacks OCH1 activity. In one embodiment, the lower eukaryotic host cell is a *Pichia* sp. In one embodiment, the lower eukaryotic cell is a *Pichia* sp. host cell that lacks OCH1 activity. In one embodiment, host cell is *Pichia pastoris* and the ATT1 polypeptide comprises the amino acid sequence of SEQ ID NO:7 or a polymorph thereof. In one embodiment, the host cell is *Pichia pastoris* and the functional fragment comprises or consists of amino acids 1-296 of SEQ ID NO:7. In one embodiment, the host cell is *Pichia pastoris* and the dominant-negative fragment comprises or consists of amino acids 1-31 of SEQ BD NO:7. In one embodiment, the host cell is *Pichia pastoris* and the dominant-negative fragment comprises or consists of amino acids 1-164 of SEQ ID NO:7. In one embodiment, the host cell is *H. polymorpha* and the ATT1 polypeptide comprises the amino acid sequence of SEQ ID NO:23 or a polymorph thereof. In some embodiments, the engineered host cell comprises an over-expression cassette comprising a nucleic acid sequence encoding SEQ ID NO:7 or a natural variant (polymorph) of said polypeptide.

In certain embodiments, the engineered lower eukaryotic host cell of the invention, which has been modified to increase expression of ATT1 or a fragment thereof, further comprises a mutation, disruption or deletion of one or more functional gene products. In one embodiment, the host cell comprises a mutation, disruption or deletion of one or more genes encoding protease activities, alpha-1,6-mannosyltransferase activities, alpha-1,2-mannosyltransferase activities, marmosylphosphate transferase activities, β-mannosyltransferase activities, O-mannosyltransferase (PMT) activities, and/or dolichol-P-Man dependent alpha(1-3) mannosyltransferase activities. In one embodiment, the host cell comprises a mutation, disruption or deletion in the OCH1 gene. In one embodiment, the host cell comprises a mutation, disruption or deletion in the BMT1, BMT2, BMT3, and BMT4 genes. In one embodiment, the host cell comprises a mutation, disruption or deletion in the PNO1, MNN4, and MNN4L1 genes. In one embodiment, the host cell comprises a mutation, disruption or deletion in the PEP4 and PRB1 genes. In another embodiment, the host cell comprises a mutation, disruption or deletion of the ALG3 gene (as described in US Patent Publication No. US2005/0170452). In one embodiment, the host cell further comprises a mutation, disruption or deletion of all of the following genes: OCH1, BMT1, BMT2, BMT3, BMT4, PNO1, MNN4, and MNN4L1. In one embodiment, the host cell further comprises a mutation, disruption or deletion of all of the following genes: OCH1, BMT1, BMT2, BMT3, BMT4, PNO1, MNN4, MNN4L1, PEP4 and PRB1. In one embodiment, the host cell further comprises a mutation, disruption or deletion of all of the following genes: OCH1, BMT1, BMT2, BMT3, BMT4, PNO1, MNN4, MNN4L1, ALG3, PEP4 and PRB1. In one embodiment, the engineered lower eukaryotic host cell of the invention further comprises a mutation, disruption or deletion of a gene selected from the group consisting of: SSK2, RRT12, SDS23, NOT5, DRS1, CRZ1, CTK1, RGD2, AVO2, YMR196W, PEX1, TYW1, POM152, YPR84W, MAK5, AZF1. In yet additional embodiments, the engineered lower eukaryotic host cell of the invention, which has been modified to increase expression of ATT1 or a fragment thereof, further comprises one or more nucleic acid sequences of interest. In certain embodiments, the nucleic acid sequences of interest encode one or more glycosylation enzymes. In yet additional embodiments, the glycosylation enzymes are selected from the group consisting of glycosidases, mannosidases, phosphomannosidases, phosphatases, nucleotide sugar transporters, mannosyltransferases, N-acetylglucosaminyltransferases, UDP-N-acetylglucosamine transporters, galactosyltransferases, sialyltransferases, and oligosaccharyltransferases.

In yet additional embodiments, the nucleic acid sequences of interest encode one or more recombinant proteins. In one embodiment, the recombinant protein is a therapeutic protein. In certain embodiments, the therapeutic protein is selected from the group consisting of antibodies (IgA, IgG, IgM or IgE), antibody fragments, kringle domains of the human plasminogen, erythropoietin, cytokines, coagulation factors, soluble IgE receptor α-chain, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II, α-feto proteins, insulin, Fe-fusions, HSA-fusions, viral antigens and bacterial antigens. In one embodiment, the therapeutic protein is an antibody or a fragment thereof. In one embodiment, the therapeutic protein is an antibody or antibody fragment (Fc-containing polypeptide) comprising N-glycans. In one embodiment, the N-glycans comprise predominantly $NANA_{(1-4)}Gal_{(1-4)}Man_3GlcNAc_2$. In one embodiment, the N-glycans comprise predominantly $NANA_2Gal_2Man_3GlcNAc_2$.

In yet additional embodiments, the engineered lower eukaryotic host cell of the invention, which has been modified to increase expression of ATT1 or a fragment thereof, exhibits an increase in culture stability, thermal tolerance or improved fermentation robustness compared with the ATT1 naïve parental host cell under similar culture conditions. In one embodiment, said host cell is capable of surviving in culture at 32° C. for at least 80 hours of fermentation with minimal cell lysis. In one embodiment, said host cell is capable of surviving in culture at 32° C. for at least 80 hours of fermentation after induction (for example, methanol induction) with minimal cell lysis. In one embodiment, said host cell is capable of surviving in culture at 32° C. for at least 100 hours of fermentation with minimal cell lysis. In one embodiment, said host cell is capable of surviving in culture in at 32° C. for at least 100 hours of fermentation after induction with minimal cell lysis.

The invention also provides an engineered *H. polymorpha* host cell that has been modified to reduce or eliminate the activity of the ATT1 gene of SEQ ID NO:23. In one embodiment, the invention provides a *H. polymorpha* host cell that has been modified to reduce or eliminate expression of a nucleic acid encoding SEQ ID NO:23, a natural variant thereof or a fragment thereof. The invention also provides a *H. polymorpha* host cell which has been modified to express a mutated form of an ATT1 gene encoding SEQ ID NO:23.

The invention also provides an engineered *H. polymorpha* host cell, wherein the host cell has been modified to increase expression of a nucleic acid encoding SEQ ID NO:23, a natural variant thereof or a fragment thereof.

In certain embodiments, the invention also provides engineered lower eukaryotic host cells comprising a disruption, deletion or mutation (e.g., a single nucleotide mutation, insertion mutation, or deletion mutation) of a nucleic acid sequence selected from the group consisting of the coding sequence of the ATT1 gene, the promoter region of the ATT1 gene, the 3' un-translated region (UTR) of ATT1, a nucleic acid sequence that is a degenerate variant of the coding sequence of the *P. pastoris* ATT1 gene and related nucleic acid sequences and fragments, in which the host cells have an increase in culture stability, thermal tolerance or improved fermentation robustness compared to a host cell without the disruption, deletion or mutation.

The invention also relates to methods of using the engineered lower eukaryotic host cells of the invention for producing heterologous polypeptides and other metabolites. In one embodiment, the invention provides for methods for producing a heterologous polypeptide in any of the *Pichia* sp. host cells described above comprising culturing said host cell under conditions favorable to the expression of the heterologous polypeptide; and, optionally, isolating the heterologous polypeptide from the host cell.

The invention also comprises a method for producing a heterologous polypeptide in an engineered lower eukaryotic host cell, said method comprising: (a) introducing a polynucleotide encoding a heterologous polypeptide into an engineered host cell which has been modified to reduce or eliminate the activity of an ATT1 gene which is an ortholog to the *Pichia pastoris* ATT1 gene; (b) culturing said host cell under conditions favorable to the expression of the heterologous polypeptide; and, optionally, (c) isolating the heterologous polypeptide from the host cell. In one embodiment, the lower eukaryotic host cell is glyco-engineered. In one embodiment, the lower eukaryotic cell lacks OCH1 activity. In one embodiment, the lower eukaryotic host cell is a fungal host cell. In one embodiment, the lower eukaryotic cell is a fungal host cell that lacks OCH1 activity. In one embodiment, the lower eukaryotic host cell is a yeast host cell. In one embodiment, the lower eukaryotic cell is a yeast host cell that lacks OCH1 activity. In one embodiment, the lower eukaryotic host cell is a *Pichia* sp. In one embodiment, the lower eukaryotic cell is a *Pichia* sp. host cell that lacks OCH1 activity. In another embodiment, the host cell is *Pichia pastoris* and the ATT1 gene encodes a polypeptide comprising the amino acid of SEQ ID NO:7 or a polymorph thereof. In another embodiment, the host cell is *Hansenula polymorpha* and the ATT1 gene encodes a polypeptide comprising the amino acid sequence of SEQ ID NO:23 or a polymorph thereof.

The invention also comprises a method for producing a heterologous polypeptide in an engineered lower eukaryotic host cell, said method comprising: (a) introducing a polynucleotide encoding a heterologous polypeptide into an engineered host cell which has been modified to overexpress an ATT1 gene which is an ortholog of the *Pichia pastoris* ATT1 gene of SEQ ID NO:7; (b) culturing said host cell under conditions favorable to the expression of the heterologous polypeptide; and, optionally, (c) isolating the heterologous polypeptide from the host cell. In one embodiment, the heterologous polypeptide may be operably linked to a methanol inducible promoter, and the host cell is cultured under conditions favorable to expression of the heterologous polypeptide in the presence of methanol. In one embodiment, the lower eukaryotic host cell is glyco-engineered. In one embodiment, the lower eukaryotic cell is a lower eukaryotic host cell that lacks OCH1 activity. In one embodiment, the lower eukaryotic host cell is a fungal host cell. In one embodiment, the lower eukaryotic cell is a fungal host cell that lacks OCH1 activity. In one embodiment, the lower eukaryotic host cell is a yeast host cell. In one embodiment, the lower eukaryotic cell is a yeast host cell that lacks OCH1 activity. In one embodiment, the lower eukaryotic host cell is a *Pichia* sp. In one embodiment, the lower eukaryotic cell is a *Pichia* sp. host cell that lacks OCH1 activity. In another embodiment, the host cell is *Pichia pastoris* and the ATT1 gene encodes a polypeptide comprising the amino acid of SEQ ID NO:7 or a polymorph thereof. In another embodiment, the host cell is *Hansenula polymorpha* and the ATT1 gene encodes a polypeptide comprising the amino acid sequence of SEQ ID NO:23 or a polymorph thereof.

The invention also provides a method for producing a heterologous polypeptide in an engineered *H. polymorpha* host cells, said method comprising: (a) introducing a polynucleotide encoding a heterologous polypeptide into an engineered *H. polymorpha* host cell that has been modified to reduce or eliminate expression of a nucleic acid encoding SEQ ID NO:23, a natural variant thereof or a fragment thereof; (b) culturing said cell under conditions favorable to the expression of the heterologous polypeptide; and, optionally, (c) isolating the heterologous polypeptide from the host cell.

The invention also provides a method for producing a heterologous polypeptide in an engineered *H. polymorpha* host cells, said method comprising: (a) introducing a polynucleotide encoding a heterologous polypeptide into an engineered *H. polymorpha* host cell that has been modified to increase expression of a nucleic acid encoding SEQ ID NO:23, a natural variant thereof or a fragment thereof; (b) culturing said cell under conditions favorable to the expression of the heterologous polypeptide; and, optionally, (c) isolating the heterologous polypeptide from the host cell.

The invention also provides a method for making any of the host cells of the invention, comprising introducing a heterologous polynucleotide into the cell which homologously recombines with the endogenous ATT1 gene and partially or fully deletes the endogenous ATT1 gene or disrupts the endogenous ATT1 gene.

In addition, the invention provides methods for the genetic integration of a heterologous nucleic acid sequence into a host cell comprising a disruption, deletion or mutation of the ATT1 gene in the genomic DNA of the host cell. These methods comprise the step of introducing a sequence of interest into the host cell comprising a disrupted, deleted or mutated nucleic acid sequence derived from a sequence selected from the group consisting of the coding sequence of the *P. pastoris* ATT1 gene, a nucleic acid sequence that is a degenerate variant of the coding sequence of the *P. pastoris* ATT1 gene and related nucleic acid sequences and fragments.

The invention also provides isolated polynucleotides encoding the *P. pastoris* ATT1 gene, or a fragment of the *P. pastoris* ATT1 gene, or an ortholog or polymorph (natural variant) of the *P. pastoris* ATT1 gene. The invention also provides isolated polynucleotides encoding mutants of the ATT1 gene (single nucleotide mutations, frame-shift mutations, insertions, truncations or deletions). The invention also provides vectors and host cells comprising these isolated polynucleotides or fragments of these polynucleotides. The invention further provides isolated polypeptides comprising or consisting of the polypeptide sequence encoded by the *P. pastoris* ATT1 gene, by a fragment of the *P. pastoris* ATT1 gene, or an ortholog or polymorph of the *P. pastoris* ATT1 gene. Antibodies that specifically bind to the isolated polypeptides of the invention are also encompassed herein.

In one embodiment, the invention comprises an expression vector comprising a nucleic acid encoding a wild-type or mutated ATT1 gene selected from the group consisting of: a nucleotide sequence encoding SEQ ID NO:7 or a fragment thereof; a nucleotide sequence encoding SEQ ID NO:8 or a fragment thereof; a nucleotide sequence encoding SEQ ID NO:9 or a fragment thereof; a nucleotide sequence encoding SEQ ID NO:10 or a fragment thereof; and a nucleotide sequence encoding SEQ ID NO:23 or a fragment thereof. In one embodiment, the isolated nucleic acid encodes a polypeptide comprising or consisting essentially of residues 1-296, 1-31 or 1-164 of SEQ ID NO:7. In one embodiment, the invention comprises an expression vector comprising a nucleic acid encoding a wild-type or mutated ATT1 gene selected from the group consisting of: SEQ ID NO:24 or a fragment thereof, SEQ ID NO:25 or a fragment thereof, SEQ ID NO:26 or a fragment thereof, SEQ ID NO:27 or a fragment thereof, SEQ ID NO:28 or a or a fragment thereof, SEQ ID NO:29 or a fragment thereof, SEQ ID NO:30 or a fragment thereof, SEQ ID NO:31 or a fragment thereof, and SEQ ID NO:32 or a fragment thereof. In one embodiment, an isolated host cell expressing said nucleic acid exhibits an increase in culture stability, thermal tolerance and/or improved fermentation robustness compared to an ATT1 naive parental host cell under similar conditions. The invention also comprises vectors and host cells comprising the nucleic acids of the invention, and the polypeptides encoded by these nucleic acids.

BRIEF DESCRIPTION OF THE DRAWINGS

FIGS. 1A-B shows a sequence alignment between *Saccharomyces cerevisiae* GAL4 SSEQ ID NO:32) and *Pichia pastoris* ATT1 SSEQ ID NO:1) amino acid sequences.

FIGS. 6A-C show photographs (FIG. 6A-B) and correlating table (FIG. 6C) illustrating improved growth of *Pichia pastoris* ATT1 mutants compared with growth of control host cells.

FIGS. 14E-H show plasmid maps of pGLY9960-pGLY9963, respectively.

FIG. 17 shows a table indicating induction time, strain lysis, and protein titer for various ATT1 engineered *Pichia* host strains.

FIG. 18 shows an alignment of *S. cerevisiae* Gal4 (SEQ ID NO:32), *P. pastoris* ATT1 (SEQ ID NO:1), *H. polymorpha* ATT1 (SEQ ID NO:23) and consensus ATT1 sequence (SEQ ID NO:33).

DETAILED DESCRIPTION OF THE INVENTION

Molecular Biology

Figure 2A:
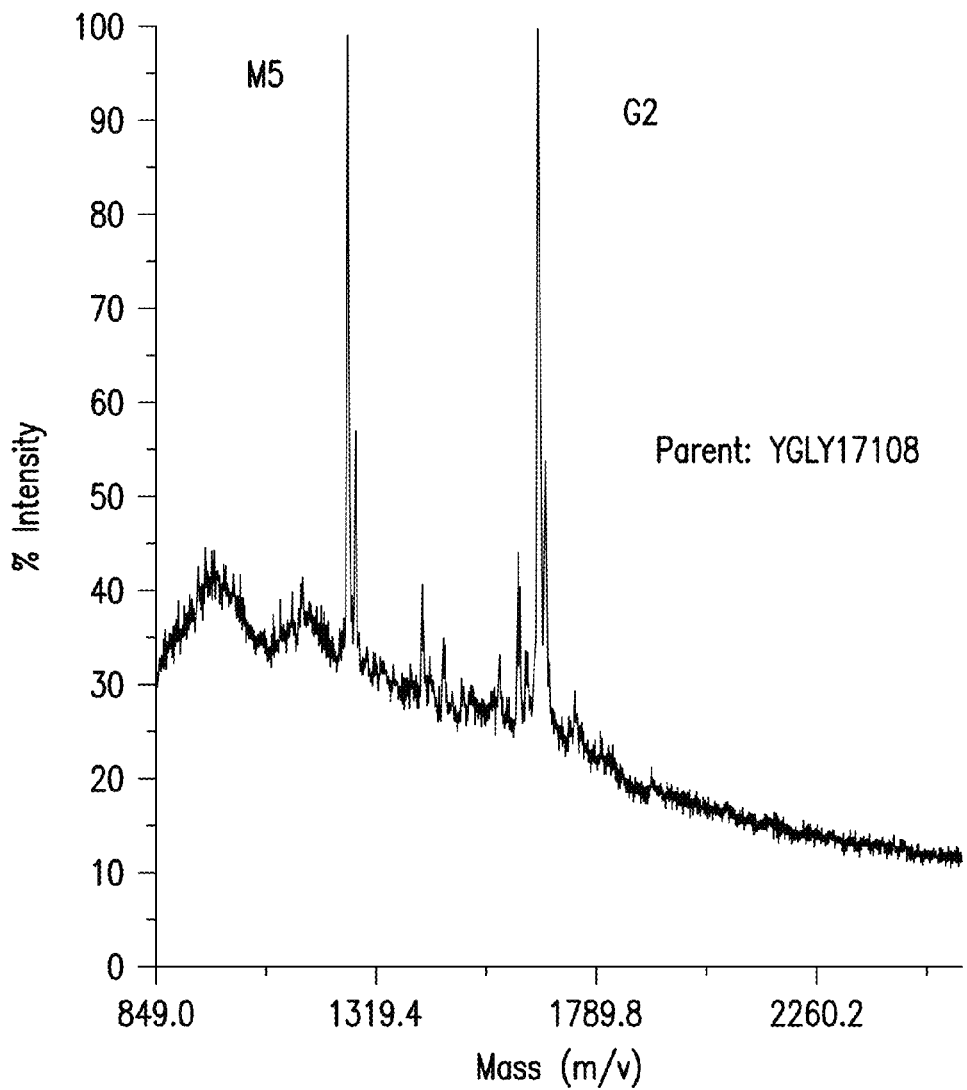
FIGS. 2A-D show N-glycan MALDI-TOF mass spectrometry traces using secreted and whole-cell proteins from four strains YGLY17108 (FIG. 2A), YGLY17177 (FIG. 2B), YGLY22835 (FIG. 2C), and YGLY17159 (FIG. 2D).
Figure 2B:
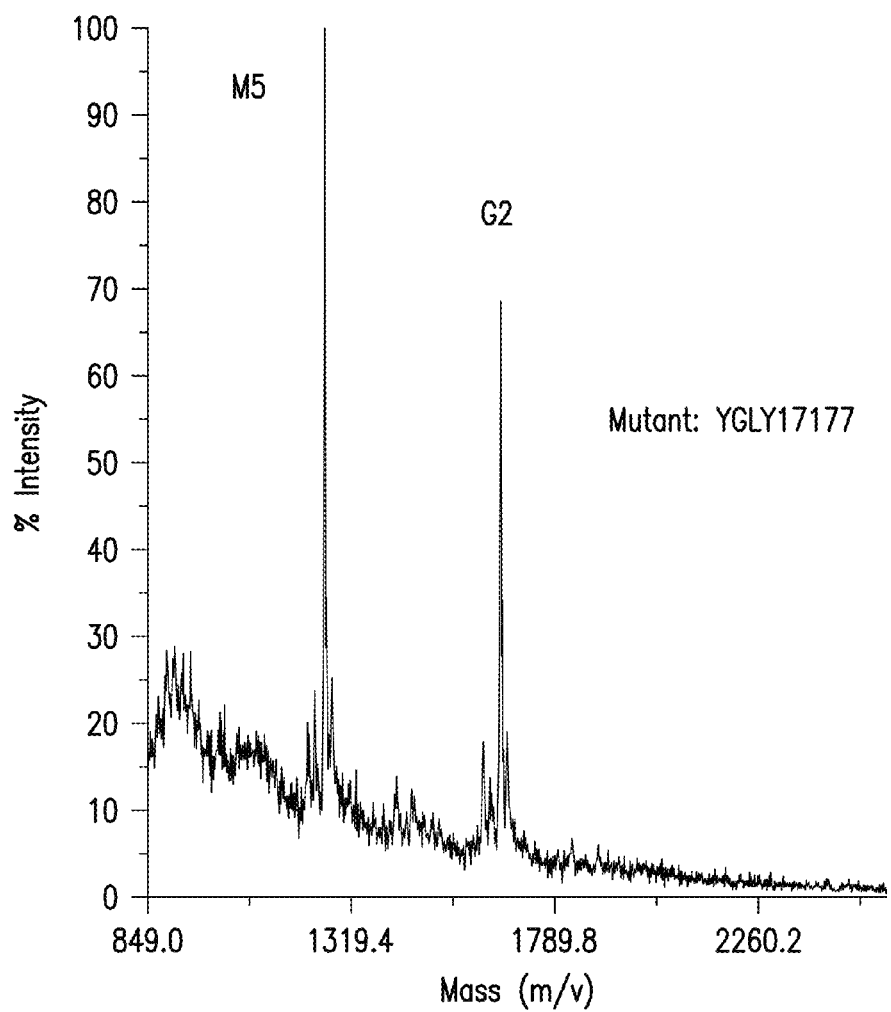
Figure 2C:
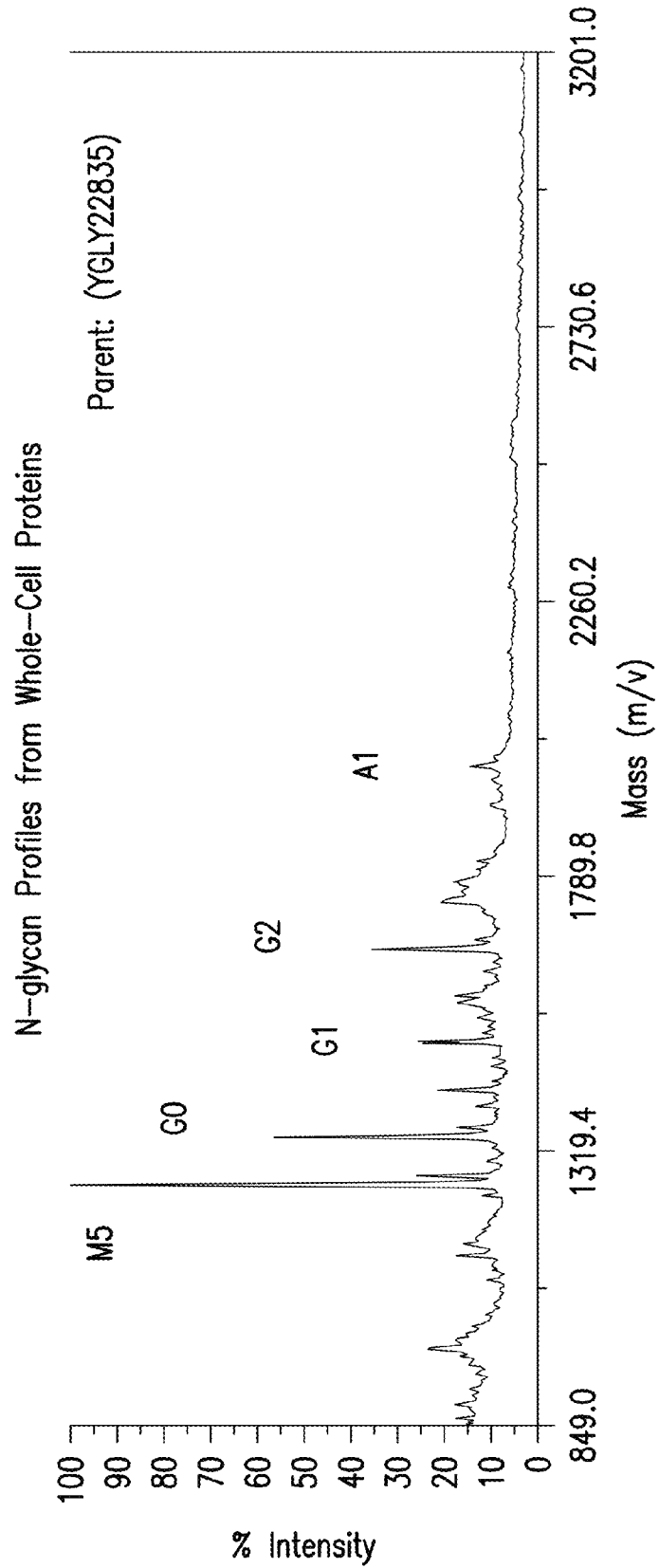
Figure 2D:
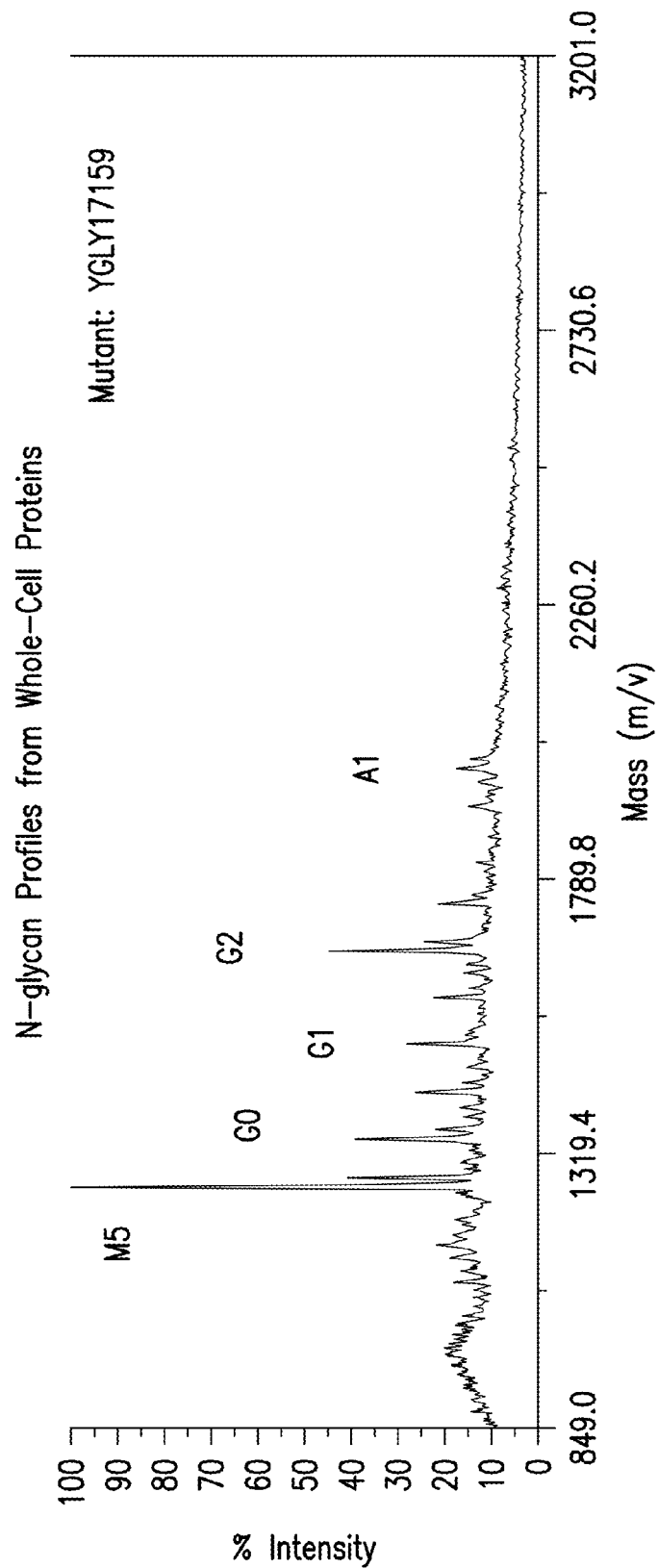

In accordance with the present invention there may be employed conventional molecular biology, microbiology, and recombinant DNA techniques within the skill of the art. Unless otherwise defined herein, scientific and technical terms used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., James M. Cregg (Editor), *Pichia* Protocols (Methods in Molecular Biology), Humana Press (2010), Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I, CRC Press (1976); Handbook of Biochemistry: Section A Proteins, Vol II, CRC Press (1976); Essentials of Glycobiology, Cold Spring Harbor Laboratory Press (1999), Animal Cell Culture (R. I. Freshney, ed. (1986)); Immobilized Cells And Enzymes (IRL Press, (1986)); B. Perbal, A Practical Guide To Molecular Cloning (1984).

A "polynucleotide" and "nucleic acid" includes DNA and RNA in single stranded form, double-stranded form or otherwise.

A "polynucleotide sequence" or "nucleotide sequence" is a series of nucleotide bases (also called "nucleotides") in a nucleic acid, such as DNA or RNA, and means a series of two or more nucleotides. Any polynucleotide comprising a nucleotide sequence set forth herein (e.g., promoters of the present invention) forms part of the present invention.

A "coding sequence" or a sequence "encoding" an expression product, such as an RNA or polypeptide is a nucleotide sequence (e.g., heterologous polynucleotide) that, when expressed, results in production of the product (e.g., a polypeptide comprising SEQ ID NO:7 or a fragment of SEQ ID NO:7).

A "protein", "peptide" or "polypeptide" (e.g., a heterologous polypeptide such SEQ ID NO:7 or as an immunoglobulin heavy chain and/or light chain) includes a contiguous string of two or more amino acids.

A "protein sequence", "peptide sequence" or "polypeptide sequence" or "amino acid sequence" refers to a series of two or more amino acids in a protein, peptide or polypeptide.

The term "isolated polynucleotide" or "isolated polypeptide" includes a polynucleotide or polypeptide, respectively, which is partially or fully separated from other components that are normally found in cells or in recombinant DNA expression systems or any other contaminant. These components include, but are not limited to, cell membranes, cell walls, ribosomes, polymerases, serum components and extraneous genomic sequences. The scope of the present invention includes the isolated polynucleotides set forth herein, e.g., the promoters set forth herein; and methods related thereto, e.g., as discussed herein.

An isolated polynucleotide or polypeptide will, preferably, be an essentially homogeneous composition of molecules but may contain some heterogeneity.

In general, a "promoter" or "promoter sequence" is a DNA regulatory region capable of binding an RNA polymerase in a cell (e.g., directly or through other promoter-bound proteins or substances) and initiating transcription of a coding sequence to which it operably links.

A coding sequence (e.g., of a heterologous polynucleotide, e.g., reporter gene or immunoglobulin heavy and/or light chain) is "operably linked to", "under the control of", "functionally associated with" or "operably associated with" a transcriptional and translational control sequence (e.g., a promoter of the present invention) when the sequence directs RNA polymerase mediated transcription of the coding sequence into RNA, preferably mRNA, which then may be RNA spliced (if it contains introns) and, optionally, translated into a protein encoded by the coding sequence.

The present invention includes vectors or cassettes which comprise a nucleic acid encoding a wildtype ATT1 or a mutated ATT1 coding region (including single nucleotide mutations, frameshift mutations, insertions, truncations and deletions in the ATT1 gene). The present invention also includes vectors that lead to over-expression of ATT1 or a fragment of ATT1 which is able to increase culture stability, thermal tolerance, and/or improved fermentation robustness when overexpressed. The term "vector" includes a vehicle (e.g., a plasmid) by which a DNA or RNA sequence can be introduced into a host cell, so as to transform the host and, optionally, promote expression and/or replication of the introduced sequence. Suitable vectors for use herein include plasmids, integratable DNA fragments, and other vehicles that may facilitate introduction of the nucleic acids into the genome of a host cell (e.g., *Pichia pastoris*). Plasmids are the most commonly used form of vector but all other forms of vectors which serve a similar function and which are, or become, known in the art are suitable for use herein. See, e.g., Pouwels, et al., *Cloning Vectors: A Laboratory Manual*, 1985 and Supplements, Elsevier, N.Y., and Rodriguez et al. (eds.), *Vectors: A Survey of Molecular Cloning Vectors and Their Uses*, 1988, Buttersworth, Boston, Mass.

A polynucleotide (e.g., a heterologous polynucleotide, e.g., encoding an immunoglobulin heavy chain and/or light chain), operably linked to a promoter, may be expressed in an expression system. The term "expression system" means a host cell and compatible vector which, under suitable conditions, can express a protein or nucleic acid which is carried by the vector and introduced to the host cell. Common expression systems include fungal host cells (e.g., *Pichia pastoris*) and plasmid vectors, insect host cells and Baculovirus vectors, and mammalian host cells and vectors.

In general, "inducing conditions" refer to growth conditions which result in an enhanced expression of a polynucleotide (e.g. a heterologous polynucleotide) in a host cell. The term methanol-induction refers to increasing expression of a polynucleotide (e.g., a heterologous polynucleotide) operably linked to a methanol-inducible promoter in a host cell of the present invention by exposing the host cells to methanol.

The following references regarding the BLAST algorithm are herein incorporated by reference: BLAST ALGORITHMS: Altschul, S. F., et al., J. Mol. Biol. (1990) 215:403-410; Gish, W., et al., Nature Genet. (1993) 3:266-272; Madden, T. L., et al., Meth. Enzymol. (1996) 266:131-141; Altschul, S. F., et al., Nucleic Acids Res. (1997) 25:3389-3402; Zhang, J., et al., Genome Res. (1997) 7:649-656; Wootton, J. C., et al., Comput. Chem. (1993) 17:149-163; Hancock, J. M., et al., Comput. Appl. Biosci. (1994) 10:67-70; ALIGNMENT SCORING SYSTEMS: Dayhoff, M. O., et al., "A model of evolutionary change in proteins." in *Atlas of Protein Sequence and Structure* (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in *Atlas of Protein Sequence and Structure*, (1978) vol. 5, suppl. 3." M. O. Dayhoff (ed.), pp. 353-358, Natl. Biomed. Res. Found., Washington, D.C.; Altschul, S. F., J. Mol. Biol. (1991) 219:555-565; States, D. J., et al., Methods (1991) 3:66-70; Henikoff, S., et al., Proc. Natl. Acad. Sci. USA (1992) 89:10915-10919; Altschul, S. F., et al., J. Mol. Evol. (1993) 36:290-300; ALIGNMENT STATISTICS: Karlin, S., et al., Proc. Natl. Acad. Sci. USA (1990) 87:2264-2268; Karlin, S., et al., Proc. Natl. Acad. Sci. USA (1993) 90:5873-5877; Dembo, A., et al., Ann. Prob. (1994) 22:2022-2039; and Altschul, S. F. "Evaluating the statistical significance of multiple distinct local alignments." in *Theoretical and Computational Methods in Genome Research* (S. Suhai, ed.), (1997) pp. 1-14, Plenum, N.Y.

Host Cells

The invention relates to engineered lower eukaryotic host cells that have been modified to reduce or eliminate the activity of the ATT1 gene. In one embodiment, the lower eukaryotic host cell is glyco-engineered. In one embodiment, the lower eukaryotic host cell lacks OCH1 activity. In one embodiment, the lower eukaryotic host cell is a fungal host cell. In one embodiment, the lower eukaryotic host cell is a fungal host cell that lacks OCH1 activity. In another embodiment, the lower eukaryotic host cell host cell is a yeast host cell. In another embodiment, the lower eukaryotic host cell host cell is a yeast host cell that clacks OCH1 activity. In one embodiment, the lower eukaryotic host cell is a *Pichia* sp. In one embodiment, lower eukaryotic host cell is a *Pichia* sp. that lacks OCH1 activity. In one embodiment, the fungal host cell is selected from the group consisting of: *Pichia pastoris, Pichia angusta (Hansenula polymorpha), Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Yarrowia Lipolytica, Kluyveromyces lactic, Zygosaccharomyces rouxii, Zygosaccharomyces bailii, Schwanniomyces occidentalis, Kluyveromyces marxianus, Aspergillus niger, Arxula adeninivorans, Aspergillus nidulans, Aspergillus wentil, Aspergillus aureus, Aspergillus flavus, Ashbya gossypii, Methylophilus methylotrophus, Schizosaccharomyces pombe, Candida boidinii, Candida utilis, Rhizopus myzae, Debaromyces hansenii* and *Saccharyomyces cerevisiae*. In another embodiment, the fungal host cell is *Pichia pastoris*. In another embodiment, the fungal host cell is *Hansenula polymorpha*.

As used herein, a host cell which has reduced ATT1 gene activity or lacks ATT1 gene activity refers to a cell that has an increase in culture stability, thermal tolerance and/or improved fermentation robustness compared with an ATT1 naïve parental host cell under similar culture conditions. In order to determine if a gene has ATT1 activity, the gene can be deleted in a glyco-engineered host cell (for example, an OCH1 minus lower eukaryotic host cell) and the ability of the cell (with the ATT1 gene deletion) to survive in culture at 32° C. within a bioreactor is determined, if the cell has increased culture stability, thermal tolerance and/or improved robustness compared to an ATT1 naïve cell then the gene has ATT1 activity.

As used herein, an "ATT1 naïve host cell" refers to a host cell that comprises a wild-type ATT1 gene in its native genomic state. For example, in one embodiment, an ATT1 naïve host cell refers to a *Pichia pastoris* strain comprising in its native genomic state an ATT1 gene encoding the polypeptide of SEQ ID NO:7 or a natural variant (polymorphs) thereof.

As used herein, an "engineered cell" refers to cell that has been altered using genetic engineering techniques. As used herein, a "glyco-engineered" cell refers to cell that has been genetically engineered to produce glycoproteins where the N- or O-linked glycosylation are modified from their native form, either through inactivation or deletion of genes or through the heterologous expression of glycosyltransferases or glycosidases.

As used herein "thermal tolerance" refers to increase in temperature resistance (i.e. ability to grow in culture to temperatures of at least about 32° C.).

As used herein, "improved fermentation robustness" refers to an increase in cell viability or decrease in cell lysis during fermentation.

The invention encompasses any engineered lower eukaryotic host cell which has been modified to: reduce or eliminate the activity of an ATT1 gene which is an ortholog of the *Pichia pastoris* ATT1 gene; wherein the cell exhibits an increase in culture stability, thermal tolerance, and/or improved fermentation robustness when compared to an ATT1 naïve parental host cell.

The invention also relates to an engineered lower eukaryotic host cell which has been modified to (i) reduce or eliminate expression of an ATT1 gene or polypeptide which is an ortholog of the *Pichia pastoris* ATT1 gene, (ii) express a mutated form of an ATT1 gene which is an ortholog of the *Pichia pastoris* ATT1 gene, or (iii) to over-express an ATT1 gene which is an ortholog of the *Pichia pastoris* ATT1 gene or a fragment of said gene; wherein said cell exhibits an increase in culture stability, thermal tolerance, and/or improved fermentation robustness when compared to an ATT1 naïve parental host cell. In one embodiment, the invention relates to an engineered lower eukaryotic host cell which has been modified to reduce or eliminate expression of an ATT1 gene or polypeptide which is an ortholog of the *Pichia pastoris* ATT1 gene or to express a mutated form of an ATT1 gene which is an ortholog of the *Pichia pastoris* ATT1 gene; wherein said cell exhibits an increase in culture stability, thermal tolerance, and/or improved fermentation robustness when compared to an ATT1 naïve parental host cell. In another embodiment, the invention relates to a lower eukaryotic host cell which has been modified to over-express an ATT1 gene which is an ortholog of the *Pichia pastoris* ATT1 gene, or a functional or dominant-negative fragment of said gene; wherein said cell exhibits an increase in culture stability, thermal tolerance, and/or improved fermentation robustness when compared to an ATT1 naïve parental host cell.

As used herein, an ortholog to the *Pichia pastoris* ATT1 gene, is a gene that has sequence similarity to the *Pichia pastoris* ATT1 gene and has ATT1 activity. In one embodiment, the sequence similarity will be at least 25%. A person of skill in the art would be able to identify such orthologs using only routine experimentation. For example, the *H. polymorpha* ATT1 ortholog has been identified as described in Example 9. Other fungal/yeast orthologs could be similarly identified, for example by the use of reciprocal BLAST analysis. The following genes have been identified as potential orthologs of the *Pichia pastoris* ATT1 gene:

| Fungal host cell | Sequence/GenBank Accession No. |
| --- | --- |
| *Pichia stipitis* | SEQ ID NO: 24 (XP_001385092.2) |
| *Pichia guilliermondii* | SEQ ID NO: 25 (XP_001482364.1) |
| *Kluyveromyces lactis* | SEQ ID NO: 26 (XP_453627.1) |
| *Aspergillus niger* | SEQ ID NO: 27 (EHA19999.1) |
| *Aspergillus nidulans* | SEQ ID NO: 28 (CBF76786.1) |
| *Aspergillus flavus* | SEQ ID NO: 29 (XP_002378619.1) |
| *Debaryomyces hansenii* | SEQ ID NO: 30 (XP_458171.2) |
| *Zygosaccharomyces rouxii* | SEQ ID NO: 31 (XP_002499285.1) |
| *Sacchromyces cerevisiae* | SEQ ID NO: 32 (CAA97969.1) |

The host cells of the invention could be in haploid, diploid, or polyploid state. Further, the invention encompasses a diploid cell wherein only one endogenous chromosomal ATT1 gene has been mutated, disrupted, truncated or deleted.

In one embodiment, the engineered lower eukaryotic host cell of the invention is selected from the group consisting of: *Pichia pastoris*, *Pichia angusta* (*Hansenula polymorpha*), *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pijperi*, *Pichia stiptis*, *Pichia methanolica*, *Yarrowia Lipolytica*, *Kluyveromyces lactis*, *Zygosaccharomyces rouxii*, *Zygosaccharomyces bailii*, *Schwanniomyces occidentalis*, *Kluyveromyces marxianus*, *Aspergillus niger*, *Arxula adeninivorans*, *Aspergillus nidulans*, *Aspergillus wentii*, *Aspergillus aureus*, *Aspergillus flavus*, *Ashbya gossypii*, *Methylophilus methylotrophus*, *Schizosaccharomyces pombe*, *Candida boidinii*, *Candida utilis*, *Rhizopus oryzae* and *Debaromyces hansenii*. In an embodiment of the invention, the host cell is selected from the group consisting of any *Pichia* cell, such as *Pichia pastoris*, *Pichia angusta* (*Hansenula polymorpha*), *Pichia finlandica*, *Pichia trehalophila*, *Pichia koclamae*, *Pichia membranaefaciens*, *Pichia minuta* (*Ogataea minuta*, *Pichia lindneri*), *Pichia opuntiae*, *Pichia thermotolerans*, *Pichia salictaria*, *Pichia guercuum*, *Pichia pyperi*, *Pichia stiptis*, and *Pichia methanolica*. In one embodiment, the host cell is an engineered *Pichia pastoris* host cell and the ATT1 gene encodes a polypeptide comprising the amino acid sequence of SEQ ID NO:7 or a natural variant of said polypeptide. In another embodiment, the host cell is an engineered *H. polymorpha* host cell and the ATT1 gene encodes a polypeptide comprising the amino acid sequence of SEQ ID NO:23 or a natural variant of said polypeptide. In one embodiment, the host cell is an engineered *Pichia stipitis* host cell and the ATT1 gene encodes a polypeptide comprising the amino acid sequence of SEQ ID NO:24 or a natural variant of said polypeptide. In another embodiment, the host cell is an engineered *Pichia guilliermondii* host cell and the ATT1 gene encodes a polypeptide comprising the amino acid sequence of SEQ ID NO:25 or a natural variant of said polypeptide. In another embodiment, the host cell is an engineered *Kluyveromyces lactis* host cell and the ATT1 gene encodes a polypeptide comprising the amino acid sequence of SEQ ID NO:26 or a natural variant of said polypeptide. In another embodiment, the host cell is an engineered *Aspergillus niger* host cell and the ATT1 gene encodes a polypeptide comprising the amino acid sequence of SEQ ID NO:27 or a natural variant of said polypeptide. In another embodiment, the host cell is an engineered *Aspergillus nidulans* host cell and the ATT1 gene encodes a polypeptide comprising the amino acid sequence of SEQ ID NO:28 or a natural variant of said polypeptide. In another embodiment, the host cell is an engineered *Aspergillus flavus* host cell and the ATT1 gene encodes a polypeptide comprising the amino acid sequence of SEQ ID NO:29 or a natural variant of said polypeptide. In another embodiment, the host cell is an engineered *Debaryomyces hansenii* host cell and the ATT1 gene encodes a polypeptide comprising the amino acid sequence of SEQ ID NO:30 or a natural variant of said polypeptide. In another embodiment, the host cell is an engineered *Zygosaccharomyces rouxii* host cell and the ATT1 gene encodes a polypeptide comprising the amino acid sequence of SEQ ID NO:31 or a natural variant of said polypeptide. In another embodiment, the host cell is an engineered *Sacchromyces cerevisiae* host cell and the ATT1 gene encodes a polypeptide comprising the amino acid sequence of SEQ ID NO:32 or a natural variant of said polypeptide.

In one embodiment, the engineered lower eukaryotic host cells of the invention further comprise a mutation, disruption or deletion of one or more of genes. In one embodiment, the engineered lower eukaryotic host cell of the invention comprises a mutation, disruption or deletion of one or more genes encoding protease activities, alpha-1,6-mannosyltransferase activities, alpha-1,2-mannosyltransferase activities mannosylphosphate transferase activities, β-mannosyltransferase activities, O-mannosyltransferase (PMT) activities, and/or dolichol-P-Man dependent alpha(1-3) mannosyltransferase activities. In one embodiment, an engineered lower eukaryotic host cell of the invention comprises a mutation, disruption or deletion in the OCH1 gene. In one embodiment, an engineered lower eukaryotic host cell of the invention comprises a mutation, disruption or deletion in the BMT1, BMT2, BMT3, and BMT4 genes. In one embodiment, an engineered lower eukaryotic host cell of the invention comprises a mutation, disruption or deletion in the PNO1, MNN4, and MNN4L1 genes. In one embodiment, an engineered lower eukaryotic host cell of the invention comprises a mutation, disruption or deletion in the PEP4 and PRB1 genes. In another embodiment, an engineered lower eukaryotic host cell of the invention comprises a mutation, disruption or deletion of the ALG3 gene (as described in US Patent Publication No. US2005/0170452). In one embodiment, an engineered lower eukaryotic host cell of the invention comprises a mutation, disruption or deletion of all of the following genes: OCH1, BMT1, BMT2, BMT3, BMT4, PNO1, MNN4, and MNN4L1. In one embodiment, an engineered lower eukaryotic host cell of the invention comprises a mutation, disruption or deletion of all of the following genes: OCH1, BMT1, BMT2, BMT3, BMT4, PNO1, MNN4, MNN4L1, PEP4 and PRB1. In one embodiment, an engineered lower eukaryotic host cell of the invention comprises a mutation, disruption or deletion of all of the following genes: OCH1, BMT1, BMT2, BMT3, BMT4, PNO1, MNN4, MNN4L1, ALG3, PEP4 and PRB1. In some embodiments, the host cell of the invention can be cultivated in a medium that includes one or more Pmtp inhibitors. Pmtp inhibitors include but are not limited to a benzylidene thiazolidinedione. Examples of benzylidene thiazolidinediones are 5-[[3,4bis(phenylmethoxy)phenyl]methylene]-4-oxo-2-thioxo-3-thiazolidineacetic Acid; 5-[[3-(1-25 Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl]methylene]-4-oxo-2-thioxo3-thiazolidineacetic acid.

In one embodiment, an engineered lower eukaryotic host cell of the invention lacks OCH1 activity. In one embodiment, the invention comprises a lower eukaryotic host cell (e.g., *Pichia* sp.) that has been modified to: (i) reduce or eliminate expression of an ATT1 gene or polypeptide, (ii) express a mutated form of an ATT1 gene, or (iii) over-express an ATT1 gene or a fragment of the ATT1, wherein the cell lacks OCH1 activity. Lower eukaryotic cells lacking OCH1 activity have been described in the art and have been shown to be temperature sensitive. See, e.g., Choi et al., 2003; Bates et al., *J. Biol. Chem.* 281(1):90-98 (2006); Woog Kim et al., *J. Biol. Chem.* 281(10):6261-6272 (2006); Yoko-o et al., *FEBS Letters* 489 (1):75-80 (2001); and Nakayama et al., *EMBO J* 11(7):2511-2519 (1992). Accordingly, it is desirable to modify cells that lack OCH1 activity to render them thermotolerant.

In an embodiment of the invention, an engineered lower eukaryotic host cell of the invention is further genetically engineered to include a nucleic acid that encodes an alpha-1, 2-matmosidase that has a signal peptide that directs it for secretion. For example, in an embodiment of the invention, the host cell of the invention is engineered to express an exogenous alpha-1,2-mannosidase enzyme having an optimal pH between 5.1 and 8.0, preferably between 5.9 and 7.5. In an embodiment of the invention, the exogenous enzyme is targeted to the endoplasmic reticulum or Golgi apparatus of the host cell, where it trims N-glycans such as $Man_8GlcNAc_2$ to yield $Man_5GlcNAc_2$. See U.S. Pat. No. 7,029,872. Lower eukaryotic host cells expressing such alpha-1,2-mannosidase activity have been described in the art, see, e.g., Choi et al., 2003. In one embodiment, the glyco-engineered lower eukaryotic host cell of the invention lacks OCH1 activity and comprises an alpha1,2 mannosidase.

In another embodiment, engineered lower eukaryotic host cells (e.g., *Pichia* sp.) of the invention that have been modified to: (i) reduce or eliminate expression of an ATT1 gene or polypeptide, (ii) express a mutated form of an ATT1 gene, or (iii) over-express an ATT1 gene or a fragment of the ATT1, are further genetically engineered to eliminate glycoproteins having alpha-mannosidase-resistant N-glycans by deleting or disrupting one or more of the beta-mannosyltransferase genes (e.g., BMT1, BMT2, BMT3, and BMT4) (See, U.S. Pat. No. 7,465,577) or abrogating translation of RNAs encoding one or more of the beta-mannosyltransferases using interfering RNA, antisense RNA, or the like.

In some embodiments, engineered lower eukaryotic host cells (e.g., *Pichia* sp.) of the present invention that have been modified to: (i) reduce or eliminate expression of an ATT1 gene or polypeptide, (ii) express a mutated form of an ATT1 gene, or (iii) over-express an ATT1 gene or a fragment of the ATT1, are further genetically engineered to eliminate glycoproteins having phosphomannose residues, e.g., by deleting or disrupting one or more of the phosphomannosyl transferase genes (i.e., PNO1, MNN4 and MNN4L1 (see e.g., U.S. Pat. Nos. 7,198,921 and 7,259,007)), or by abrogating translation of RNAs encoding one or more of the phosphomannosyltransferases using interfering RNA, antisense RNA, or the like.

Additionally, engineered lower eukaryotic host cells (e.g., *Pichia* sp.) of the invention that have been modified to: (i) reduce or eliminate expression of an ATT1 gene or polypeptide, (ii) express a mutated form of an ATT1 gene, or (iii) over-express an ATT1 gene or a fragment of the ATT1, may be further genetically engineered to include a nucleic acid that encodes the *Leishmania* sp. single-subunit oligosaccharyl-transferase STT3A protein, STT3B protein, STT3C protein, STT3D protein, or combinations thereof such as those described in WO2011/06389.

In some embodiments, the engineered lower eukaryotic host cell of the invention further comprises a promoter operably linked to a polynucleotide encoding a heterologous polypeptide (e.g., a reporter or immunoglobulin heavy and/or light chain). The invention further comprises methods of using the host cells of the invention, e.g., methods for expressing the heterologous polypeptide in the host cell. The engineered lower eukaryotic host cell of the invention may be also genetically engineered so as to express particular glycosylation patterns on polypeptides that are expressed in such cells. For example, host cells of the present invention may be modified to produce polypeptides comprising N-glycans. In one embodiment, the host cells of the invention may be engineered to produce high mannose, hybrid or complex-type N-glycans.

As used herein, the terms "N-glycan" and "glycoform" are used interchangeably and refer to an N-linked oligosaccharide, e.g., one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. Predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)).

N-glycans have a common pentasaccharide core of $Man_3GlcNAc_2$ ("Man" refers to mannose; "Glc" refers to glucose; and "NAc" refers to N-acetyl; GlcNAc refers to N-acetylglucosamine). N-glycans differ with respect to the number of branches (antennae) comprising peripheral sugars (e.g., GlcNAc, galactose, fucose and sialic acid) that are added to the $Man_3GlcNAc_2$ ("$Man_3$") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms". "PNGase" or "glycanase" refers to peptide N-glycosidase F (EC 3.2.2.18).

In an embodiment of the invention, engineered lower eukaryotic host cells (e.g., *Pichia* sp.) of the invention that have been modified to: (i) reduce or eliminate expression of an ATT1 gene or polypeptide, (ii) express a mutated form of an ATT1 gene, or (iii) over-express an ATT1 gene or a fragment of the ATT1, are further genetically engineered to produce glycoproteins that have predominantly an N-glycan selected from the group consisting of complex N-glycans, hybrid N-glycans, and high mannose N-glycans. In one embodiment, the high mannose N-glycans are selected from the group consisting of $Man_6GlcNAc_2$, $Man_7GlcNAc_2$, Man$_8$GlcNAc$_2$, and Man$_9$GlcNAc$_2$. In one embodiment, the host cell of the invention is engineered to produce glycoproteins that have predominantly Man$_{8-10}$GlcNAc$_2$ N-glycans (Example 13). In one embodiment, the N-glycans are selected from the group consisting of Man$_5$GlcNAc$_2$ (Example 13), GlcNAcMan$_5$GlcNAc$_2$, GalGlcNAcMan$_5$GlcNAc$_2$, and NANAGalGlcNAcMan$_5$GlcNAc$_2$. In one embodiment, the N-glycans are selected from the group consisting of Man$_3$GlcNAc$_2$, GlcNAC$_{(1-4)}$Man$_3$GlcNAc$_2$, NANA$_{(1-4)}$GlcNAc$_{(1-4)}$Man$_3$GlcNAc$_2$, and NANA$_{(1-4)}$Gal$_{(1-4)}$Man$_3$GlcNAc$_1$. In one embodiment, the N-glycans comprise predominantly a Man$_3$GlcNAc$_2$ structure. In one embodiment, the N-glycans comprise predominantly NANA$_{(1-4)}$Gal$_{(1-4)}$Man$_3$GlcNAc$_2$. In one embodiment, the N-glycans comprise predominantly NANA$_2$Gal$_2$Man$_3$GlcNAc$_2$. In one embodiment, the host cell of the invention is engineered to produce glycoproteins that have galactosylated N-glycans (Example 1). In one embodiment, the host cell of the invention is engineered to produce glycoproteins that have sialylated N-glycans (Example 2 and WO2011/149999).

Characterization of *Pichia Pastoris* ATT1

Mutations within a novel *Pichia pastoris* gene ATT1 (SEQ ID NO:1, acquiring thermal tolerance, which is orthologous to *S. cerevisiae* GAL4 transcription factor) resulted in premature truncations of the ATT1 protein product and were identified in a set of *Pichia* mutants that exhibited increased thermal tolerance. These mutations led to a significant enhancement in temperature resistance (i.e. stability in culture to temperatures of at least about 35° C.) and improved fermentation robustness for those *Pichia* host strains harboring these mutations (i.e. ATT1 mutant *Pichia* strains exhibited decreased lysis, extended induction/production phase, and produced heterologous protein products with decreased proteolytic degradation as well as desired glycosylation patterns).

To broadly improve strain quality, several temperature-resistant *P. pastoris* mutant strains with significantly improved fermentation robustness were identified from a set of temperature-resistant mutants. While non-mutagenized glyco-engineered parental strains typically display a temperature-sensitive phenotype when grown on Petri dishes (Choi et al. 2003) and generally display a high level of cell lysis within 24 hours of MeOH induction at 32° C. when cultured within a bioreactor, the ATT1 mutant strains described herein are viable for more than 100 hours after induction at 32° C. when cultured within a bioreactor, without showing obvious signs of cell-lysis. This extended induction period allows for significantly increased yield and quality of multiple recombinant proteins, desirable traits for production of heterologous proteins such as antibody and non-antibody therapeutics.

Such mutations in ATT1 when engineered into any yeast host strain could serve to improve fermentation robustness, improve recombinant protein yield, and reduce protein product proteolytic degradation.

Experimental Methods

Fed-batch fermentations, IgG purifications, N-glycan characterizations, as well as all other analytical assays, were performed as previously described (Barnard et al. 2010; Jiang et al. 2011; Potgieter et al. 2009; Winston F 2008). Except otherwise specified, all 1 L Bioreactor fermentation runs described in this application are scheduled to end after 100-120 hours of MeOH induction. However, a fermentation run will be terminated prematurely if excess cell lysis is observed. Cell lysis is determined either by microscopic examination, or by measuring the amount of nuclear DNA released into the supernatant (Barnard, 2010). For this application, excess cell lysis is defined by either greater than 80% cells were lysed by microscopic examination, or greater than 30 microgram/ml DNA concentration in the supernatant determined by Picogreen assay. UV mutagenesis was performed as described by Winston (Winston 2008). Briefly, *Pichia* strains were grown in 40 ml YSD liquid medium overnight at 24° C. Upon reaching an OD$_{600}$ of 5, an aliquot of $10^6$ to $10^7$ cells was transferred onto the surface of a 100 mm YSD agar Petri dish, and treated, with the lid off, with 5 mJ/cm$^2$ of UV irradiation. After the UV treatment, the Petri dish was immediately covered with aluminum foil (to prevent photo-induced DNA repair) and the mutagenized cells were allowed to recover at 24° C. for 18 hours in the dark. Then, these recovered cells were transferred to 35° C. incubator to select for temperature-resistant mutants. After 7-10 days incubation at 35° C., colonies were picked and re-streaked onto fresh YSD plates and incubated at 35° C., and only the clones displaying the temperature-resistant phenotype upon restreak were retained as temperature-resistant mutants.

Example 1

Figure 7:
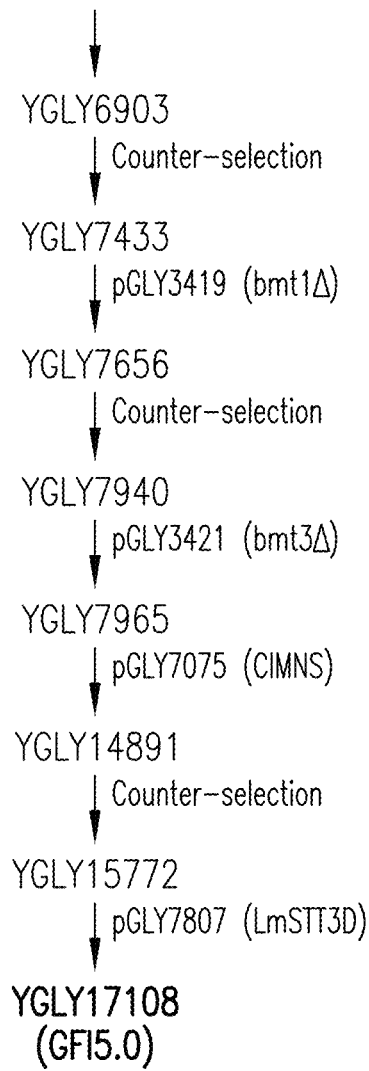
FIG. 7 shows strain lineages from yGLY6903 through yGLY17108.
Figure 8:
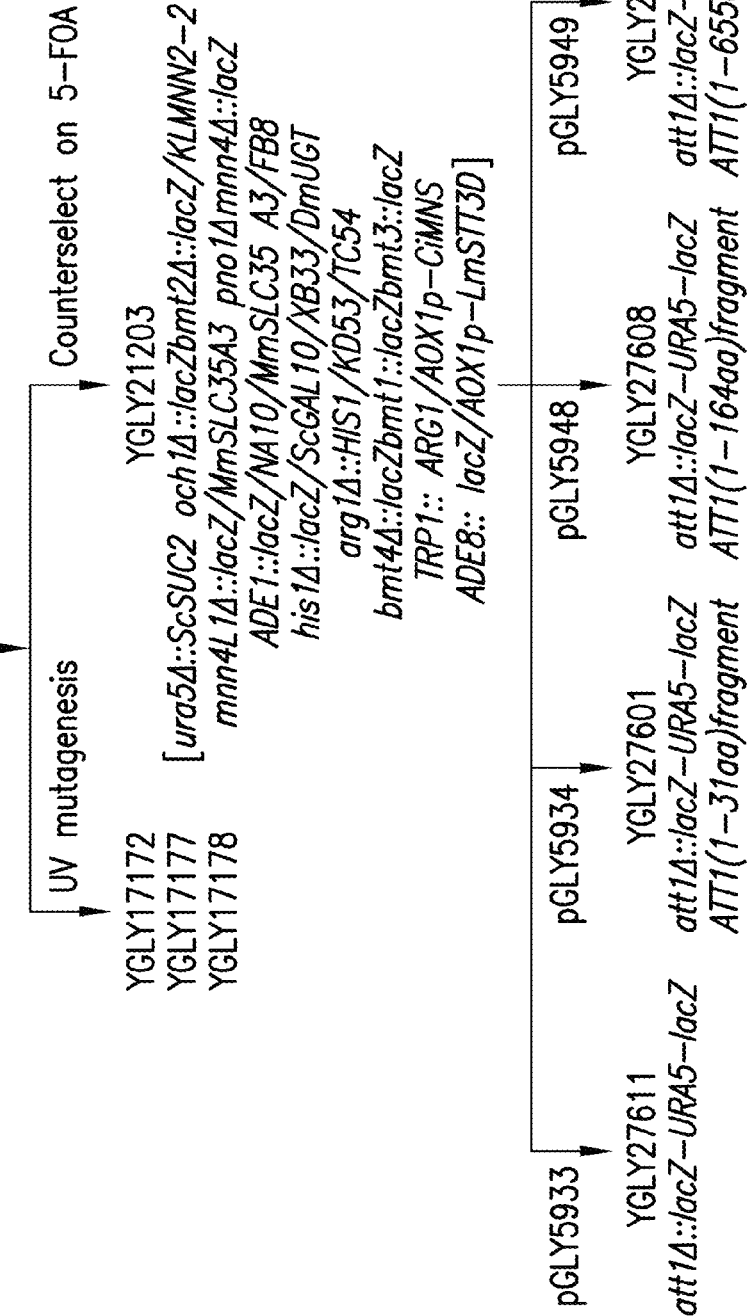
FIG. 8 shows ATT1 mutant lineages from yGLY17108 (GFI5.0) background.
Figure 9:
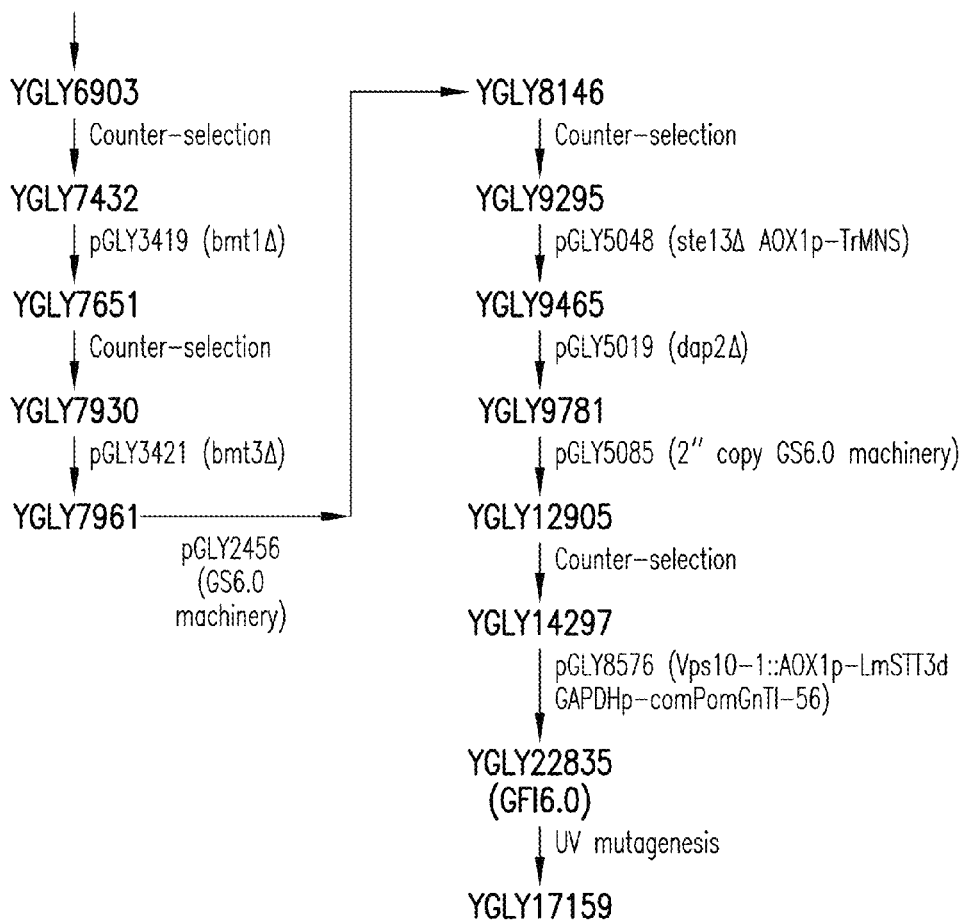
FIG. 9 shows strain lineages from yGLY6903 through yGLY22835 and yGLY17159.

Temperature-Resistant Mutants Displayed Substantially Enhanced Fermentation Robustness and Productivity Two temperature-sensitive glyco-engineered empty host strains, YGLY17108 and YGLY22835 were subjected to UV mutagenesis as described herein, to identify *Pichia* host strains with increased fermentation robustness. Host strain YGL17108 has been engineered to produce galactosylated glycoproteins having predominantly Gal2GlcNAc2Man3GlcNAc2 N-glycans (Bobrowicz et al. 2004, and U.S. Pat. No. 7,795,002). Host strain YGL22835 has been engineered to produce sialylated glycoproteins having predominantly NANA2Gal2GlcNAc2Man3GlcNAc2 N-glycans (Hamilton et al. 2006 and wo2012/115904). The glyco-engineered host strain YGLY17108 was derived originally from the NRRL-Y11430 strain through a series of modifications as described in WO2011/06389, to arrive at strain YGLY7965. The genetic background and strain lineage for additionally modified strains from YGLY6903 and ending with host strain YGLY17108 is shown in FIG. 7. The genetic background and strain lineages from YGLY6903 through YGLY22835 and yGLY17159 are shown in FIG. 9. An overview of the strains obtained from the UV mutagenesis experiments is shown in FIG. 8.

Temperature-resistant colonies were selected and fermented using standard MeOH fed-batch runs in 1.0 L DasGip Bioreactors to evaluate strain robustness during the fermentation process (Hopkins et al. 2011). After an extensive fermentation screening, four mutants YGLY17172, YGLY17177, YGLY17178, and YGLY17159 were identified displaying dramatically enhanced fermentation robustness (Table 1). Both of the non-mutagenized parental strains YGLY17108 and YGLY22835 suffered heavy lysis and a major loss of cell viability within 24 hours of induction at 32°

C. (indicated in Table 1 as a lysis score of 5, which indicates a large amount of cell lysis). In contrast, the four temperature-resistant mutants (YGLY17172, YGLY17177, YGLY17178, and YGLY17159) all displayed dramatically improved fermentation robustness and were viable for more than 100 hours following induction at 32° C., with little cell-lysis observed (with lysis scores <2 out of 5, as shown in Table 1). A lysis score of 0.5-5.0 was assigned based on microcopic examination. A lysis score of 0.5 indicates minimal lysis (more than 95% intact cells), and a lysis score of 5 indicates high lysis (less than 10% intact cells).

TABLE 1

Isolated Mutants Displayed Improved Fermentation Robustness

| 1 L Bioreactor MeOH | | Lysis score at 32° C. | | | |
|---|---|---|---|---|---|
| Induction Phase | | Day 1 | Day 2 | Day 3 | Day 4 |
| YGLY17108 | GFI5.0 control | 5* | | Harvest | |
| YGLY17172 | GFI5.0 mutant | 0.5 | 0.5 | 1/1.5 | 2/2.5 |
| YGLY17177 | GFI5.0 mutant | 0.5 | 0.5 | 1 | 1 |
| YGLY17178 | GFI5.0 mutant | 0.5 | 1 | 1 | 2 |
| YGLY22835 | GFI6.0 control | 5* | | Harvest | |
| YGLY17159 | GFI6.0 mutant | 0.5 | 0.5 | 0.5/1 | 1 |

*lysis score: 0-5, with 5 indicating the greatest amount of lysis

Example 2

Genome Sequencing to Identify the Causative Mutation(s) Responsible for the Enhanced Thermal-Tolerance and Fermentation Robustness Genome-sequencing was performed on the four independently isolated mutants and the parental strains to identify and characterize the mutations responsible for the increased thermal tolerance and fermentation robustness. After genome-wide comparisons between the mutants and their corresponding parents, from 1 to 9 non-synonymous nucleotide alterations (indicated by a "+" in Table 2) were identified in each of these 4 mutants. Most of these non-synonymous mutations are caused by single-nucleotide variants with one exception of a 5 bp insertion found in the YGLY17159 mutant. One mutant, YGLY17178, contained only one non-synonymous SNV, which is a single non-sense mutation within an uncharacterized transcription factor, which was named ATT1 (acquiring thermal tolerance). Non-sense or frame-shift mutations in the ATT1 gene were also identified in the other three mutants, indicating that mutations of this transcription factor are associated with the temperature resistance and fermentation robustness phenotypes.

TABLE 2

Non-Synonymous Nucleotide Alterations Identified by Genome Sequencing

| Chromosome | position | YGLY17108 | YGLY17172 | YGLY17177 | YGLY17178 | YGLY22835 | YGLY17159 | reference allele | mutanted allele |
|---|---|---|---|---|---|---|---|---|---|
| chr1 | 160070 | − | − | − | − | − | + | T | TGAATC |
| chr1 | 160305 | − | − | − | + | − | − | C | T |
| chr1 | 160476 | − | − | + | − | − | − | A | T |
| chr1 | 161949 | − | + | − | − | − | − | C | T |
| chr1 | 279682 | − | − | − | − | − | + | T | A |
| chr1 | 981612 | − | − | − | − | − | − | A | G |
| chr1 | 1029402 | − | − | + | − | − | − | C | T |
| chr1 | 1084421 | − | + | − | − | − | − | A | G |
| chr1 | 1203497 | − | − | + | − | − | − | A | G |
| chr1 | 1308858 | − | + | − | − | − | − | A | G |
| chr2 | 386047 | − | − | − | − | − | + | T | C |
| chr2 | 1391195 | − | − | + | − | − | − | A | G |
| chr2 | 1401784 | − | + | − | − | − | − | T | A |
| chr2 | 1941747 | − | − | + | − | − | − | T | C |
| chr3 | 139943 | − | − | − | − | − | + | A | T |
| chr3 | 230758 | − | + | − | − | − | − | G | A |
| chr3 | 640255 | − | − | − | − | − | + | C | T |
| chr3 | 875268 | − | − | + | − | − | − | A | G |
| chr3 | 973319 | − | − | + | − | − | − | C | T |
| chr3 | 1586501 | − | − | − | − | − | + | A | G |
| chr3 | 2123889 | − | − | + | − | − | − | A | G |
| chr4 | 704482 | − | − | + | − | − | − | T | A |
| chr4 | 1374513 | − | − | − | − | − | + | A | G |

| Chromosome | SNV type | gene-id | refrence condon | mutated condon | refrence AA | mutanted AA | Gene Symbol |
|---|---|---|---|---|---|---|---|
| chr1 | insertion | Pp01g00680 | | | | frame-shift | ATT1 |
| chr1 | nonsyn | Pp01g00680 | CAG | TAG | Q | Stop | ATT1 |
| chr1 | nonsyn | Pp01g00680 | AAA | TAA | K | Stop | ATT1 |
| chr1 | nonsyn | Pp01g00680 | CGA | TGA | R | Stop | ATT1 |
| chr1 | nonsyn | Pp01g01360 | ATC | TTC | I | F | AIP1 |
| chr1 | nonsyn | Pp01a05170 | TAC | TGC | Y | C | SSK2 |
| chr1 | nonsyn | Pp01g05460 | AGA | AAA | R | K | RRT12 |
| chr1 | nonsyn | Pp01g05760 | AAG | GAG | K | E | SDS23 |
| chr1 | nonsyn | Pp01g06460 | AAA | GAA | K | E | NOT5 |
| chr1 | nonsyn | Pp01g07000 | TTA | TCA | L | S | DPS1 |
| chr2 | nonsyn | Pp02g02120 | TTC | TCC | F | S | CRZ1 |
| chr2 | nonsyn | Pp02g07550 | TTG | TCG | L | S | CTK1 |
| chr2 | nonsyn | Pp02g07600 | TAT | TTT | Y | F | RGD2 |
| chr2 | nonsyn | Pp02g10670 | TCA | CCA | S | P | AVO2 |
| chr3 | nonsyn | Pp03g00790 | AAA | TAA | K | Stop | YMR196W |
| chr3 | nonsyn | Pp03g01260 | GAA | AAA | E | K | PEX1 |
| chr3 | nonsyn | Pp03g03550 | TCT | TTT | S | F | TYW1 |

TABLE 2-continued

Non-Synonymous Nucleotide Alterations Identified by Genome Sequencing

| | | | | | | | |
|---|---|---|---|---|---|---|---|
| chr3 | nonsyn | Pg03g04770 | CTG | CCG | L | P | POM152 |
| chr3 | nonsyn | Pp03g05310 | CCT | CTT | P | L | YPR084W |
| chr3 | nonsyn | Pp03g08800 | TAT | CAT | Y | H | |
| chr3 | nonsyn | Pp03g11890 | TTA | TCA | L | S | |
| chr4 | nonsyn | Pp05g04100 | AAT | ATT | N | I | MAK5 |
| chr4 | nonsyn | Pp05g07960 | CTA | CCA | L | P | AZF1 |

All four mutations (three non-sense mutations and one frame-shift insertion) resulted in premature gene-product truncations after amino acid 31, 107, 164, or 655 (FIGS. 1A-B). FIGS. 1A-B show the sequence homology between ScGAL4 and PpATT1. The symbol "#" at amino acid 31 indicates the position of the 5 bp insertion found in YGLY17159, and the symbol "@" signs indicate the stop-codon mutations identified from YGL17178 (at amino acid 107), YGL17177 (amino acid 164) and YGLY17172 (amino acid 655). ScGAL4 is a key transcription factor involved in the regulation of galactose metabolic enzymes in baker's yeast (Traven et al. 2006). *Pichia pastoris* does not metabolize galactose, so the biological function of this ATT1 gene in *Pichia* was at the time that the application was filed still unknown.

The *Pichia* ATT1 gene (SEQ ID NO:1) codes for a 995 amino acid protein product SEQ ID NO:7, which contains an N-terminal domain (amino acid residues 39 to 114) highly homologous to the *S. cerevisiae* GAL4 DNA-binding domain, a conserved fungal specific transcription factor domain at amino acid residues 351-519, and a C-terminus region sharing a low level of conservation to the C-terminus of the *S. cerevisiae* GAL4 gene product, as shown in the alignment in FIGS. 1A-B.

Three of the mutants, YGL17172, YGL17177, and YGL17178, are derived from the parent host strain YGL17108 which has been engineered to produce complex N-glycan forms with terminal galactose (Bobrowicz et al. 2004, and U.S. Pat. No. 7,795,002). The fourth mutant, YGL17159, is derived from host strain YGL22835, which is capable of producing fully sialylated N-glycans (Hamilton et al. 2006, and U.S. Ser. No. 61/446,853). Comparison of the N-glycan profiles obtained from the isolated mutants with those of their respective parents showed that N-glycan compositions isolated from the mutants are virtually indistinguishable to the N-glycan profiles obtained from their non-mutagenized parent strains, confirming that all four mutants retained their capability to make complex human glycans. Representative N-glycan MALDI traces of YGL17108, YGL17177, YGLY22835, and YGLY17159 are shown in FIGS. 2A-D. The N-glycan profiles of mutants YGLY17172 and YGLY17178 are indistinguishable from that of mutant YGL17177.

Example 3

Recombinant Protein Expression in Mutant YGLY17159

Figure 3A:
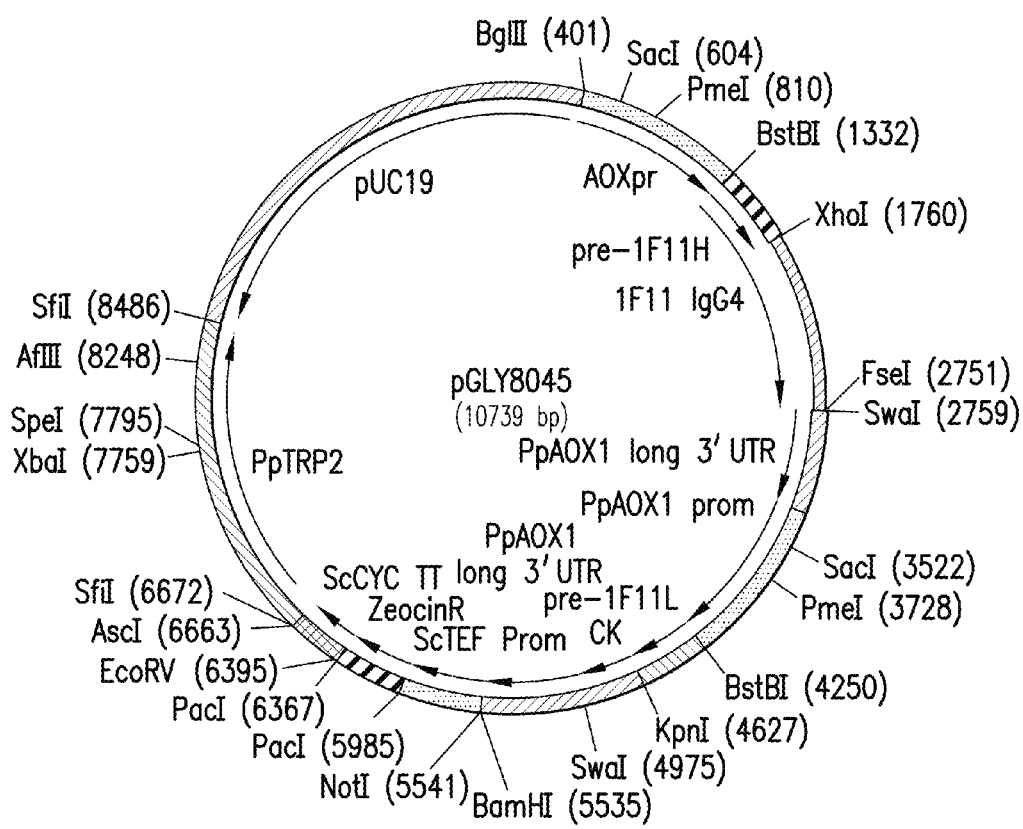
FIGS. 3A-B show plasmid maps of pGLY8045 and pGLY6391.
Figure 3B:
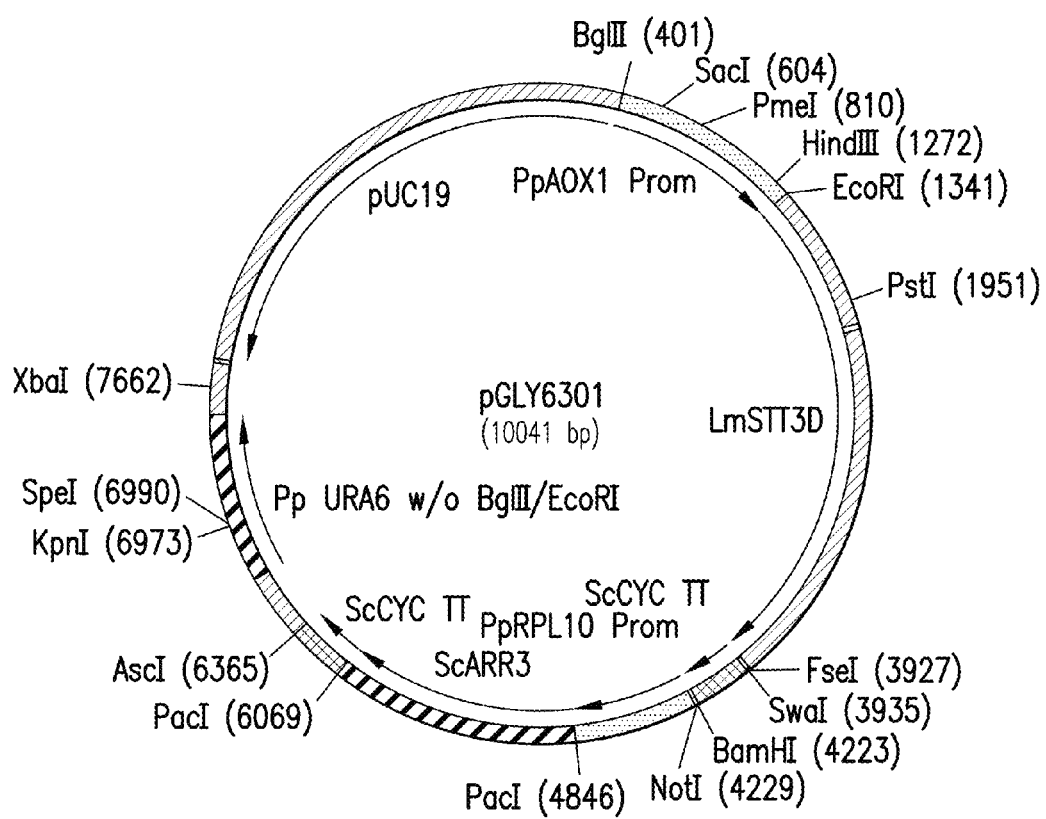

To illustrate that the increased fermentation robustness phenotype would be retained during recombinant protein production (e.g. heterologous protein production), two different recombinant proteins (an IgG4 mAb and an Fe-fusion protein) were transformed into mutant strain YGLY17159. The mAb-expressing strain was constructed by integrating the plasmid pGLY8045 (FIG. 3A), with both the 1F11 IgG4 heavy chain and kappa light chain under the control of the AOX1-promtor, into the TRP2 locus of YGLY17159 by electoporation. Similarly, the Fc-fusion expressing strain was generated by integrating the plasmid pGLY6391 (FIG. 3B), which harbored the AOX1p-driven TNFR-Fc fusion gene, into the THR1 locus of YGLY17159. After fermentation under standard platform conditions at 24° C. and 32° C. in 1 L DasGip bioreactors (Hopkins et al., 2011), the recombinant protein products secreted from both the parent and the mutant were purified and evaluated.

TABLE 3

Recombinant Product Expressions in the Mutant YGLY17159

| | | | Lysis during induction | | | | Broth titer @ harvest |
|---|---|---|---|---|---|---|---|
| | | | day 1 | day 2 | day 3 | day 4 | (mg/liter) |
| 1F11 IgG4 transformants in 1 L Bioreactor | | | | | | | |
| D104125 | 24 C. | y22835 parent | 0.5 | 3.5/4 | harvest | | 894 |
| D104129 | | y17159 mutant | 0.5/1 | 0.5 | 0.5/1 | 1.5 | 1813 |
| D104134 | 32 C. | y17159 mutant | 0.5 | 1 | 2.5 | h | 411 |
| TNFR Fc-fusion transformants in 1 L Bioreactor | | | | | | | |
| D104503 | 24 C. | y22835 parent | 0.5 | 3 | harvest | | 234 |
| D104501 | | y17159 mutant | 0.5 | 0.5/1 | 1 | 1.5/2 | 405 |
| D104511 | 32 C. | y22835 parent | 5* | harvest | | | |
| D104509 | | y17159 mutant | 0.5 | 1 | 1 | 2 | 188 |

*lysis score: 0-5, with 5 indicating the greatest amount of lysis (i.e. worst lysis)

The results in Table 3 illustrate that the recombinant protein expressing mutants retained superior robustness and extended strain stability during the induction period, which translated into significant product yield improvements, compared with these characteristics in the parent strain. At 24° C., the mutant strains exhibited about 100% titer increase for the IgG4 antibody, and about 70% titer increase for the Fe-fusion in the mutant strains compared to expression in the parental control cells under similar conditions.

Example 4

Confirmation of Phenotype by Directed Strain Engineering

Figure 5:
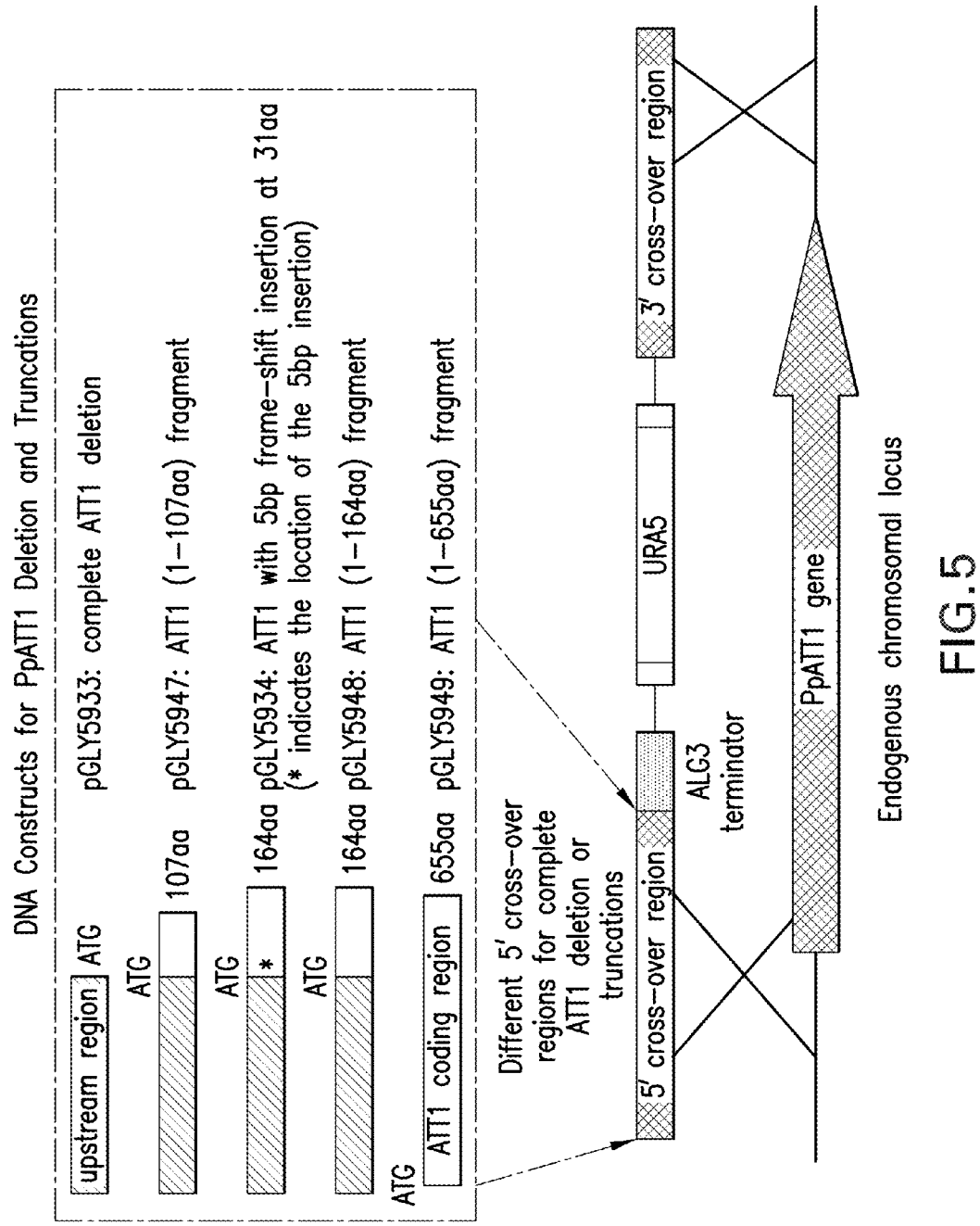
FIG. 5 shows the DNA constructs and integration strategy used to replace the endogenous ATT1 gene in non-mutagenized *Pichia* strains to test temperature-resistance and fermentation robustness phenotypes.

Independent mutations in the same gene in each of the mutants strongly indicated that truncations of this ATT1 transcription factor are responsible for the observed temperature-resistance and fermentation robustness phenotypes. To confirm this conclusion, the ATT1 ORF was either completely deleted, or the endogenous ATT1 gene was replaced with the truncated versions shown in FIG. 5, in YGLY21203, which is a non-mutagenized ura5 auxtroph *Pichia* strain derived from YGLY17108 by 5FOA counterselection.

Figure 4A:
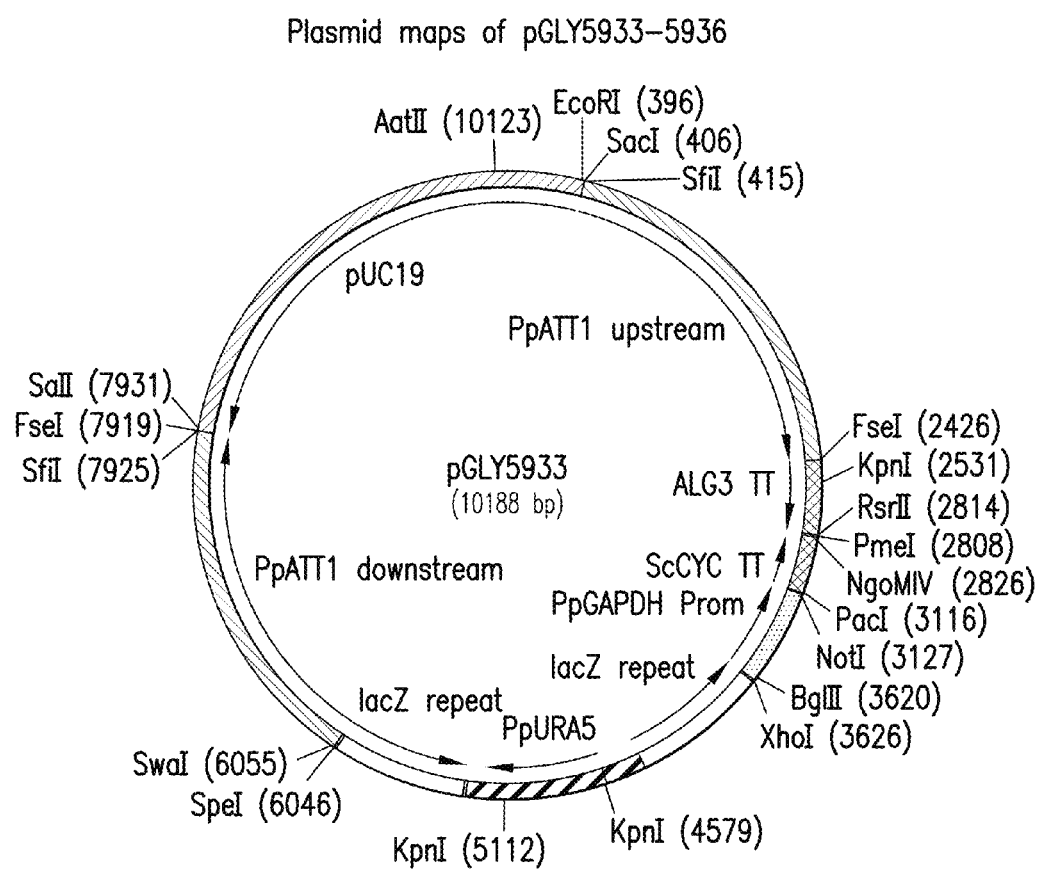
FIGS. 4A-G show plasmid maps of pGLY5933-5936 (FIGS. 4A-D, respectively) and pGLY5947-pGLY5949 (FIGS. 4E-G, respectively).

Plasmid pGLY5933 (FIG. 4A) was constructed by cloning a 2 kb genomic DNA fragment immediately upstream of the ATT1 ORF in front of the ALG3 terminator, followed by the lacZ-URA5-lacZ URAblaster, and then connected to a 1.9 kb genomic DNA fragment containing the last 285 bp of the ATT1 ORF (SEQ ID NO:1) plus 1.6 kb of the downstream region. After SfiI digestion, this ATT1-upstream-URA-blaster-ATT1-downstream DNA fragment was transformed into a non-mutagenized host strain (e.g. YGLY17108). By homologous recombination at both the ATT1 upstream and downstream regions, this URAblaster-cassette replaced the endogenous ATT1 gene, deleting 90% of ATT1's coding region, thus generating a complete ATT1 knock-out mutant. To confirm the correct replacement of the ATT1 ORF, genomic DNA polymerase chain reaction (PCR) assays were conducted using the following oligos as PCR primers: "TTTCGAAAGTGGCTTGGAAT" (SEQ ID NO:12, 2370 bp upstream of ATT1 start) and "TGGGGAGAAGGTAC-CGAAAG" (SEQ ID NO:13, within the ALG3 terminator) to confirm the 5' junction of the gene-replacement; "CAC-TACGCGTACTGTGAGCC" (SEQ ID NO:14, within the lacZ) and "GCTTGGTACGGTAGCCTCAA" (SEQ ID NO:15, 2014 bp downstream of the ATT1 stop codon) to confirm the 3' junction of the gene-replacement; plus "AGTCTGCGCTTTCCATGTCT" (SEQ ID NO:16, 365 bp upstream of the ATT1 start) and "GGCCTGGAGATATTGG-GATT" (SEQ ID NO:17, within the ATT1 ORF, 1070 bp after the start) to confirm the absence of the wild-type ATT1 ORF.

Figure 4B:
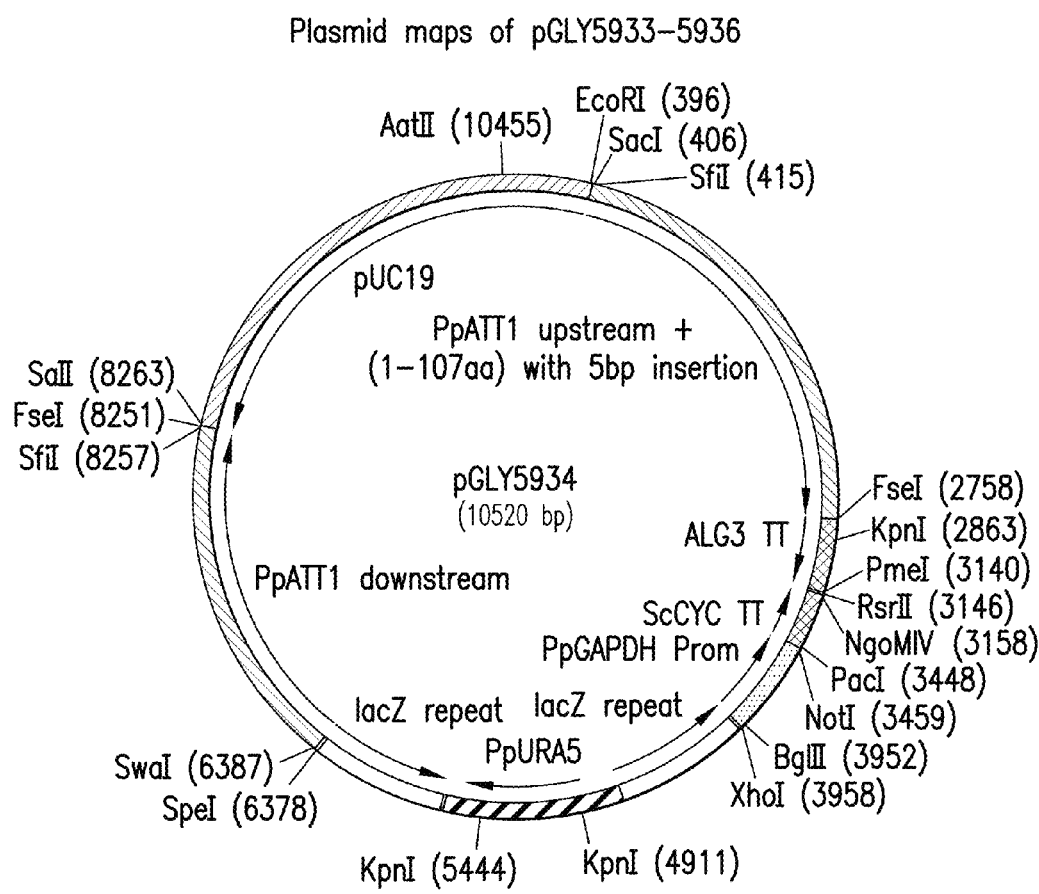
Figure 4C:
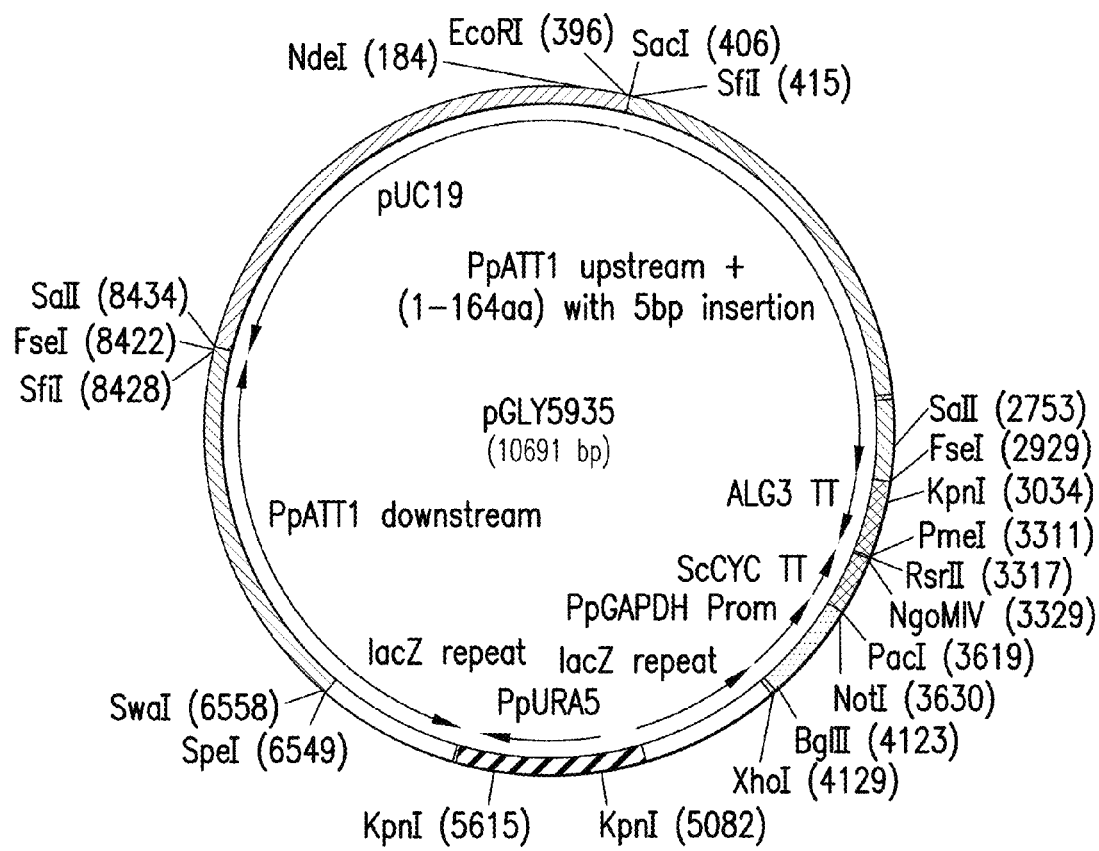
Figure 4D:
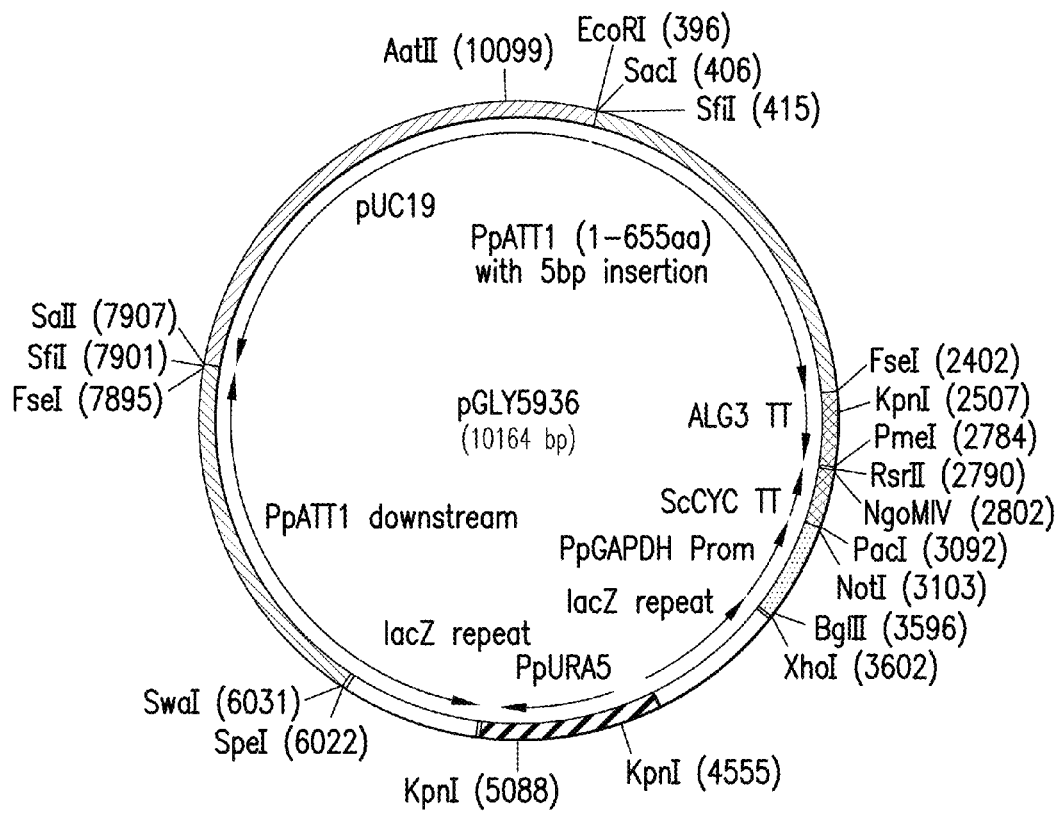
Figure 4E:
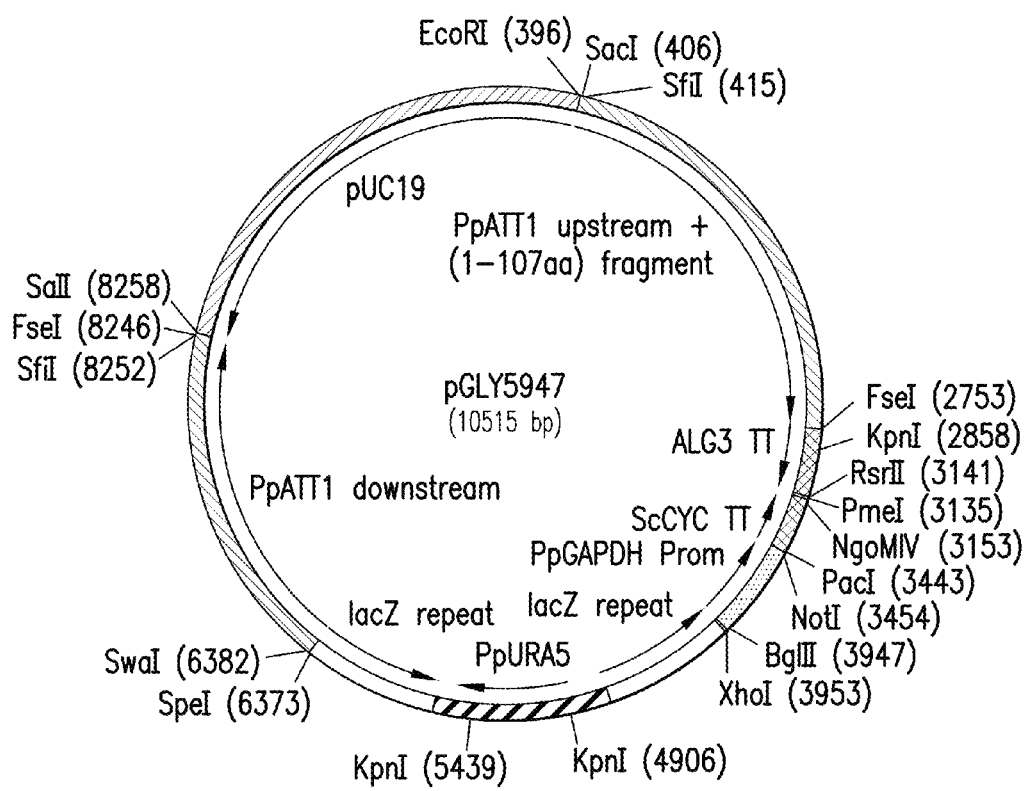

Plasmid pGLY5947 (FIG. 4E) was constructed by cloning a 2.3 kb DNA fragment (2.0 kb upstream region, the 1st 321 bp of the ATT1 ORF, plus 2 stop codons) in front of the ALG3 terminator sequence, followed by the lacZ-URA5-lacZ URAblaster, and then connected to a 1.9 kb genomic DNA fragment containing the last 285 bp of the ATT1 ORF plus 1.6 kb of the downstream region.

Figure 4F:
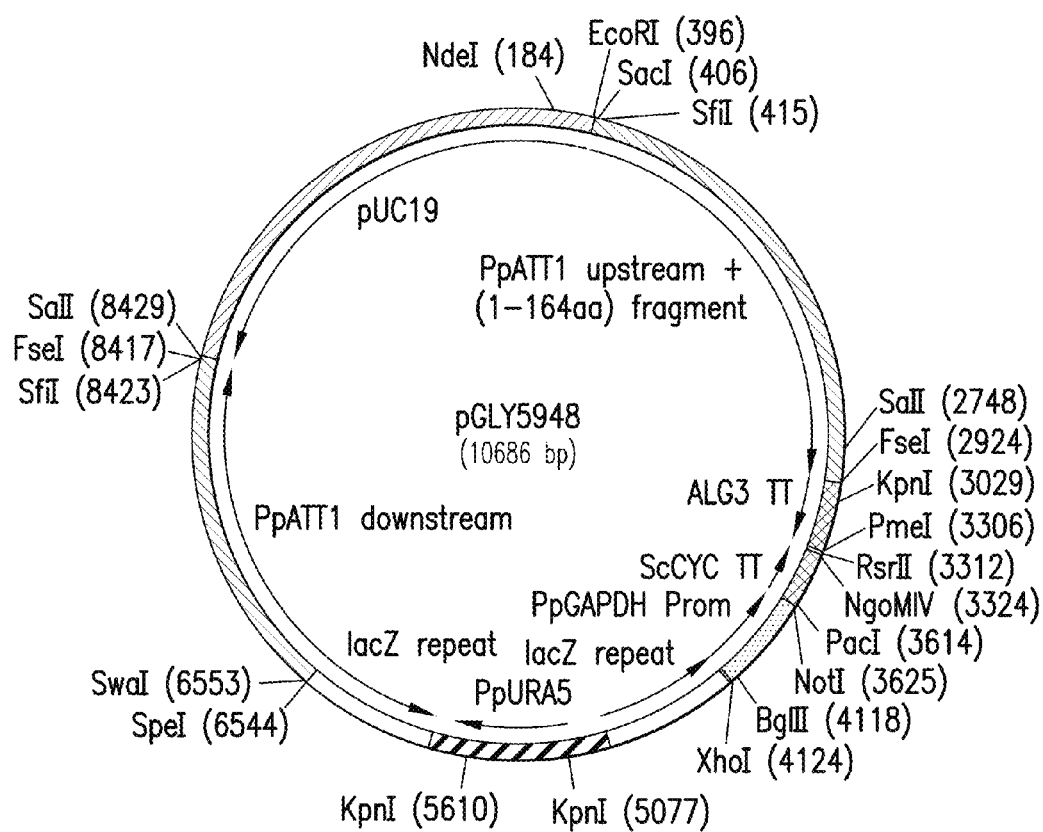
Figure 4G:
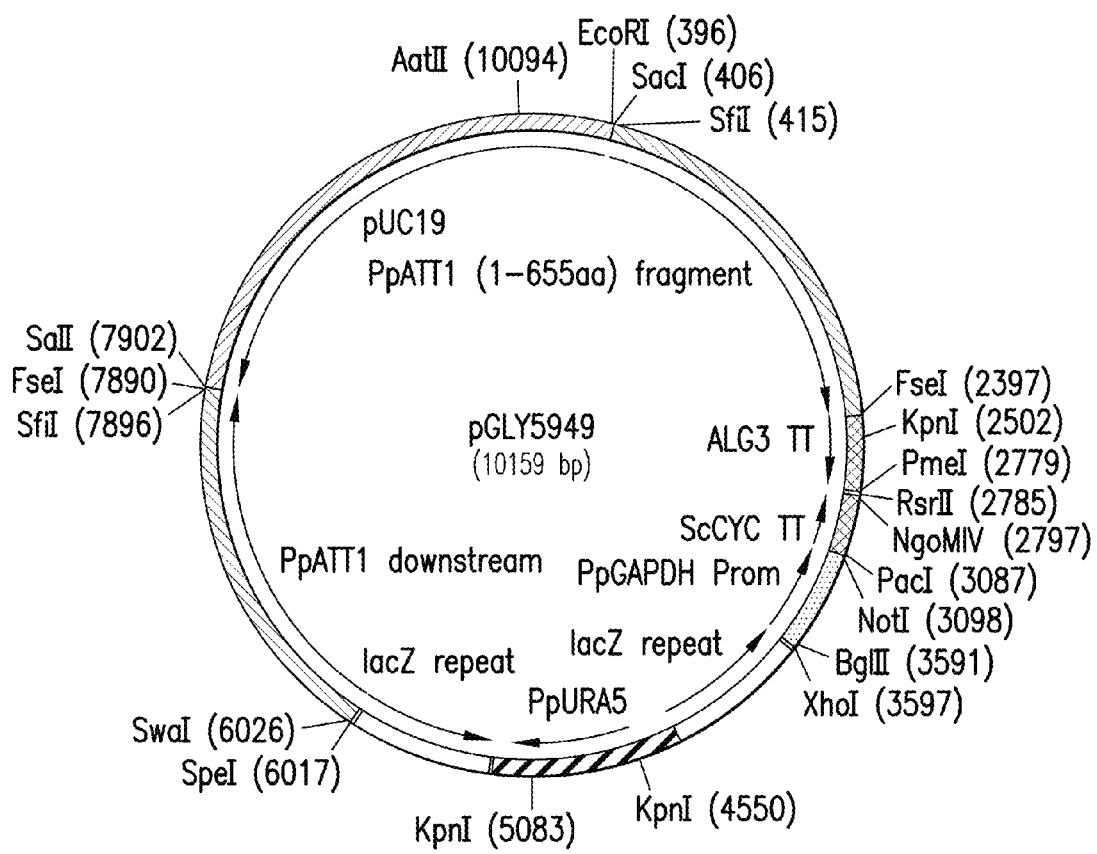

Homologous recombination-mediated double-crossovers between the SfiI-fragment of pGLY5947 (FIG. 4E) and the chromosomal ATT1 region replaced the endogenous ATT1 ORF with a truncated version of ATT1 with only the first 107 amino acid residues. Similarly, plasmid pGLY5948 (FIG. 4F) and pGLY5949 (FIG. 4G) contain the first 492 bp or 1965 bp of the ATT1 ORF (SEQ ID NO:1) respectively, and homologous recombination-mediated double-crossovers would replace the endogenous ATT1 ORF with a truncated region of ATT1 encoding the truncations 1-164 (SEQ ID NO:10) or 1-655 amino acids (SEQ ID NO: 11).

Plasmid pGLY5934 (FIG. 4B) is almost identical to pGLY5947, except that it also contains a 5 bp (TGAATC, SEQ ID NO:18) frame-shift insertion after the 31st amino acid residue of the ATT1 ORF; and plasmid pGLY5935 (FIG. 4C) is almost identical to pGL5948 (FIG. 4F), except that it contains the same 5 bp (TGAATC, SEQ ID NO:18) frame-shift insertion after the 31st amino acid of ATT1 (SEQ ID NO:7), coding for the ATT1 fragment SEQ ID NO:8.

Figure 6A:
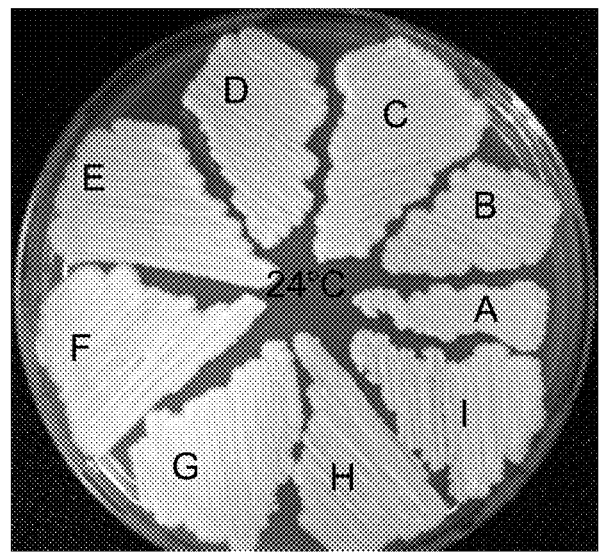
Figure 6B:
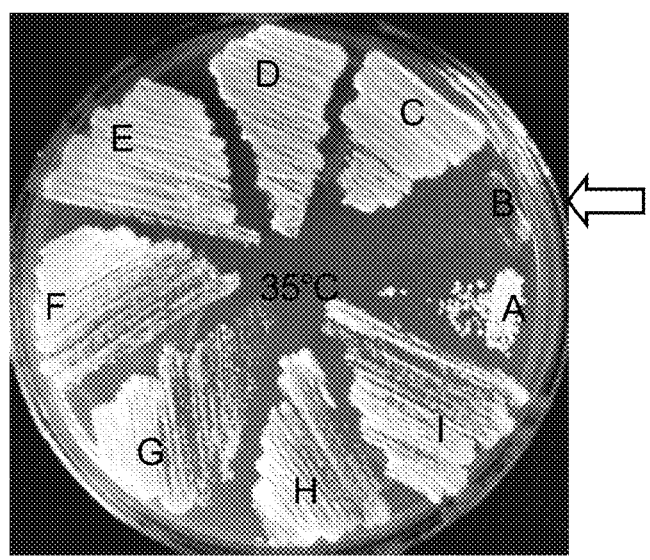

After confirming the DNA constructs precisely replaced the endogenous ATT1 gene with the corresponding deletion or truncations, their abilities to grow at 35° C. was examined. It was confirmed that these ATT1Δ truncation and deletion mutants displayed temperature-resistant phenotypes very similar to those observed from the original mutants isolated by UV mutagenesis (FIGS. 6A-C).

Next, the truncation and deletion mutants were subjected to standard DasGip MeOH fed-batch fermentation runs (Hopkins et al., 2011) to determine whether they would also display increased fermentation robustness. In order to determine the fermentation robustness of these strains, their lysis scores were measured after determined periods of induction at 32° C. A lysis score of 0.5-5.0 was assigned based on microcopic examination. A lysis score of 0.5 indicates minimal lysis (more than 95% intact cells), and a lysis score of 5 indicates high lysis (less than 10% intact cells). As observed previously, the YGLY17108 control strain displayed heavy lysis and was not viable within 24 hours of MeOH induction at 32° C. In contrast, the strains harboring the complete deletion and various truncations of the ATT1 gene showed a remarkable increase in fermentation robustness and successfully completed 4 days of MeOH induction (Table 4). The ATT1 (1-164aa, SEQ ID NO:10) and ATT1 (1-655aa, SEQ ID NO:11) truncation mutants displayed slightly higher degrees of cell lysis (lysis score of 2.5 or 3) during the later stages of the induction phase (see Table 3). Strains containing the complete deletion and the ATT1 frame-shift (5 bp insertion at 31aa) mutant displayed the highest level of fermentation robustness, with lysis scores of 0.5 throughout the 4 day induction phase. The finding that the strain harboring the 5 bp insertion at 31aa exhibited the same robustness as the ATT1 deletion mutant indicated that the 5 bp frame-shift mutation likely results in the complete disruption of the function of ATT1 gene product. On the other hand, the ATT1 (1-164aa, SEQ ID NO:10, encoded by SEQ ID NO:4) and ATT1 (1-655aa, SEQ ID NO:11, encoded by SEQ ID NO:5) truncated forms of ATT1 might still retain some residual levels of transcriptional activity, because mutants harboring these truncations displayed an intermediate phenotype: dramatically more robust than the parental control, but not as strong as that of the deletion mutant. The phenotypes exhibited by these directed gene-replacement strains closely resembled those displayed by the corresponding UV-induced mutants (for example, compare YGL27601 with YGL17159; YGLY27608 with YGL17177; YGLY27610 with YGLY17172 in Table 4 and FIGS. 6A-C), illustrating that the mutations within the ATT1 gene were responsible for the improved thermal tolerance and fermentation robustness observed from the UV-induced mutants.

TABLE 4

Lysis scores of parental controls compared to PpATT1 deletion and truncation strains fermented at 32° C.

| 1 L Bioreactor MeOH | | Lysis @ 32 C. | | | |
|---|---|---|---|---|---|
| Induction Phase | | Day 1 | Day 2 | Day 3 | Day 4 |
| YGLY17108 | empty parent control | 5* | | harvest | |
| YGLY27611 | ATT1 complete KO | 0.5 | 0.5 | 0.5 | 0.5 |

TABLE 4-continued

Lysis scores of parental controls compared to PpATT1 deletion and truncation strains fermented at 32° C.

| 1 L Bioreactor MeOH | | Lysis @ 32 C. | | | |
|---|---|---|---|---|---|
| Induction Phase | | Day 1 | Day 2 | Day 3 | Day 4 |
| YGLY27601 | ATT1 w/5 bp insertion @ 31 aa | 0.5 | 0.5 | 0.5 | 0.5 |
| YGLY27624 | ATT1 w/5 bp insertion @ 31 aa | 0.5 | 1 | 1/1.5 | 1/1.5 |
| YGLY27630 | ATT1 (1-164aa) fragment | 0.5 | 0.5 | 0.5 | 0.5 |
| YGLY27608 | ATT1 (1-164aa) fragment | 0.5/1 | 1 | 1/1.5 | 2 |
| YGLY27610 | ATT1 (1-655aa) fragment | 0.5/1 | 1/1.5 | 2/2.5 | 3 |
| YGLY27633 | ATT1 (1-655aa) fragment | 0.5 | 1.5 | 1.5/2 | 3 |

*lysis score: 0-5, with 5 indicating the greatest amount of lysis (i.e. worst lysis)

Example 5

Figure 10:
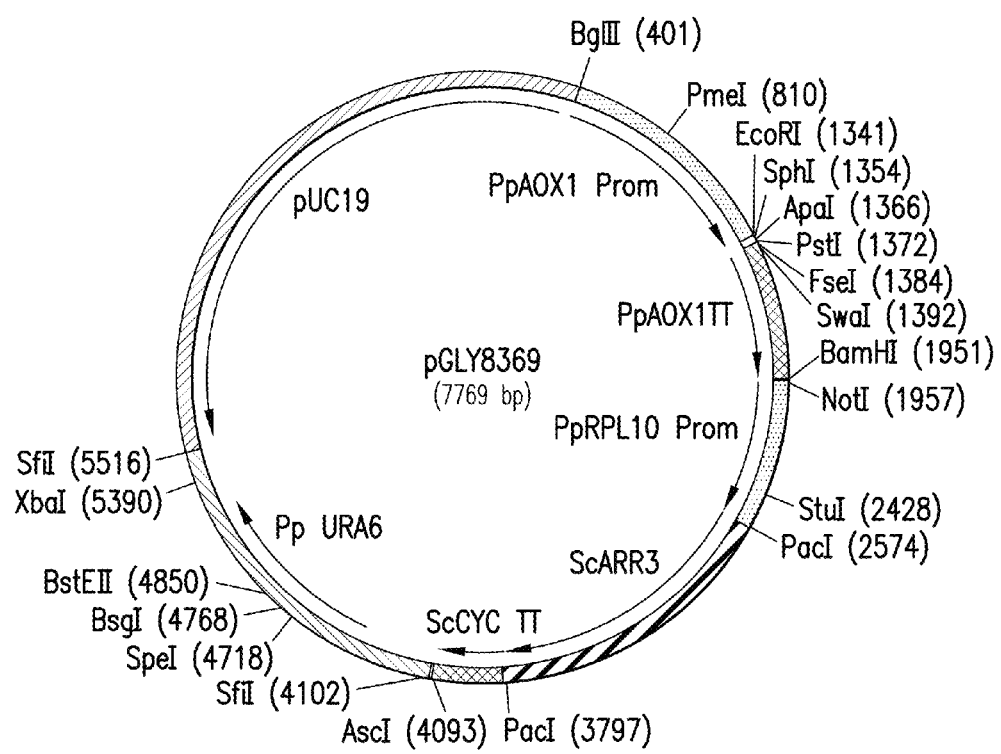
FIG. 10 shows a plasmid map of pGLY8369.
Figure 11:
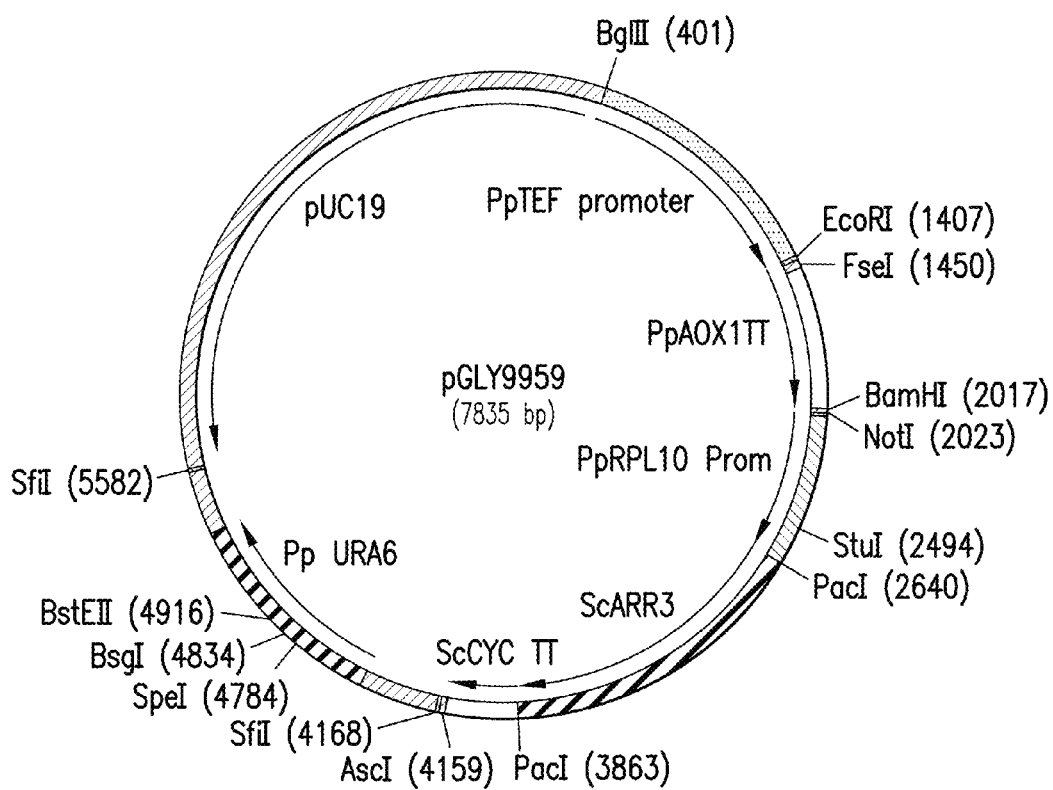
FIG. 11 shows a plasmid map of pGLY9959.
Figure 14A:
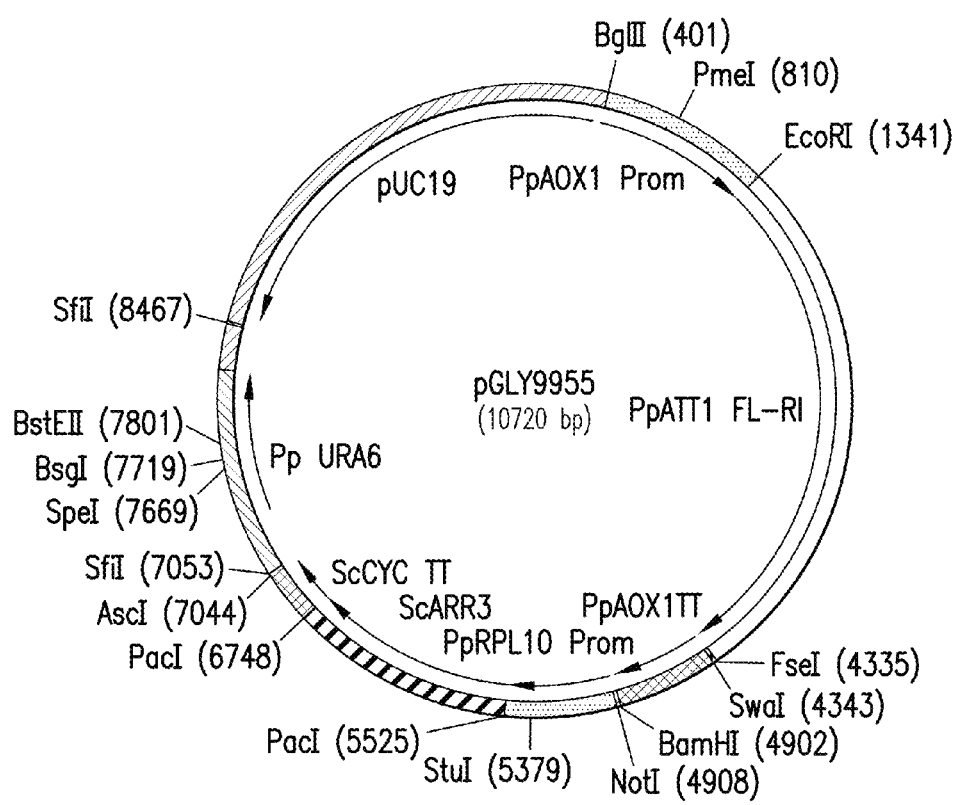
FIGS. 14A-H show plasmid maps. FIGS. A4A-D show plasmid maps of pGLY9955-pGLY9958, respectively.
Figure 14B:
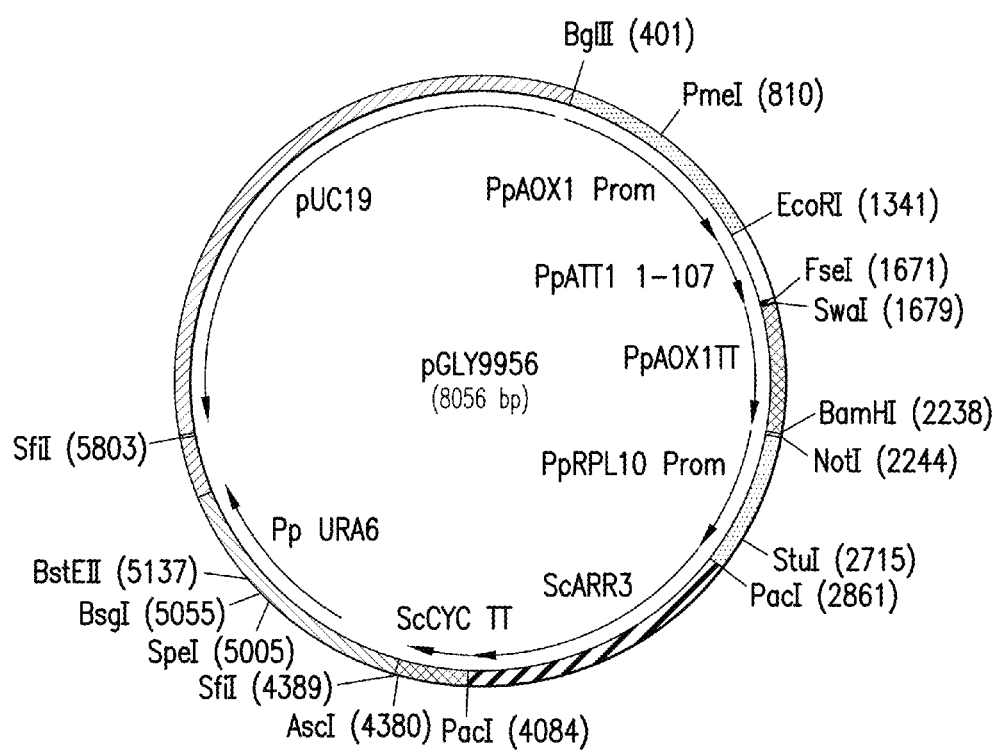
Figure 14C:
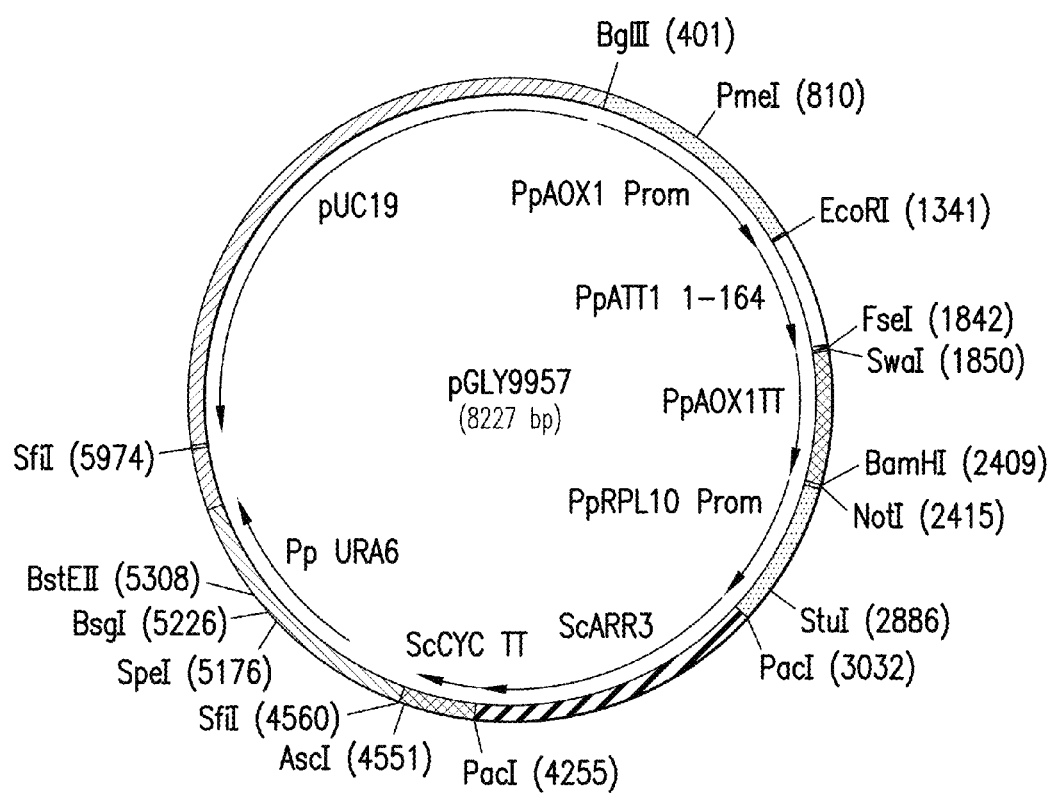
Figure 14D:
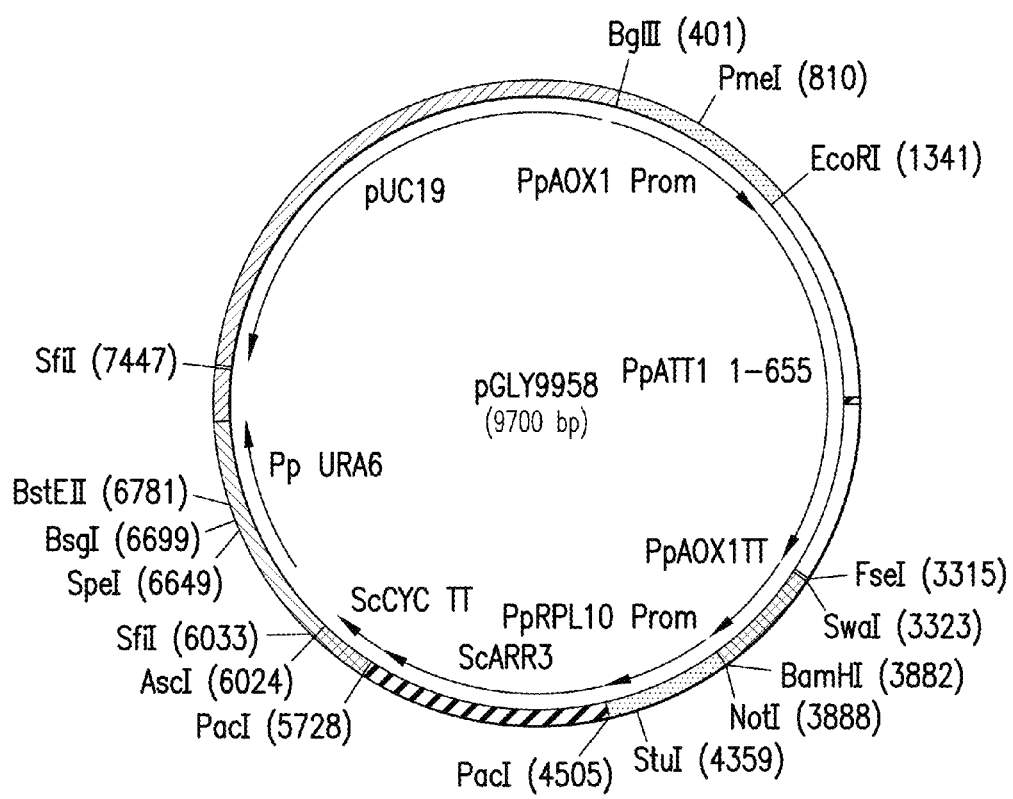
Figure 14E:
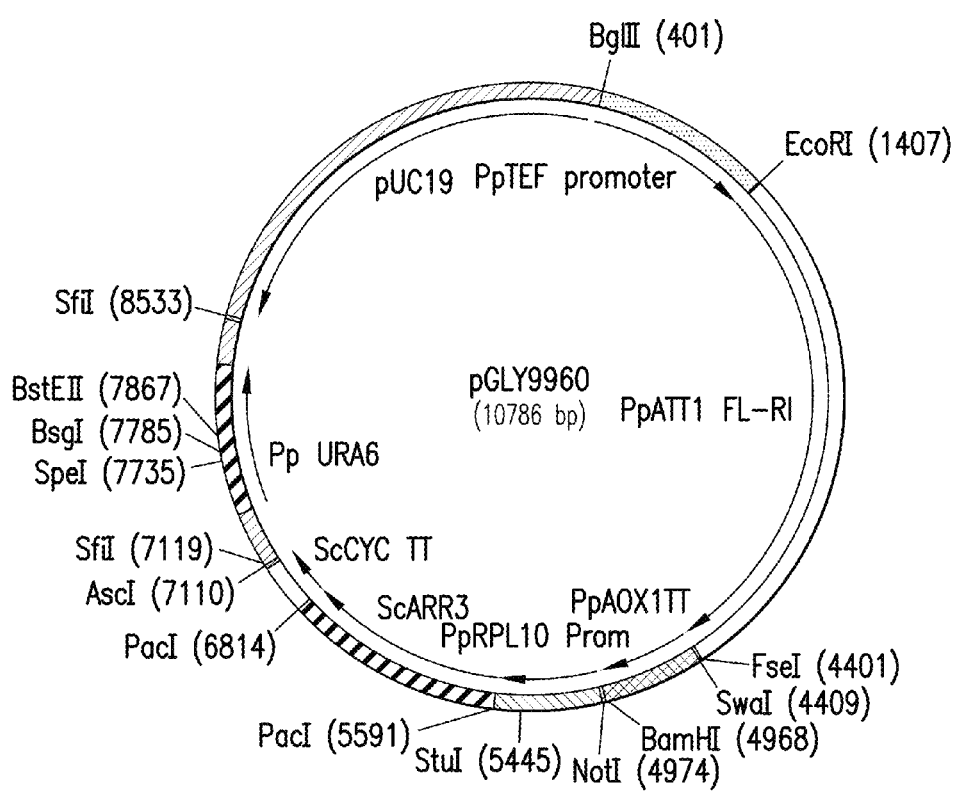
Figure 14F:
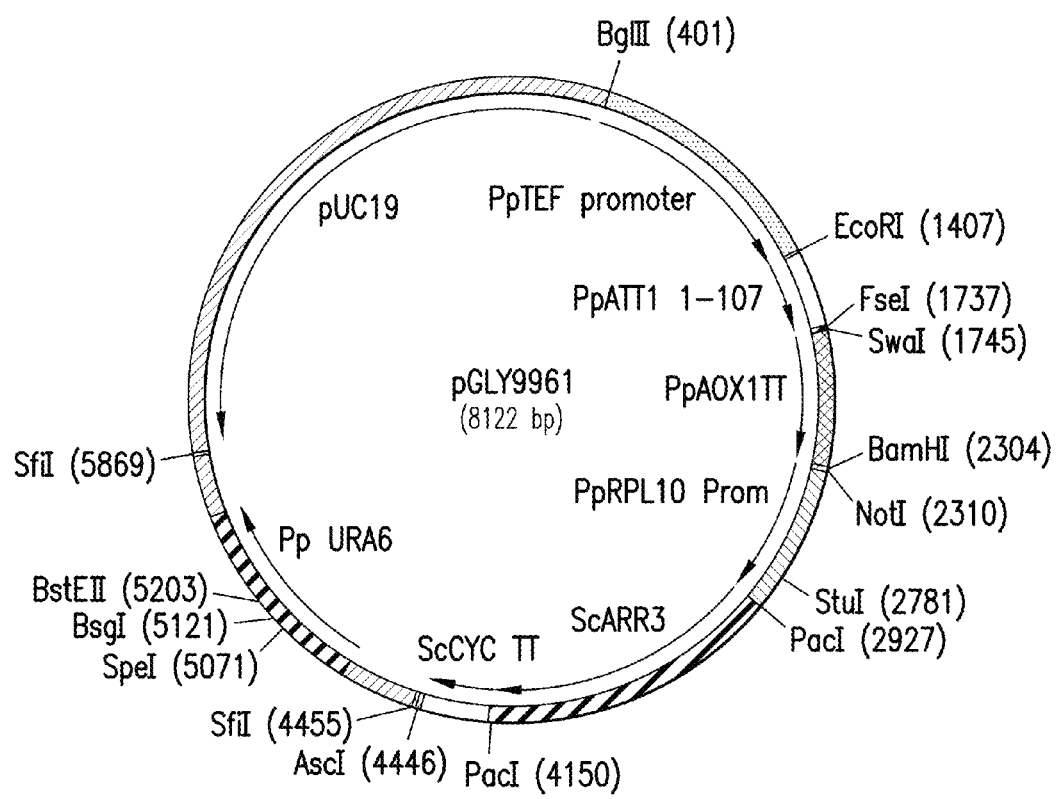
Figure 14G:
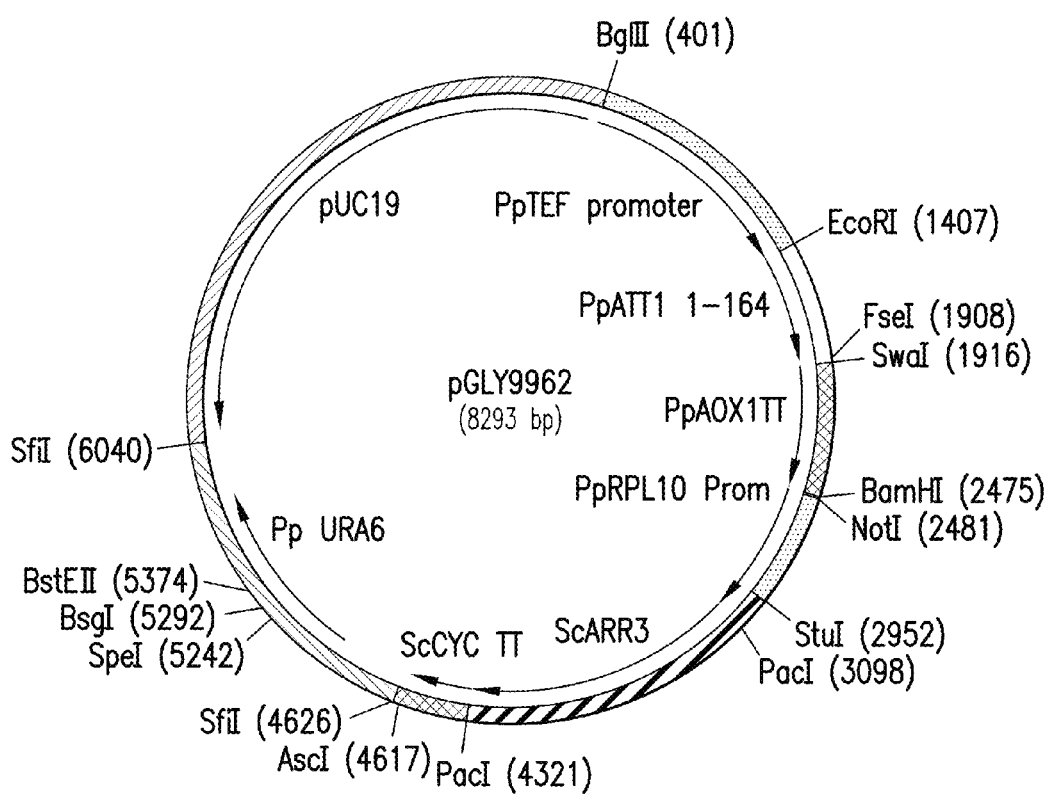
Figure 14H:
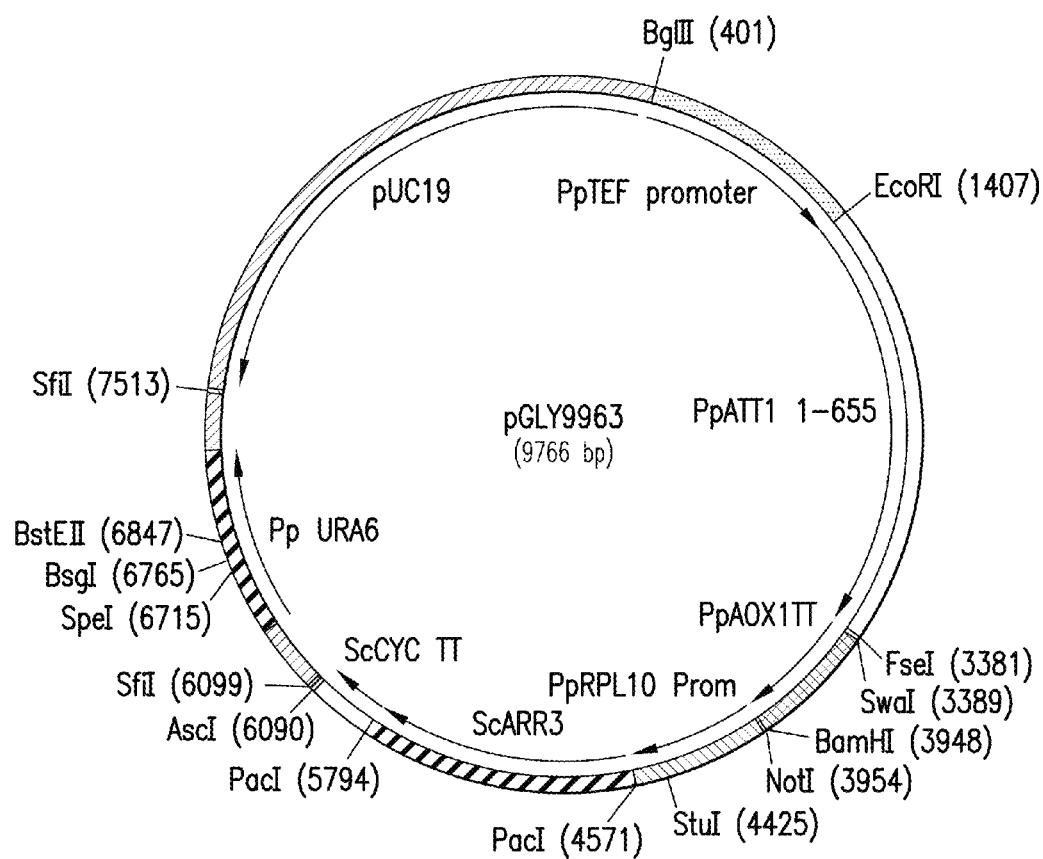

Construction of Plasmids to Overexpress the *P. pastoris* ATT1 ORF and Truncated Alleles The *P. pastoris* TEF promoter (SEQ ID NO: 6) was synthesized using oligonucleotides and manufacturer's methods as described by Genscript (Piscataway, N.J.) and cloned into the plasmid, pGLY8369 (FIG. 10) using the restriction sites BglII/EcoRI to generate plasmid pGLY9959 (FIG. 11). Plasmid pGLY8369 is a roll-in *Escherichia coli/P. pastoris* shuttle plasmid that contains the *P. pastoris* AOX1 promoter and the *S. cerevisiae* ARR3 gene as a selectable marker, which confers resistance to arsenite. The *P. pastoris* wild type ATT1 open reading frame (Pp01g00680, SEQ ID NO:1) was synthesized using oligonucleotides by Genscript and manufacturer's methods, and inserted into pGLY8369 (FIG. 10) and pGLY9959 (FIG. 11) using restriction sites EcoRI/FseI to generate plasmids pGLY9955 (FIG. 14A) and pGLY9960 (FIG. 14E), respectively. Truncated versions or fragments of ATT1 encoding the first 107 amino acids (1-107 aa, SEQ ID NO:3) of SEQ ID NO:7, the first 164 amino acids (1-164 aa, SEQ ID NO:4) of SEQ ID NO:7 and the first 655 amino acids (1-655 aa, SEQ ID NO:5) of SEQ ID NO:7 were subsequently generated from pGLY9955 (FIG. 14A) to yield the AOX1-driven ATT1 truncated allele containing plasmids, named pGLY9956 (FIG. 14B), pGLY9957 (FIG. 14C), pGLY9958 (FIG. 14D), respectively, and from pGLY9960 (FIG. 14E) to yield the TEF-driven ATT1 truncated allele containing plasmids, named pGLY9961 (FIG. 14F), pGLY9962 (FIG. 14G), pGLY9963 (FIG. 14H), respectively.

Example 6

Figure 12:
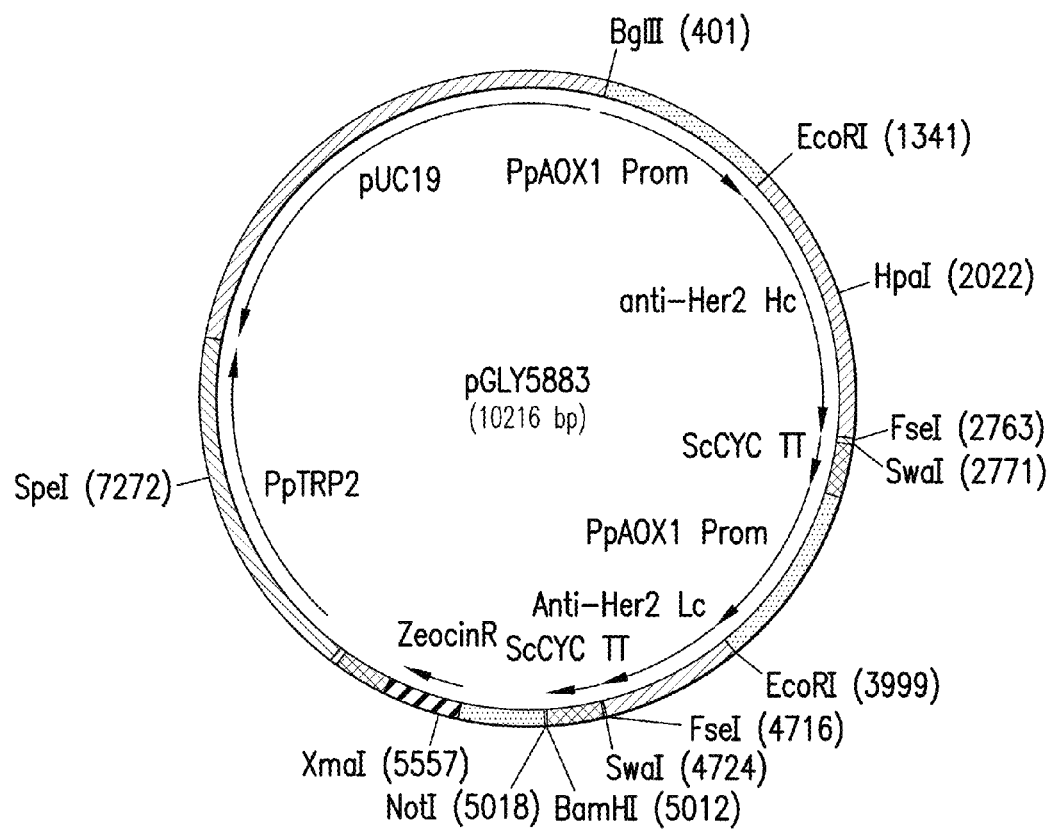
FIG. 12 shows a plasmid map of pGLY5883.

Generation of an Anti-Her2 Monoclonal Antibody in Glyco-Engineered *P. pastoris* Strains Plasmid pGLY5883 was generated by fusing DNA sequences encoding the κ and γ chains of the Trastuzumab anti-HER2 monoclonal antibody (Carter, 1992) individually to the *P. pastoris* AOX1 promoter and is depicted in FIG. 12. DNA from this plasmid was digested with SpeI to linearize the DNA and was transformed by standard electroporation methods (*Pichia* kit, Invitrogen, Carlsbad, Calif.) into the *P. pastoris* glyco-engineered strain YGLY8316, which has been modified to produce complex-type human N-glycans with terminal β-1,4-galactose (described as GFI5.0; Davidson U.S. Pat. No. 7,795,002) (strain lineage shown in FIG. 13). Clones were selected on medium containing Zeocin and further screened by standard cultivation in 96 deep well plates and 0.5 L Sixfors multifermentation fermenters (ATR Biotech, Laurel, Md.; Barnard, 2010). One positive expression clone was picked and named YGLY13979 (strain lineage shown in FIG. 13).

Example 7

Over-Expression of the *P. pastoris* ATT1 Open Reading Frame and Truncated Alleles Leads to Improved Strain Survival and Protein Titer Plasmids pGLY9955, pGLY9956, pGLY9957, pGLY9958, pGLY9960, pGLY9961, pGLY9962, and pGLY9963 (FIGS. 14A-H, respectively) were linearized with SpeI and transformed by electroporation (*Pichia* kit, Invitrogen, Carlsbad, Calif.) into strain YGLY13979 and clones were selected on YSD medium containing 1 mM and 3 mM sodium arsenite. Clones that overexpress the full length and various truncations of ATT1 were further isolated on YSD media and then confirmed to contain the desired ATT1 expression constructs by PCR using primers RCD1019 (SEQ ID NO:19 5'-CAGATCTTCCAACATTCGTACACG-3') and AOX1seq (SEQ ID NO:20 5'-GCTTACTTTCATAATTGC-GACTGGTTCC-3') for the AOX1-driven constructs and RCD1019 and TEFseq (SEQ ID NO:21 5'CGCAGTCCCA-CACGCACTCGTACATG-3') for the TEF-driven constructs.

Figure 13:
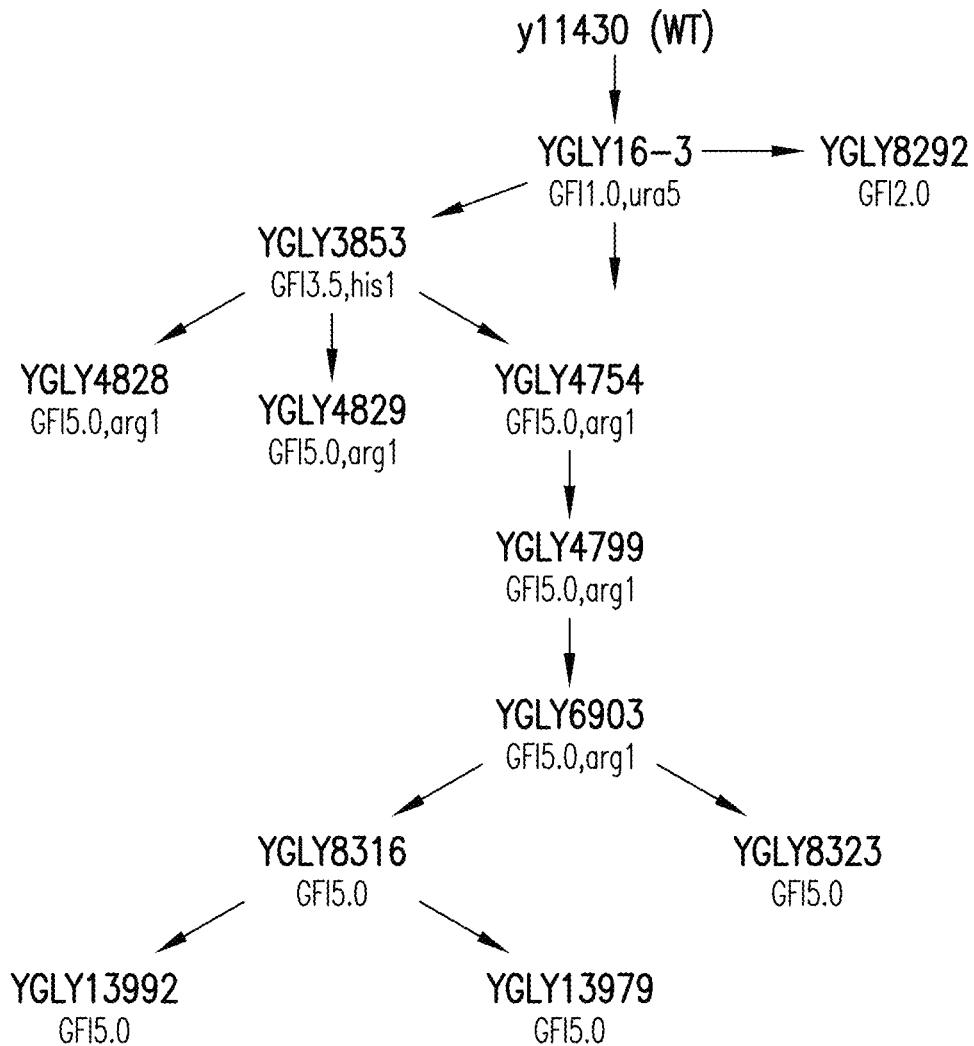
FIG. 13 shows strain lineages from NRRL 11430 through yGLY13979.

PCR positive clones were selected and cultivated in a modified version of an Applikon (Foster City, Calif.) micro24 5 ml mini-fermenter apparatus, along with the parental strain YGLY13979 (FIG. 13, also expressing the same anti-HER2 mAb). Seed cultures were prepared by inoculating strains from YSD plates to a Whatman 24-well Uniplate (10 ml, natural polypropylene) containing 3.5 ml of 4% BMGY medium (Invitrogen, Carlsbad, Calif.) buffered to pH 6.0 with potassium phosphate buffer. The seed cultures were grown for approximately 65-72 hours in a temperature controlled shaker at 24° C. and 650 rpm agitation. One milliliter of the 24 well plate grown seed culture and 4.0 ml of 4% BMGY medium was then used to inoculate each well of a Micro24 plate (Type: REG2). Thirty microliters of Antifoam 204 (1:25 dilution, Sigma Aldrich) was added to each well. The Micro24 was operated in Microaerobic 1 mode and the fermentations were controlled at 200% dissolved oxygen, pH at 6.5, temperature at 24° C. and agitation at 800 rpm. The induction phase was initiated upon observance of a dissolved oxygen (DO) spike after the growth phase by adding bolus shots of methanol feed solution (100% [w/w] methanol, 5 mg/l biotin and 12.5 ml/1 PTM2 salts), 50 μl in the morning and 125 μl in the afternoon. After approximately 72 hours of methanol induction, the cell-free culture supernatant was harvested by centrifugation at 2500×g in a Beckman swinging bucket centrifuge and subjected to protein A purification by standard methods (Jiang, 2011). Antibody was quantified by reverse phase HPLC and calculated on a per liter basis. Supernatant was also subjected to the Picogreen (Invitrogen, Carlsbad, Ca) double stranded DNA quantification assay as a method to quantitatively measure cell breakage or lysis.

Figure 15:
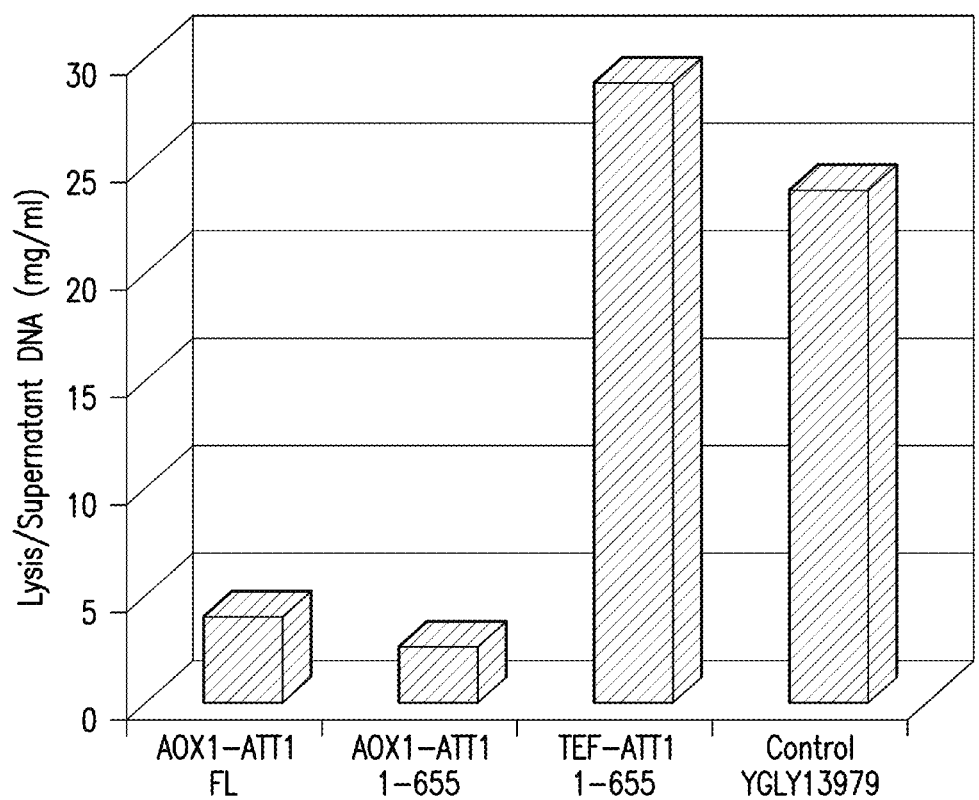
FIG. 15 shows a graph illustrating reduced lysis for *Pichia* strains with ATT1 deletions.
Figure 16:
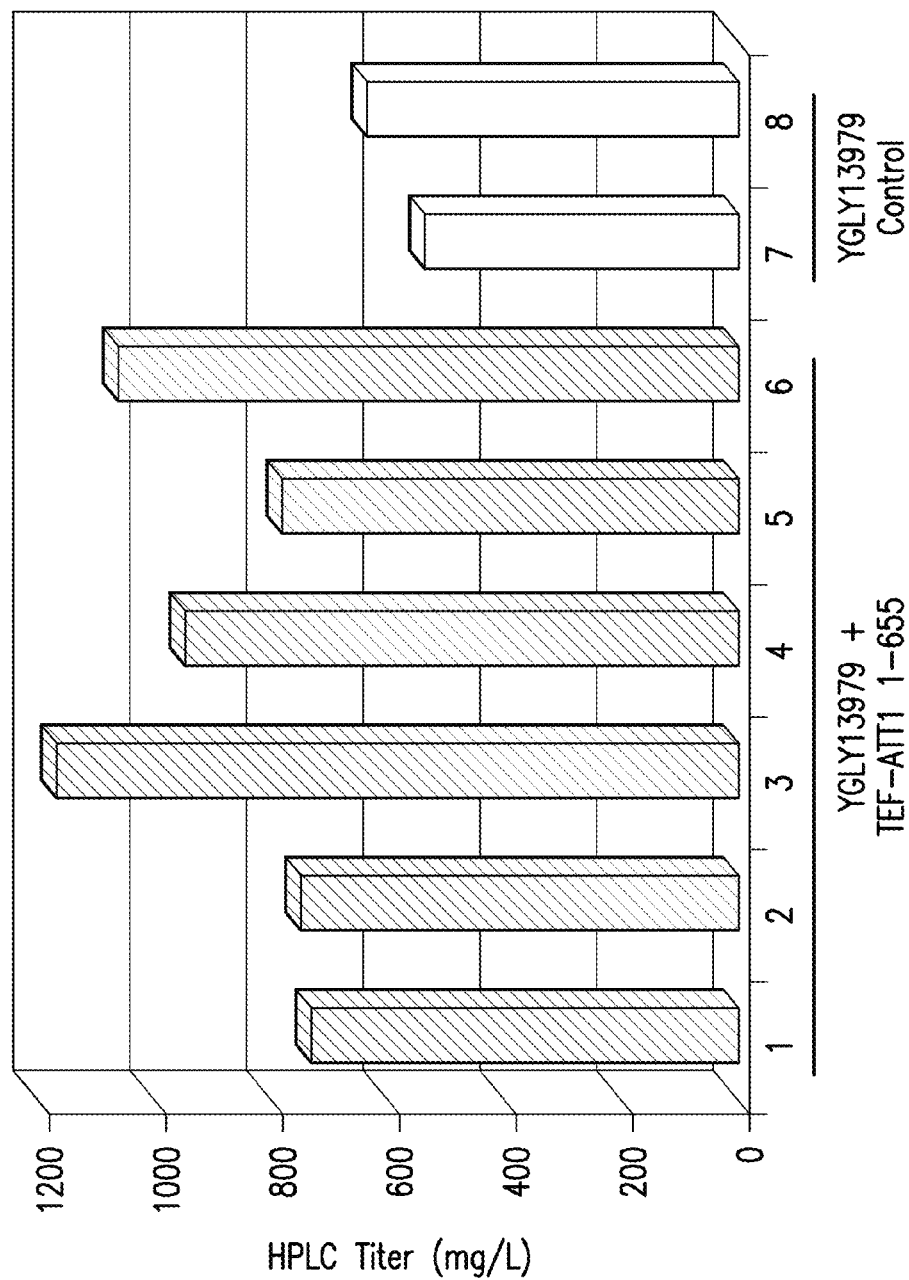
FIG. 16 shows a graph illustrating protein titer for the *Pichia* ATT1 over-expression strain yGLY13979+TEF-ATT1 1-655.

In an experiment comparing over expression of the wild-type full length ATT1 vs. the 1-655aa ATT1 truncation, six clones of each were evaluated, including TEF and AOX1 promoter versions of the 1-655 ATT1 truncation. Two of the six wild-type ATT1 over-expression strains produced significantly more antibody than the YGLY13979 control strains (FIG. 16). The control strains produced 587.5+/−70 mg/L of antibody whereas two AOX1-ATT1 full length over-expression strains produced 806 and 934 mg/L, respectively (FIG. 16). Similarly two of the AOX1-ATT1 1-655 over-expression strains also produced significantly more secreted mAb, with 906 and 1098 mg/L, respectively. Moreover, in all of the AOX1-ATT1 full length and AOX1-ATT1 1-655 over-expression strains, the lysis, as determined by picogreen assay, was reduced compared to the control strains (FIG. 15). Finally, when the 1-655 ATT1 truncation was expressed under control of the TEF promoter, lysis was unaffected or potentially increased (FIG. 15), while all of the clones still produced increased levels of secreted mAb (FIGS. 16-17).

Example 8

Impact of ATT1 Full-Length Over-Expression on Protein Productivity and Lysis is Scalable The impact of over-expression of the ATT1 full length ORF on antibody productivity can be demonstrated clearly in microfermentation models. However, these models differ from full scale fermentation cultivation in several key aspects, including vessel size, shear and oxidative stress on the cells, and method of carbon source feed (bolus versus limiting or excess feed). To demonstrate the scalability of the ATT1 over-expression, six *Pichia* strains over-expressing ATT1 full length ORF (denoted as FL): (YGLY27927, YGLY27928, YGLY27929, YGLY27930, YGLY27931, and YGLY27932) along with the parental (YGLY13979) and ATT1 knockout (YGLY27638) control anti-HER2 expressing strains were cultured in 1 L Fedbatch Pro fermenters (DASGIP Biotools, Shrewsbury, Mass.) using a glycerol feedbatch followed by limiting-methanol feed induction process at 24° C. as previously described (Hopkins et al., 2011). Methanol induction was continued until lysis was too severe to continue for each strain (up to 113 h), after which the cell-free culture supernatant was harvested by centrifugation at 2500×g in a Beckman swinging bucket centrifuge and subjected to protein A purification by standard methods (Jiang, 2011). Antibody was quantified by reverse phase HPLC and calculated on a per liter basis. The YGLY13979 parental control strain produced 671 mg/L of secreted mAb but with very high lysis after 66 h of induction (FIG. 17).

In contrast, the ATT1 knockout strain produced 1256 mg/L in 106 h of induction with minimal lysis (FIG. 17), consistent with previous results. Similarly, and consistent with smaller scale micro24 fermentation results, two AOX1-ATT1 over-expressing clones produced 1974 and 1960 mg/L, respectively, in 112 h of induction, surprisingly demonstrating that over-expression of the ATT1 ORF can positively affect robustness and productivity in extended induction at larger scale (FIG. 17). Additionally, three of the six ATT1 over-expressing clones displayed reduced lysis compared to the YGLY13979 control while another clone only exhibited lysis after more than 100 h of induction (FIG. 17). These results demonstrate that the impact of the ATT1 over-expression on mAb productivity in recombinant protein-producing *Pichia* strains is independent of scale and is not affected by standard variations in culture and induction protocols.

To further illustrate the impact of the AOX-ATT1 over-expression on glyco-engineered strain robustness, the two high mAb expression strains, YGLY27929 and YGLY27930 were cultivated again in the same 1 L Fedbatch Pro fermenters using the same protocol but at 32° C. instead of 24° C. Based on previous experiments, the parental strain, YGLY13979, is not capable of fermentation at elevated temperature, with a complete loss due to foaming and severe cell lysis typically occurring 24-48 h into methanol induction. After 50 h of methanol induction at 32° C. the two over-expression strains YGLY27929 and YGLY27930 produced 473 and 458 mg/L of anti-HER2 mAb compared to 842 mg/L for the ATT1 knockout strain (in 73 hours of induction). Lysis of the over-expression strains was slightly elevated compared to the ATT1 knockout strain, but survival to 50 h of induction with moderate lysis represents a significant improvement over the parental glyco-engineered anti-HER2 expressing strain, and demonstrates the utility of over-expression of ATT1 in addition to deletion/truncation of this gene.

Strains described in Examples 6 to 8 all have the chromosomal copy of ATT1 still intact. Over-expression of full-length ATT1 or ATT1 truncations (both AOX1- and TEF-promoter driven) in strains with their endogenous ATT1 ORF deleted are expected to produce similar improvements in cell robustness and productivity as shown in Examples 6 to 8.

Example 9

*Hansenula polymorpha* ATT1 Ortholog Functionally Complements the ATT1 Null Mutation in *Pichia pastoris*

The *H. polymorpha* ATT1 ortholog (GenBank EFW98022.1) was identified by performing BLAST sequence similarity search against the GenBank non-redundant protein database. FIG. 18 shows an alignment of *S. cerevisiae* Gal4, *P. pastoris* ATT1 and *H. polymorpha* ATT1.

*H. polymorpha*, also as known as *Ogataea parapolymorpha* or *Pichia angusta*, is a methylotrophic yeast commonly used for expressing heterologous recombinant proteins. Similar to *P. pastoris*, *H. polymorpha* also has lost its ability to utilize galactose as a carbon source because it has lost most of the genes involved in galactose metabolism. When we searched the GenBank non-redundant protein database by BLAST, we identified a *H. polymorpha* ATT1 ortholog (GenBank EFW98022.1) that displays 41% amino acid sequence identity over the entire length of the proteins. To evaluate if the *H. polymorpha* ATT1 ortholog (HpATT1) would perform similar functions as PpATT1, we cloned the HpATT1 open reading frame (ORF) downstream of the native PpATT1 promoter, and stably integrated this DNA construct at the URA6 locus of YGLY30547, which has its endogenous ATT1 already deleted. For comparison, we similarly integrated the *S. cerevisiae* ATT1 ortholog (ScGAL4) ORF at the URA6 locus of YGL30547 as well. To test what effects these ATT1 orthologs had on the temperature-resistant phenotype caused by the PpATT1 gene deletion, we randomly picked independent transformants containing either HpATT1 or ScGAL4 genes, patched them onto regular YPD agar plates, and monitored their growth at the permissive 24C and non-permissive 35C.

All ScGAL4-containing clones remained to be temperature resistant, just as the parent YGLY27611 does. These results indicated that, under the testing condition used in this experiment, the ScGAL4 could not substitute PpATT1's function in *P. pastoris*. In contrast, the HpATT1-containing transformants failed to grow at 35C, thus reverting the temperature-resistant phenotype of YGLY30547 back to temperature-sensitivity. These results demonstrated that the HpATT1 was able to functionally substitute PpATT1's activity in vivo.

Example 10

PpATT1 Truncations Screening for Improved Fermentation Robustness

To further explore the effects of ATT1 truncations on cell robustness, we constructed a series of new strains, in which the endogenous ATT1 ORF was deleted and replaced by DNA cassettes encoding varies length of the N-terminal portion of the ATT1 gene. The DNA cassettes were constructed very similarly to pGLY5948 or pGLY5949 described in Example 4, except that they contain, in their 5' cross-over region, DNA fragments encoding for the N-terminal 1-143aa, 1-196aa, 1-216aa, 1-276aa, 1-296aa, 1-341aa, 1-539aa, 1-622aa, 1-655aa, 1-728aa, 1-802aa, or 1-828aa of the ATT1 protein of SEQ ID NO:7. For comparisons, we also tested: a complete ATT1 deletion strain, as well as strains harboring the N-terminal 1-31aa, 1-164aa fragments of ATT1 which were described in Example 4.

In order to also examine how these truncated ATT1 fragments influence product titers, we transformed these DNA constructs into YGLY19315, a URA5-minus derivative of the YGLY13979 strain described above which expresses anti-HER2 mAb. These strains harboring the ATT1 deletions or truncations were cultivated in 1 L bioreactors at 32° C. using methanol-limited fedbatch fermentation process as described in Example 4. Cell lysis was monitored by microscopy every day, and fermentation was terminated when excess lysis was observed. If cell lysis levels were low, the fermentations were run up to between 100 to 120 hours of methanol induction. At the end of each fermentation run, cell-free supernatants were collected and mAb titers were determined using a protein A based HPLC method as described in Example 7.

Figure 19A:
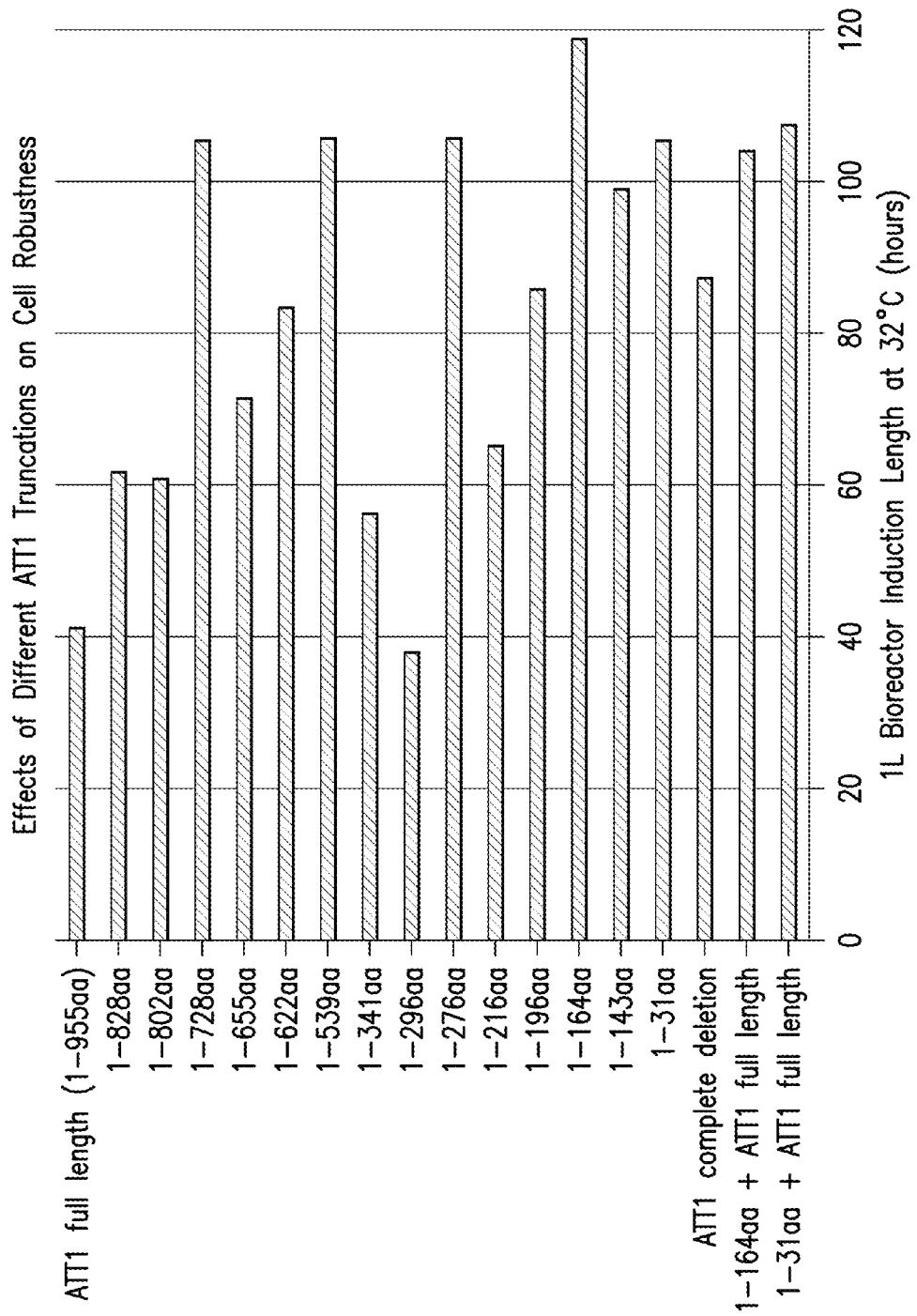
FIGS. 19A and 19B show the effects of different ATT1 truncations on cell robustness and product titers.
Figure 19B:
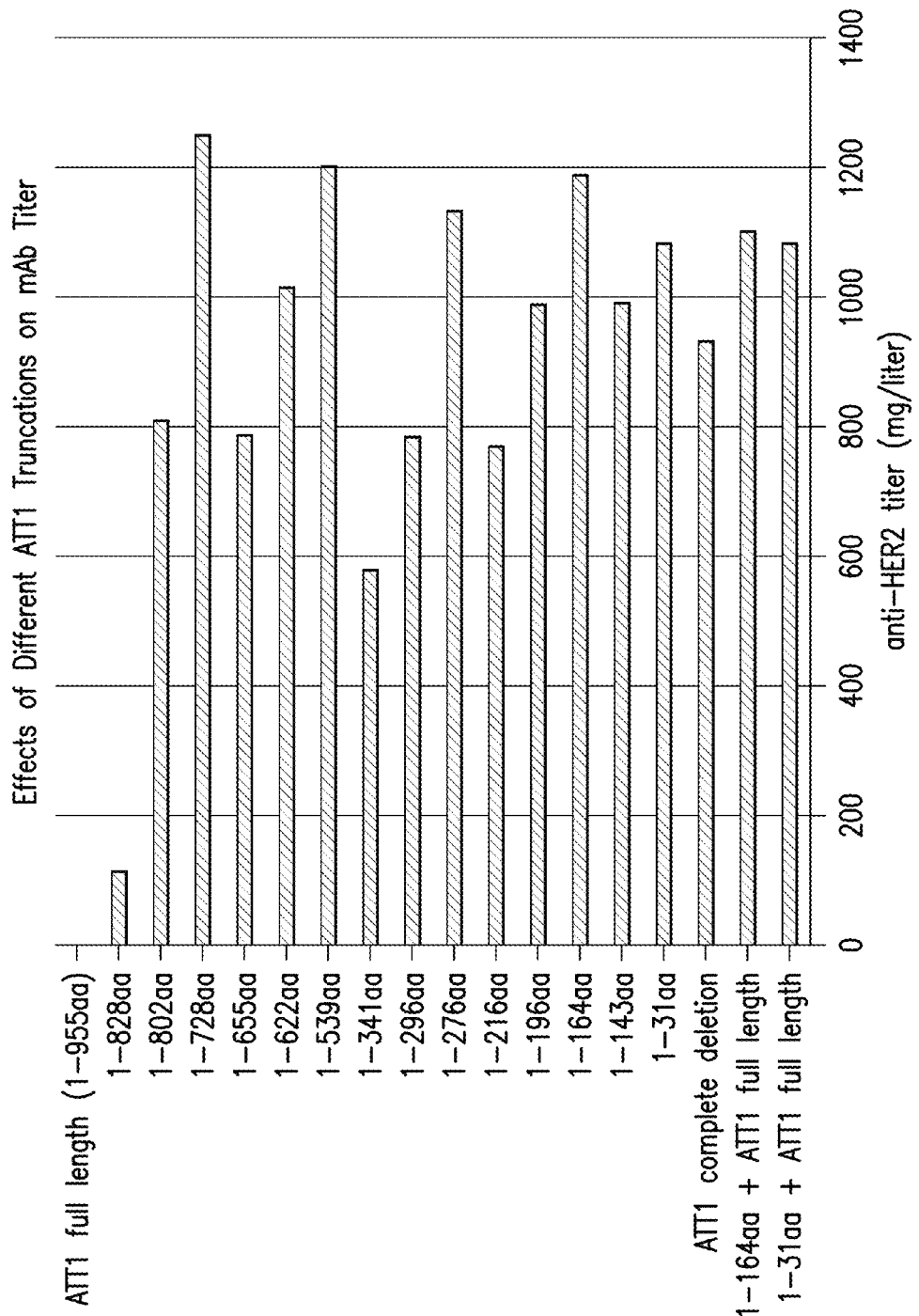

The results of these experiments are shown in FIGS. 19A and 19B. The control strain, which contained the full-length ATT1 gene, only survived ~40 hours of methanol induction at 32° C. (FIG. 19A). The ATT1 deletion strains lasted more than 80 hours induction, demonstrating that inactivating ATT1 activity dramatically improved fermentation robustness during fermentation. Surprisingly, the ATT1 (1-296 aa) fragment did not provide any robustness protection during fermentation. All other ATT1 truncations clearly improved fermentation robustness to different extents, with the 1-216aa, 1-341aa, 1-655aa, 1-802aa, and 1-828aa fragments providing modest levels of improvements, and 1-31aa, 1-143aa, 164aa, 1-196aa, 1-276aa, 1-539aa, 1-622aa and 1-728aa fragments providing strong improvements. Among all the truncations, the strain containing ATT1 (1-164aa) fragment appeared to display the highest level of robustness during these fermentation runs. As for product titers (FIG. 19B), only the 1-828aa ATT1 fragment significantly reduced to mAb titer to ~100 mg/liter, whereas strains containing other ATT1 fragments yielded between ~600 to 1200 mg/liter mAb, which are not significantly different than the ~1000 mg/liter titer observed from strains without any ATT1-modifications.

Example 11

ATT1 (1-31Aa) and (1-164Aa) Fragments are Dominant in the Presence of Full-Length ATT1 Gene As shown in Example 10, the strain containing ATT1 (1-164aa) fragment exhibited the most robust phenotype. Because the 1-164aa fragment contains the complete DNA-binding and dimerization regions, but is devoid of any transcriptional activation regions of the protein, the 1-164aa fragment could bind to the promoters of the target genes as non-active dimers, and prevent other transcriptional factors that might activate these target genes from binding, thus resulting in transcriptional repressions. If this is the case, one could predict that the 1-164aa ATT1 fragment should also compete with the full length ATT1 protein for promoter-binding and interfere with the ATT1 normal transcriptional activities. To verify this hypothesis, we introduced an ATT1 (1-164aa)-containing DNA construct into strain YGLY13979, which harbors the full-length ATT1 gene, and examined its effect on cell robustness during fermentation using 1 L bioreactor. As a control, we also transformed an ATT1 (1-31aa)-containing DNA construct into YGLY13979. Because the 1-31aa ATT1 fragment is upstream of the DNA-binding and dimerization domain (and is absence from the ScGAL4 protein), we expected that it would not interfere with the DNA-binding and transcriptional functions of the full-length ATT1 gene present in the YGLY13979 host. As shown in FIGS. 19A and 19B (bottom two bars), strains containing (1-164aa fragment+ATT1 full length) and (1-31aa fragment+ATT1 full length) lasted more than 100 hours of methanol induction at 32° C., demonstrating that both 1-164aa and 1-31aa fragments provided cell robustness protection in a dominant-fashion (i.e. in the presence of the wild type full length ATT1). The dominant-nature of the 1-164aa ATT1 fragment is consistent with the hypothesis described above. However, the observation that the 1-31aa fragment also exhibited a dominant-negative effect over the wild type ATT1 full-length gene was surprising.

Example 12

ATT1 Deletion and Truncations Improved Strain Robustness in 15 L Bioreactors For all previous examples, fermentation robustness was all evaluated using 1 liter lab-scale bioreactors. To see if ATT1-modification would provide the same robustness improvement in a larger bioreactor, we selected several strains containing either complete ATT1 deletion or distinct ATT1 truncations and performed methanol-limited fed-batch fermentations in 15 L bioreactors at 24° as described by Potgieter et al. 2009. Cell lysis, cell growth, and product titer were monitored throughout the fermentation process, and the fermentation runs were terminated once the cell growth stopped and cell lysis became excessive.

Figure 20:
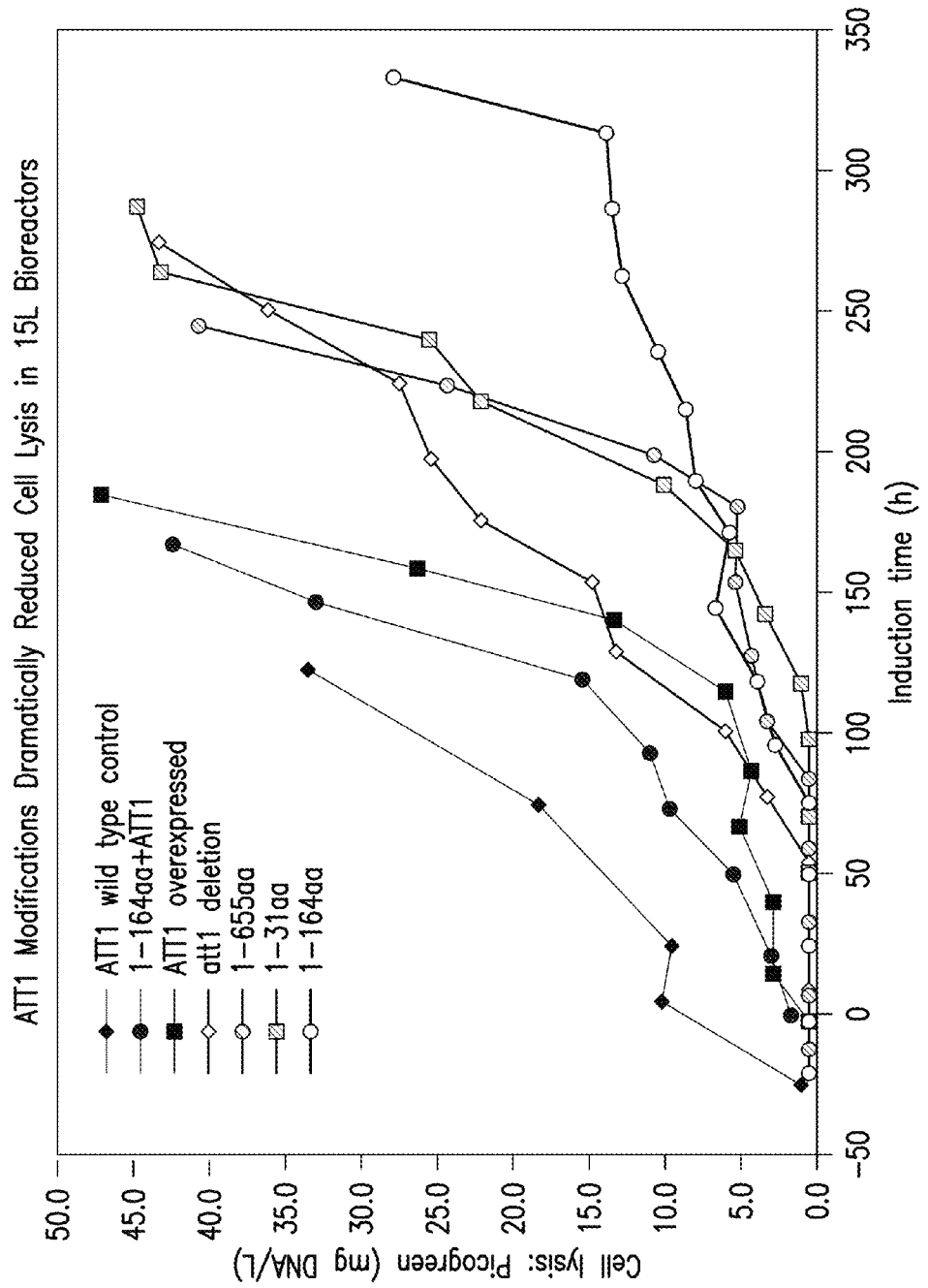
FIG. 20 shows the effect of different ATT1 modifications in cell lysis in 15 L bioreactors.

As shown in FIG. 20, the control strain (YGLY13979), which contains the wild type ATT1 gene intact, normally lasted around 120 hours of induction, at which time point the cell lysis became too high to continue.

For YGLY30539, which contains the ATT1 (1-164aa) fragment and the full-length ATT1 gene simultaneously, it became significantly more robust than the control strain and was able to survive more than 150 hours of induction. This finding confirmed that the 1-164aa fragment was capable of improving cell robustness even in the presence of the full length ATT1 gene.

The strain containing the full-length ATT1 overexpression cassette also displayed approximately the same level of robustness improvement, and was viable for about 170 hours after induction.

The strain containing the 1-655aa ATT1 fragment had a more pronounced fermentation robustness, and was viable for more than 200 hours after induction Strains harboring the complete ATT1 deletion or the 1-31aa fragment provided even further robustness protection, and both survived more than 250 hours of induction.

Remarkably, the 1-164aa fragment containing strain displayed the highest level of cell robustness, and finished more than 340 hours of induction at 24° C. in the 15 L bioreactor.

Collectively, these results demonstrated that ATT1-deletions, truncations, and selected form of overexpression as described above, can dramatically improve the cell robustness during fermentations runs, not only in 1 L small-scale bioreactors, but in 15 L-scale bioreactors as well. These findings strongly suggested the effects of these ATT1-modifications on cell robustness were easily scalable, and most likely would remain the same at larger fermentation scales (i.e. pilot-plant or production-scale) as well.

Example 13

ATT1 Deletion Also Improves Cell Robustness in Other *Pichia* Strains

*P. pastoris* glycoengineered strain YGLY23506 is a GFI2.0 strain, which secretes proteins with predominantly Man$_5$GlcNAc$_2$ N-glycans. (The construction of other *Pichia* strains, which are able to secrete Man$_5$GlcNAc2 has been previously described in Choi et al., 2003.) This host strain lineage has been sequentially modified by knockout of the yeast OCH1 gene as well as several other members of the mannosyl transferase family, including the four BMT β-mannosyl transferase genes and phosphomannosyl transferases. This strain engineering also includes expression of an alpha-1,2-mannosidase, which results in trimming of the core Man$_8$GlcNAc$_2$ N-glycan to a uniform Man$_5$GlcNAc$_2$ form. This particular strain has also been engineered to secrete an N-terminal H9G3 histidine-tagged soluble form of HIV gp120 from strain JR-FL (Varadarajan, 2005; Pang, 1991; Genbank AAB05604.1) containing amino acids 33-556 fused to the *S. cerevisiae* alpha factor prepro signal peptide.

Figure 21:
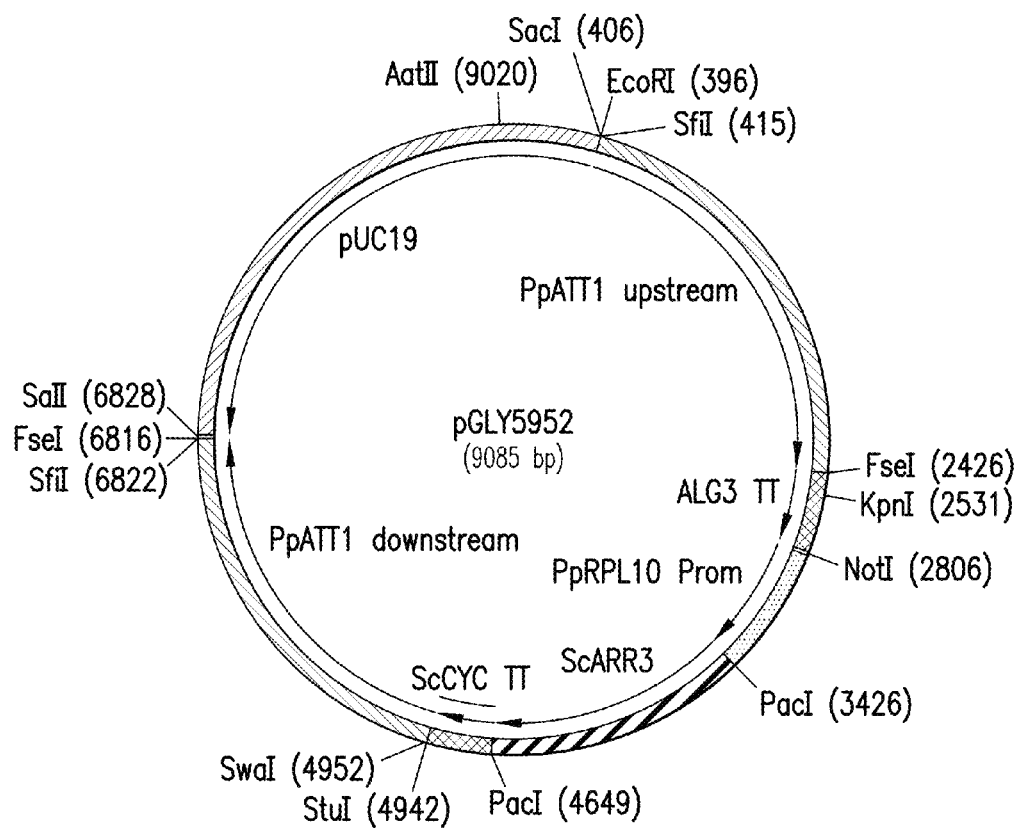
FIG. 21 shows a restriction map of plasmid pGLY5952. The *E. coli/P. pastoris* shuttle vector is depicted circularly as it is maintained in E. coll. The plasmid contains the pUC19 sequence for bacterial maintenance as well as the 5' and 3' regions of the *P. pastoris* ATT1 gene flanking the *S. cerevisiae* ARR3 gene (driven by the *P. pastoris* RPL10 promoter) as a selectable marker. For introduction into *P. pastoris* the plasmid is digested with SfiI to linearize and remove the pUC19 region, and selected for on medium containing 1-3 mM sodium arsenite, thus promoting replacement integration at the ATT1 locus with correct integrants (i.e. att1Δ strains) screened for by PCR.

Strain YGLY23506 was then transformed with plasmid pGLY5952, the Ppatt1::ArsR knockout plasmid (FIG. 21) using standard electroporation and clones were selected on YSD medium containing 1 mM sodium arsenite. Positive knockout clones were identified by PCR as described above. PCR confirmed strains YGLY30447, YGLY30448, YGLY30449, and YGLY30450 were saved as GFI2.0 att1Δ clones derived from YGLY23506.

*P. pastoris* glycoengineered strain YGLY23512 is a GFI1.0 strain, which secretes proteins with predominantly Man$_{8-10}$GlcNAc$_2$ N-glycans. (The construction of other *Pichia* strains, which are able to secrete Man$_{8-10}$GlcNAc$_2$ has been previously described in Choi et al., 2003.) This host strain lineage has been modified by knockout of the yeast N-glycosylation machinery similar to YGLY23506 but this strain does not express an alpha-mannosidase. This particular strain has also been engineered to secrete an N-terminal H9G3 histidine-tagged soluble form of HIV gp120 similar to strain YGLY23506, in this case fused to the *S. cerevisiae* alpha factor pre signal peptide. Strain YGLY23512 was transformed with plasmid pGLY5952 (FIG. 21), the Ppatt1::ArsR knockout plasmid using standard electroporation and clones were selected on YSD medium containing 1 mM sodium arsenite. Positive knockout clones were identified by PCR as described above. PCR confirmed strains YGLY30451, YGLY30452, YGLY30453, and YGLY30454 were saved as GFI1.0 att1 Δ clones of YGLY23512.

Strains YGLY23506, YGLY23512 and att1Δ versions of these strains were cultivated in 1 L fermentation to assess the robustness of these GFI2.0 and GFI1.0 glycoengineered strains.

Fermentation runs were carried out in a 1 L (0.75 L working volume) bioreactor from Sartorius. The 1 L system was controlled by Sartorius Biostat Q controllers with closed loop control of pH, temperature, and dissolved oxygen concentration. Shake flask cultures were grown in 4% BSGY medium in 1.0 L baffled flask at 24° C. while shaking for 48 h. Shake flask culture was then aseptically transferred into a 1.0 L Sartorius vessel containing 0.75 L of BSGY media at initial OD600 to 2. A standard glycerol-to-methanol fed-batch process was performed, including standard *Pichia* media components, as previously described (Potgieter et al, 2008). At the end of the transition phase a dose of 1.33 mL/L of methanol containing 2.5 mg/mL Pepstatin A and 1.59 mg/mL Chymostatin, 0.64 mg/ml PMTi4 was added prior to methanol induction. The culture temperature was measured by the pt100 sensor and controlled at 24±0.5° C. The pH was controlled at 6.0±0.1 during batch and fed-batch and 5.0±0.1 during induction phase using 30% NH4OH. No acid addition was done and the pH was allowed to reach the set point before inoculation using 30% NH4OH. The airflow was controlled at 0.7 vvm for 1 L. The DO set point of 20% (of saturation with air at atmospheric conditions, 1.7 mg/L) was maintained throughout the run by agitation speed (450-1200 rpm) cascaded onto 02 addition to the fixed airflow rate. Foaming was controlled by the addition of antifoam (Antifoam 204, Sigma-Aldrich) in the initial batch medium. An initial charge of 0.128 g/L of antifoam was added to the media before inoculation. A constant feed of 100% Methanol containing PTM2 and Biotin was initiated after the transition phase at constant feed rate (1.5 g/l/hr). The pH was gradually decreased to 5 from 6 in 120 min (line increment to 6.5 in 60 min whereas to 7 in further 60 min). Temp was maintained at 24° C. Every 24 hours of induction, 1.33 mL/L of methanol containing 2.5 mg/mL Pepstatin A and 1.59 mg/mL of Chymostatin was added. At the end of induction, all controls and pumps were stopped. Harvest was performed at room temperature. Primary clarification was then performed by centrifugation. The whole cell broth was transferred into 800 ml centrifuge bottles and centrifuged at 4° C. for 30 minutes at 13,000×g (8500 RPM).

Samples were taken from each fermenter approximately every 24 h starting prior to induction by removing 5 ml of broth, centrifuging in a tabletop centrifuge and removing the supernatant for analysis.

Figure 22:
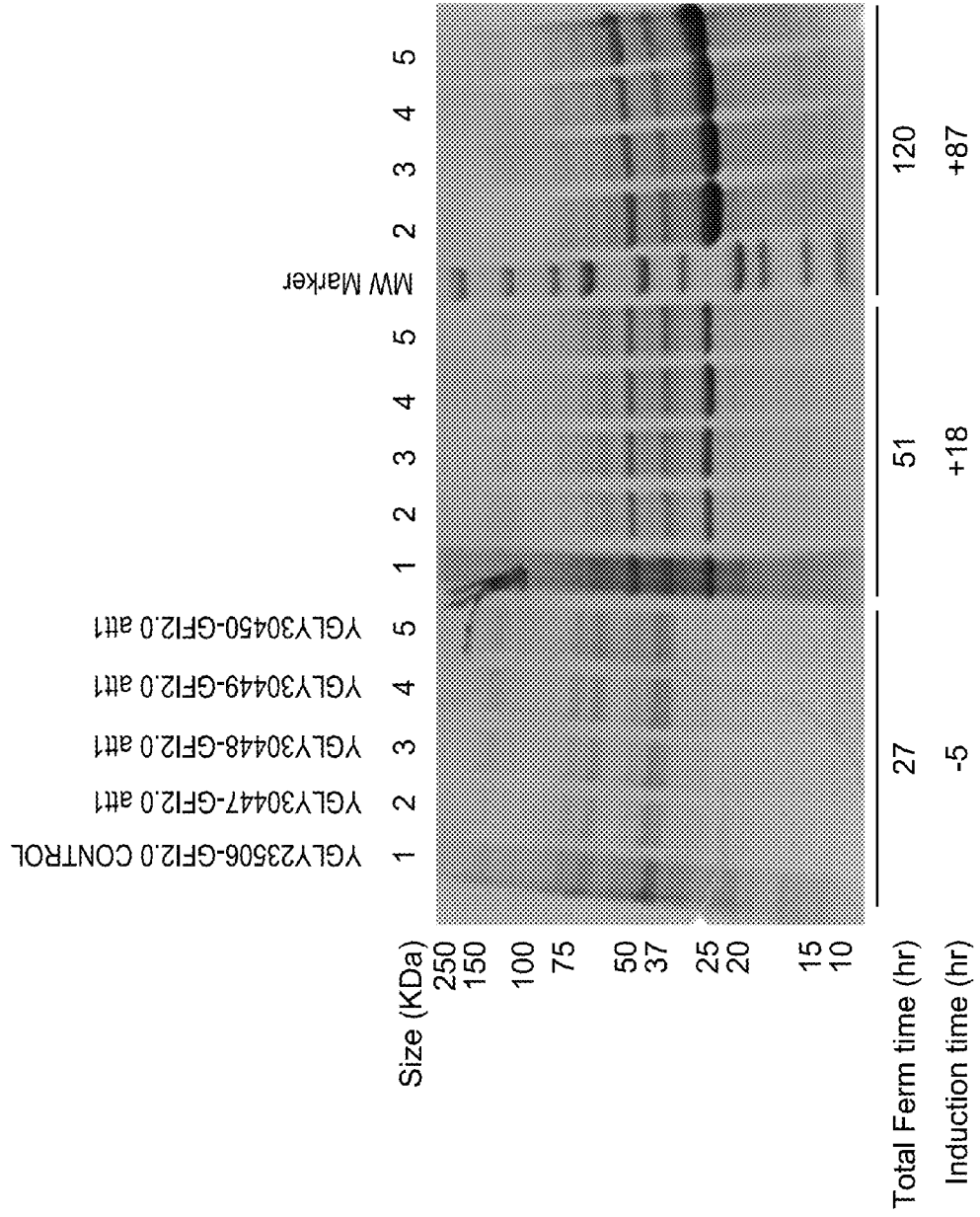
FIG. 22 shows an SDS-PAGE of GFI2.0 ATT1 wild type and att1Δ fermentation supernatants. Fermentation samples of GFI2.0 ATT1 wild type and att1Δ strains were taken every ~24 h and clarified supernatant was obtained by centrifugation at 13000×g. Samples were separated on SDS-PAGE and the gel was stained by coomassie blue. MW marker, Biorad Broad Range SDS-PAGE standard.

Fermentation cultured supernatants from strain YGLY23506, parental ATT1 WT GFI2.0 expressing secreted HIV gp120, and strains YGLY30447, YGLY30448, YGLY30449, and YGLY30450, att1Δ clones of YGLY23506, were separated on SDS-PAGE and Coomassie stained by standard means. The stained SDS-PAGE gel is shown in FIG. 22. The supernatant protein visible in the att1 knockout strains is significantly reduced compared to the parental GFI2.0 strain, particularly after methanol induction was initiated when the parental strain started extensively lysing, as apparent from the heavy burden of supernatant protein after 18 h of induction. This fermentation was ended due to extensive lysis after 66 h of induction. Conversely, the att1Δ strains still showed only a modest supernatant protein burden after more than 80 h of induction compared to the YGLY23506 parental strain at 18 h (FIG. 22).

Figure 23:
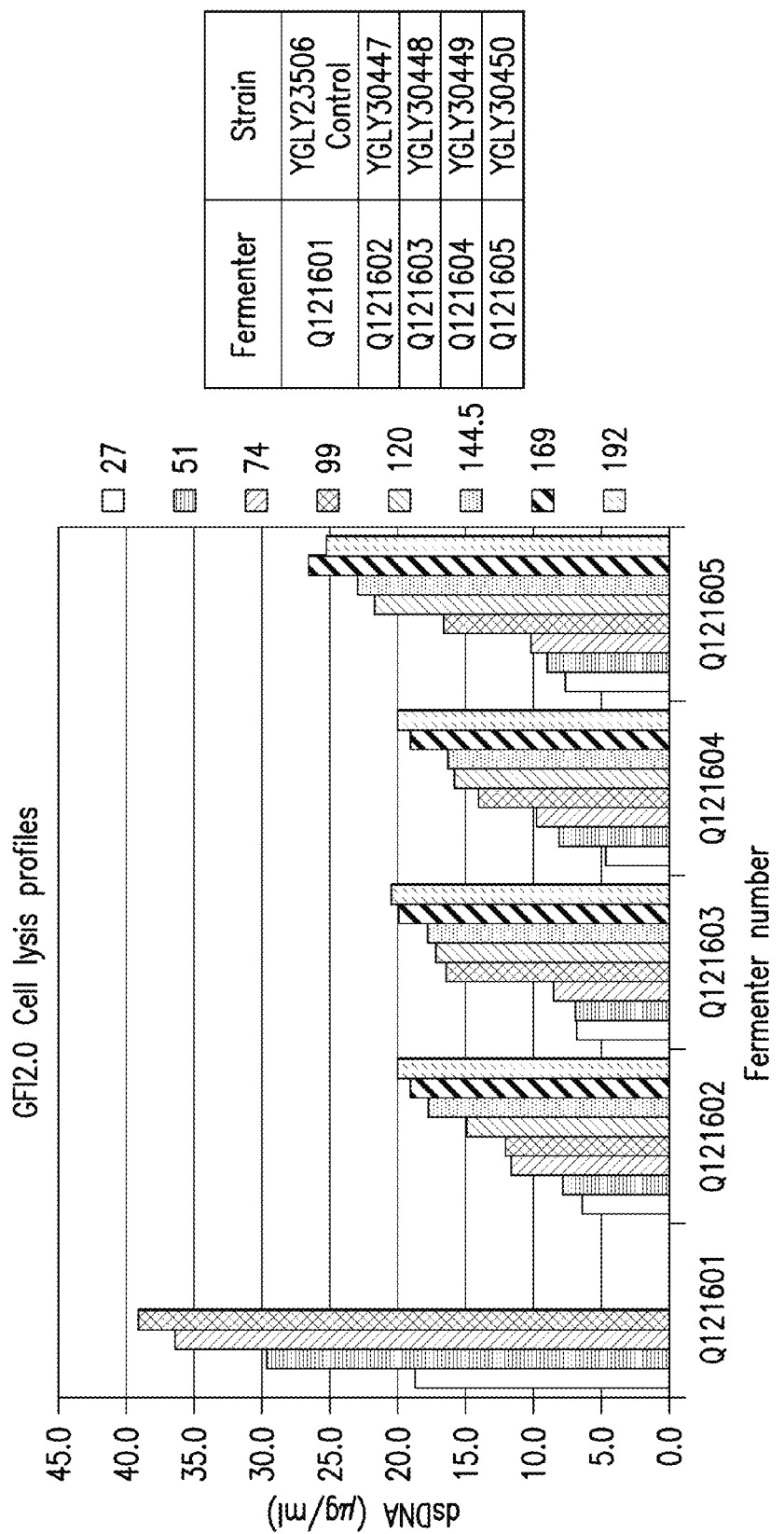
FIG. 23 shows supernatant DNA Quantification of GFI2.0 ATT1 wild type and att1Δ Fermentation Supernatants. Fermentation samples of GFI2.0 ATT1 wild type and att1Δ strains were taken every ~24 h and clarified supernatant was obtained by centrifugation at 13000×g. Cell lysis was measured by determining supernatant DNA loads. Samples were analyzed using the Picogreen (Invitrogen) fluorescent DNA stain and quantified using a plate reader as previously reported (Barnard, 2010).

In addition to SDS-PAGE, fermentation supernatants were analyzed by quantification of supernatant DNA using the Picogreen reagent (Invitrogen) as previously described (Barnard, 2010). Similar to the SDS-PAGE results, the supernatant DNA assay revealed that the YGLY23506 accumulated significantly more DNA at similar timepoints compared to the att1Δ clones. Moreover, the att1Δ clones maintained moderate supernatant DNA loads after 192 h of fermentation (159 h of induction) indicating at the GFI2.0 att1Δ clones are significantly more robust during standard *Pichia* fermentation process than the parental ATT1 wild type GFI2.0 comparator (FIG. 23).

Figure 24:
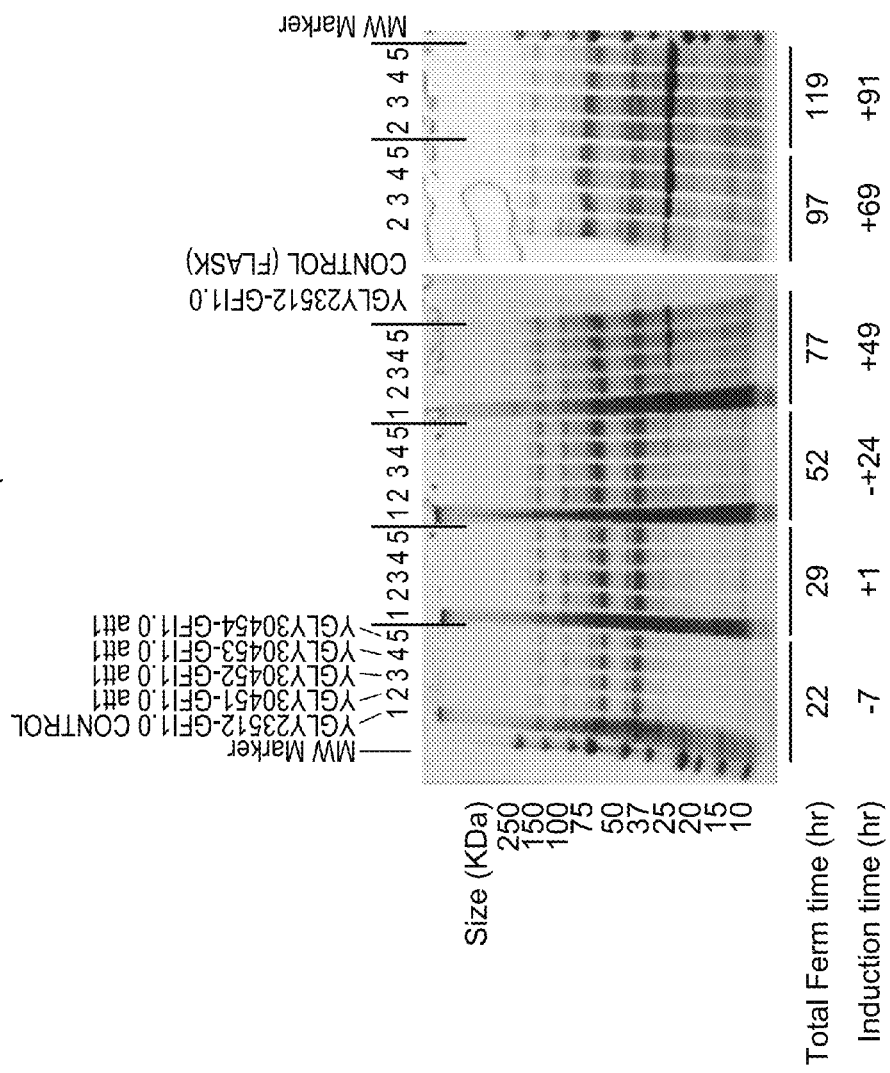
FIG. 24 shows an SDS-PAGE of GFI2.0 ATT1 wild type and att1Δ Fermentation Supernatants. Fermentation samples of GFI1.0 ATT1 wild type and att1Δ strains were taken every ~24 h and clarified supernatant was obtained by centrifugation at 13000×g. Samples were separated on SDS-PAGE and the gel was stained by coomassie blue. MW marker, Biorad Broad Range SDS-PAGE standard.

Similarly to the GFI2.0 strains above, fermentation cultured supernatants from strain YGLY23512, parental ATT1 WT GFI1.0 expressing secreted HIV gp120, and YGLY30451, YGLY30452, YGLY30453, and YGLY30454, att1Δ clones of YGLY23512, were separated on SDS-PAGE and Coomassie stained by standard means. The stained SDS-PAGE gel is shown in FIG. 24. The supernatant protein visible in the att1 knockout strains is significantly reduced compared to the parental GFI1.0 strain, particularly after methanol induction was initiated when the parental strain started extensively lysing, as apparent from the heavy burden of supernatant protein. This fermentation was ended due to extensive lysis after 49 h of methanol induction. Conversely, the att1Δ strains continued to show after than 90 h of induction a very low to modest supernatant protein burden compared to the YGLY23512 parental strain at very early induction timepoints (FIG. 24).

Figure 25:
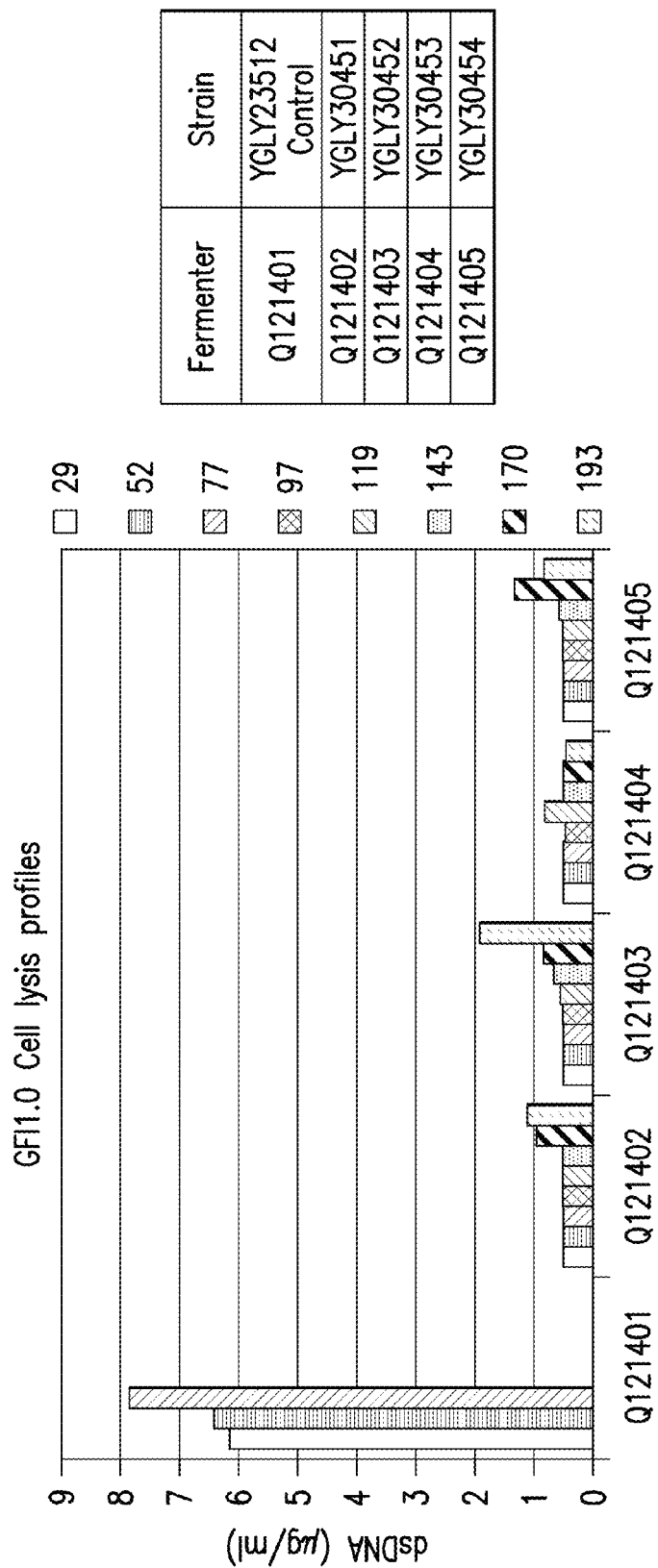
FIG. 25 shows supernatant DNA Quantification of GFI1.0 ATT1 wild type and att1Δ Fermentation Supernatants. Fermentation samples of GFI1.0 ATT1 wild type and att1Δ strains were taken every ~24 h and clarified supernatant was obtained by centrifugation at 13000×g. Cell lysis was measured by determining supernatant DNA loads. Samples were analyzed using the Picogreen (Invitrogen) fluorescent DNA stain and quantified using a plate reader as previously reported (Barnard, 2010).

As with the GFI2.0 strains, in addition to SDS-PAGE, fermentation supernatants were analyzed by quantification of supernatant DNA. The picogreen assay revealed that the parental ATT1 wild type strain YGLY23512 accumulated significantly more supernatant DNA at similar timepoints compared to the att1Δ clones (FIG. 25). Moreover, the att1Δ clones maintained moderate supernatant DNA loads after 193 h of fermentation (165 h of induction) indicating at the GFI1.0 att1Δ clones are significantly more robust during a standard *Pichia* fermentation process than the parental ATT1 wild type GFI1.0 comparator (FIG. 25).

SUMMARY

Deletion or truncations in ATT1 in naïve *Pichia* temperature-sensitive strains resulted in significant enhancements in both thermal-tolerance and fermentation robustness. The results described in Examples 1-4 have illustrated that the loss of function of the *Pichia* ATT1 gene is the genetic basis for the improved thermal-tolerance and fermentation robustness in these glyco-engineered *Pichia* strains. The ATT1 gene can be deleted or truncated in any *Pichia* strain and render the recipient strain highly robust during the fermentation induction phase, providing broad utility for any heterologous protein-expressing *Pichia* host strain where desired attributes include increased strain robustness and viability during fermentation, improved product yield, or reduced proteolytic degradation of the recombinant product.

Surprisingly, Examples 5-8, and 11 illustrate that engineered *Pichia* host strains overexpressing ATT1 under relevant bioprocess conditions also exhibit improved viability, stability, and protein production (FIGS. 15-17).

Currently, most of the marketed biologic therapeutics are produced using mammalian cell hosts. Over the past 30 years, through the collective efforts of the biotech and biopharmaceutical industry, the specific productivity of mammalian cell cultures has been improved for more than 100 fold, from ~50 mg per liter to ~5 g per liter range for mAb production. Contributing factors for such yield improvements have been attributed to the advancements of growing mammalian cell cultures to very high cell densities (from $10^5$ to $10^7$ cells per ml), and, more importantly, the ability to maintain high levels of cell viability for an extended time-period (from ~100 hours to ~400 hours) (Wurm 2004). Improving cell robustness and viability in *Pichia* host strains by engineering ATT1 overexpression, deletions or truncations enable higher production yield for recombinant protein therapeutics and facilitate the use of glyco-engineered *Pichia* as a recombinant-protein production platform.

GLOSSARY

ScSUC2: *S. cerevisiae* invertase
OCH1: Alpha-1,6-mannosyltransferase
KlMNN2-2: *K. lactis* UDP-GlcNAc transporter
BMT1: Beta-mannose-transfer (beta-mannose elimination)
BMT2: Beta-mannose-transfer (beta-mannose elimination)
BMT3: Beta-mannose-transfer (beta-mannose elimination)
BMT4: Beta-mannose-transfer (beta-mannose elimination)
MNN4L1: MNN4-like 1 (charge elimination)
MmSLC35A3: Mouse orthologue of UDP-GlcNAc transporter
PNO1: Phosphomannosylation of N-linked oligosaccharides (charge elimination)
MNN4: Mannosyltransferase (charge elimination)
ScGAL10: UDP-glucose 4-epimerase
XB33: Truncated HsGalT1 fused to ScKRE2 leader
DmUGT: UDP-Galactose transporter
KD53: Truncated DmMNSII fused to ScMNN2 leader
TC54: Truncated RnGNTII fused to ScMNN2 leader
NA10: Truncated HsGNTI fused to PpSEC12 leader
FB8: Truncated MmMNS1A fused to SeSEC12 leader
CiMNS1: Secreted Coccidioides immitis mannosidase I
STE13 Golgi dipeptidyl aminopeptidase
DAP2 Vacuolar dipeptidyl aminopeptidase
ALG3 dolichol-P-Man dependent alpha(1-3) mannosyltransferase
POMGNT1 protein 0-mannose beta-1,2-N-acetylglucosarninyltransferase
LmSTT3D: *Leishmania major* oligosaccharyl transferase subunit D

REFERENCES

Barnard G C, Kull A R, Sharkey N S, Shaikh S S, Rittenhour A M, Burnina I, Jiang Y, Li F, Lynaugh H, Mitchell T, Nett J H, Nylen A, Potgieter T I, Prinz B, Rios S E, Zha D, Sethuraman N, Stadheim T A, Bobrowicz P (2010) High-throughput screening and selection of yeast cell lines expressing monoclonal antibodies. J. Ind. Mierobiol. Biotechnol. 37(9):961-71.

Bobrowicz P, Davidson R C, Li H, Potgieter T I, Nett J H, Hamilton S R, Stadheim T A, Miele R G, Bobrowicz B, Mitchell T, Rausch S, Renfer E, Wildt S (2004) Engineering of an artificial glycosylation pathway blocked in core oligosaccharide assembly in the yeast *Pichia pastoris*: production of complex humanized glycoproteins with terminal galactose. Glycobiology 14(9):757-66.

Carter P, Presta L, Gorman C M, Ridgway J B, Henner D, Wong W L, Rowland A M, Kotts C, Carver M E, Shepard H M. Humanization of an anti-p185HER2 antibody for human cancer therapy. Proc Natl Acad Sci USA. 1992 May 15; 89(10):4285-9. PubMed PMID: 1350088

Choi B K, Bobrowicz P, Davidson R C, Hamilton S R, Kung D H, Li H, Miele R G, Nett J H, Wildt S, Gerngross T U (2003) Use of combinatorial genetic libraries to humanize N-linked glycosylation in the yeast *Pichia pastoris*. Proc Natl Acad Sci USA. 100(9):5022-7.

Hamilton S R, Davidson R C, Sethuraman N, Nett J H, Jiang Y, Rios S, Bobrowicz P, Stadheim T A, Li H, Choi B K, Hopkins D, Wischnewski H, Roser J, Mitchell T, Strawbridge R R, Hoopes J, Wildt S, Gerngross T U (2006) Humanization of yeast to produce complex terminally sialylated glycoproteins. Science 313(5792):1441-3.

Hopkins D, Gomathinayagam S, Rittenhour A M, Du M, Hoyt E, Karaveg K, Mitchell T, Nett J H, Sharkey N.J., Stadheim T A, Li H, Hamilton S R. Elimination of {beta}-mannose glycan structures in *Pichia pastoris*. Glycobiology. 2011 Aug. 12. [Epub ahead of print] PubMed PMID: 21840970.

Jiang Y, Li F, Zha D, Potgieter T I, Mitchell T, Moore R, Cukan M, Houston-Cummings N R, Nylen A, Drummond J E, McKelvey T W, d'Anjou M, Stadheim T A, Sethuraman N, Li H. Purification process development of a recombinant monoclonal antibody expressed in glycoengineered *Pichia pastoris*. Protein Expr Purif. 2011 March; 76(1):7-14. Epub 2010 Nov. 11. PubMed PMID: 21074617.

Li H, Sethuraman N, Stadheim T A, Zha D, Prinz B, Ballew N, Bobrowicz P, Choi B K, Cook W J, Cukan M, Houston-Cummings N R, Davidson R, Gong B, Hamilton S R, Hoopes J P, Jiang Y, Kim N, Mansfield R, Nett J H, Rios S, Strawbridge R, Wildt S, Gerngross T U (2006) Optimization of humanized IgGs in glycoengineered *Pichia pastoris*. Nat Biotechnol. 24(2):210-5.

Pang S, Vinters H V, Akashi T, O'Brien W A, Chen I S. HIV-1 env sequence variation in brain tissue of patients with AIDS-related neurologic disease. J Acquir Immune Defic Syndr. 1991; 4(11):1082-92. PubMed PMID: 1684385.

Potgieter T I, Cukan M, Drummond J E, Houston-Cummings N R, Jiang Y, Li F, Lynaugh H, Mallem M, McKelvey T W, Mitchell T, Nylen A, Rittenhour A, Stadheim T A, Zha D, d'Anjou M. (2009) Production of monoclonal antibodies by glycoengineered *Pichia pastoris*. J. Biotechnol. 139(4): 318-25.

Traven A, Jelicic B, Sopta M. (2006) Yeast GAL4: a transcriptional paradigm revisited. EMBO Rep. 7(5):496-9.

Varadarajan R, Sharma D, Chakraborty K, Patel M, Citron M, Sinha P, Yadav R, Rashid U, Kennedy S, Eckert D, Geleziunas R, Bramhill D, Schleif W, Liang X, Shiver J. Characterization of gp120 and its single-chain derivatives, gp120-CD4D12 and gp120-M9: implications for targeting the CD4i epitope in human immunodeficiency virus vaccine design. J Virol. 2005 February; 79(3):1713-23.

Winston F (2008) EMS and UV Mutagenesis in Yeast. Curr. Protoc. Mol. Biol. 82:13.3B.1-13.3B.5

Wurm F M. Production of recombinant protein therapeutics in cultivated mammalian cells. Nat Biotechnol. 2004 November; 22(11):1393-8. Review. PubMed PMID: 15529164.

Zhang N, Liu L, Dan Dumitru C, Cummings N R, Cukan M, Jiang Y, Li Y, Li F, Mitchell T, Mallem M R, Ou Y, Patel R N, Vo K, Vo K, Wang H, Burnina I, Choi B K, Huber H E, Stadheim T A, Zha D. Glycoengineered *Pichia* produced anti-HER2 is comparable to trastuzumab in preclinical study. MAbs. 2011 May 1; 3(3). [Epub ahead of print] PubMed PMID: 21487242.

TABLE 5

List of Sequences and Brief Description

| | |
|---|---|
| SEQ ID NO: 1 | *P. pastoris* wild-type ATT1 ORF |
| SEQ ID NO: 2 | mutant *P. pastoris* ATT1 with 5 bp insertion at position 92 produces truncation at amino acid 31 |
| SEQ ID NO: 3 | mutant *P. pastoris* ATT1 with mis-sense mutation at position 322 produces truncation at amino acid 107 |
| SEQ ID NO: 4 | mutant *P. pastoris* ATT1 with mis-sense mutation at position 493 produces truncation at position 164aa |
| SEQ ID NO: 5 | mutant *P. pastoris* ATT1 with mis-sense mutation at position 1966 produces truncation at amino acid 655aa |
| SEQ ID NO: 6 | *P. pastoris* TEF promoter |
| SEQ ID NO: 7 | *P. pastoris* wild-type ATT1 amino acid sequence |
| SEQ ID NO: 8 | *P. pastoris* truncation mutant att1 resulting from the 5 bp insertion (amino acids 1-31 att1 + mutant insert amino acids) |

TABLE 5-continued

List of Sequences and Brief Description

| | |
|---|---|
| SEQ ID NO: 9 | *P. pastoris* truncation mutant att1p 1-107 |
| SEQ ID NO: 10 | *P. pastoris* truncation mutant att1p 1-164 |
| SEQ ID NO: 11 | *P. pastoris* truncation mutant att1p 1-655 |
| SEQ ID NO: 12 | *P. pastoris* primer located 2370 bp upstream of ATT1 start |
| SEQ ID NO: 13 | *P. pastoris* primer within the ALG3 terminator to confirm the 5' junction of the gene-replacement |
| SEQ ID NO: 14 | Primer within lacZ |
| SEQ ID NO: 15 | *P. pastoris* primer located 2014 bp downstream of the ATT1 stop codon to confirm the 3' junction of the gene-replacement |
| SEQ ID NO: 16 | *P. pastoris* primer located 365 bp upstream of the ATT1 start |
| SEQ ID NO: 17 | *P. pastoris* primer within the ATT1 ORF, 1070 bp after the start to confirm the absence of the wild-type ATT1 ORF |
| SEQ ID NO: 18 | *P. pastoris* frame-shift insertion after the 31st amino acid residue of the ATT1 ORF |
| SEQ ID NO: 19 | *P. pastoris* primer located 1081 bp downstream of the ATG start codon of ATT1 ORF |
| SEQ ID NO: 20 | *P. pastoris* primer located within the AOX1 promoter |
| SEQ ID NO: 21 | *P. pastoris* primer located within the TEF promoter |
| SEQ ID NO: 22 | *P. pastoris* AOX1 promoter |
| SEQ ID NO: 23 | *H. polymorpha* ATT1 polypeptide |
| SEQ ID NO: 24 | *Pichia stipitis* ATT1 polypeptide |
| SEQ ID NO: 25 | *Pichia guilliermondii* ATT1 polypeptide |
| SEQ ID NO: 26 | *Kluyveromyces lactis* ATT1 polypeptide |
| SEQ ID NO: 27 | *Aspergillus niger* ATT1 polypeptide |
| SEQ ID NO: 28 | *Aspergillus nidulans* ATT1 polypeptide |
| SEQ ID NO: 29 | *Aspergillus flavus* ATT1 polypeptide |
| SEQ ID NO: 30 | *Debaryomyces hansenii* ATT1 polypeptide |
| SEQ ID NO: 31 | *Zygosaccharomyces rouxii* ATT1 polypeptide |
| SEQ ID NO: 32 | *Sachharomyces cerevisiae* ATT1 polypeptide |

Patents, patent applications, publications, product descriptions, and protocols are cited throughout this application, the disclosures of which are incorporated herein by reference in their entireties for all purposes. All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. §1.57(b)(1), to relate to each and every individual publication, database entry (e.g. Genbank sequences or GeneID entries), patent application, or patent, each of which is clearly identified in compliance with 37 C.F.R. §1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein; the embodiments specifically set forth herein are not necessarily intended to be exhaustive. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. An engineered *Pichia pastoris* host cell that has been modified to reduce or eliminate the activity of an ATT1 gene, wherein the ATT1 gene encodes a polypeptide comprising the amino acid sequence set forth in SEQ ID NO:7, wherein the activity of the ATT1 gene is reduced or eliminated by: (i) reducing or eliminating the expression of an ATT1 gene or polypeptide, or (ii) expressing a mutated form of an ATT1 gene; and wherein the host cell further comprises a nucleic acid encoding a recombinant protein.

2. The host cell of claim 1, further comprising a mutation, disruption or deletion of one or more genes encoding protease activities, alpha-1,6-mannosyltransferase activities, alpha-1,2-mannosyltransferase activities, mannosylphosphate transferase activities, β-mannosyltransferase activities, O-mannosyltransferase (PMT) activities, and/or dolichol-P-Man dependent alpha(1-3) mannosyltransferase activities.

3. The host cell of claim 1, further comprising one or more nucleic acids encoding one or more glycosylation enzymes selected from the group consisting of: glycosidases, mannosidases, phosphomannosidases, phosphatases, nucleotide sugar transporters, nucleotide sugar epimerases, mannosyltransferases, N-acetylglucosaminyltransferases, CMP-sialic acid synthases, N-acetylneuraminate-9-phosphate synthases, galactosyltransferases, sialyltransferases, and oligosaccharyltransferases.

4. The host cell of claim 1, wherein the recombinant protein is selected from the group consisting of: an antibody (IgA, IgG, IgM or IgE), an antibody fragment, kringle domains of the human plasminogen, erythropoietin, cytokines, coagulation factors, soluble IgE receptor α-chain, urokinase, chymase, urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, α-1 antitrypsin, DNase II, α-feto proteins, insulin, Fc-fusions, and HSA-fusions.

5. The host cell of claim 1, wherein the cell exhibits an increase in culture stability, thermal tolerance and/or improved fermentation robustness compared with an ATT1 naïve parental host cell under similar culture conditions.

6. The host cell of claim 5, wherein the cell is capable of surviving in culture at 32° C. for at least 80 hours of fermentation with minimal cell lysis.

7. The host cell of claim 2, wherein the host cell is glycoengineered.

8. The host cell of claim 2, wherein the host cell lacks OCH1 activity.

9. A method for producing a heterologous polypeptide in an *Pichia* sp. host cell, said method comprising: (a) introducing a polynucleotide encoding a heterologous polypeptide into the host cell of claim 1; (b) culturing said host cell under conditions favorable to the expression of the heterologous polypeptide; and, optionally, (c) isolating the heterologous polypeptide from the host cell.

* * * * *

SEQUENCE LISTING

<160> NUMBER OF SEQ ID NOS: 33

<210> SEQ ID NO 1
<211> LENGTH: 2985
<212> TYPE: DNA
<213> ORGANISM: Pichia pastoris

<400> SEQUENCE: 1

| | | | | | | |
|---|---|---|---|---|---|---|
| atgcatcata | aagaaagact | catagatcat | atttcttcgg | agtctaactt | ctcccttcc | 60 |
| acttcgtcga | tgccgtcctt | cagccatgaa | tcaaatcaat | cgccgaaccc | aatgctgatc | 120 |
| gaacaagctt | gcgattcctg | tcgtaagcgc | aaattaaggt | gttctaagga | atacccaaag | 180 |
| tgttccaaat | gtgtcaccca | caaatggagt | tgcgtttatt | caccaaggac | agtgagatct | 240 |
| ccgttgacga | gagctcatct | gaccaaagtg | gaaaatcgtg | tacgaatgtt | ggaagatctg | 300 |
| ttggaacgag | ttttccctac | tcagagtgtc | gaccagttac | tggaaaagag | aaccagtcta | 360 |
| tccggcaact | ccacggggca | ttctccatct | tatccaaata | gtaattccgt | ttcccccag | 420 |
| aattcctccc | caaagttag | cgactcttcc | tcaacgactg | ctgaacccgc | tccagtcctt | 480 |
| ccatccaaac | ccaaatcttc | attccgtcca | atagttccag | atgactactt | cctgaatgat | 540 |
| gaaatcaacg | gtttcgattg | ggaggaggaa | gacaccccag | atcaattgtt | ggtaatgcag | 600 |
| caacctccga | catccgtcga | ttccacgaat | gtctcacatt | cttactggaa | tcatagccga | 660 |
| agatcgcaga | aaaattccgt | gacttcgttg | aactcacttg | cggagcacga | acaatccggt | 720 |
| tgctcttcgt | tgataacgtc | ccccagccta | cagccacttt | tcagacaac | aaccaatgat | 780 |
| tcccaccccg | atggaatggc | tgctctttca | gttaaccta | agggtggatc | tggatatttt | 840 |
| gggttctctt | caagttctgg | acttctaagg | gcattgaagc | tgggtcaatt | tgattccgct | 900 |
| tccatatctc | ctatgagctc | tgttaggaac | tcggtctcca | agactaatac | tgaacctact | 960 |
| gaaccacaat | caattcgttc | tttactagga | gatcccaatg | actttttgga | acccgaaaag | 1020 |
| aaggctgaat | tcccaggcta | cgattctcac | ttaaatgacc | ctaacaacca | atcccaatat | 1080 |
| ctccaggcct | acttcaagta | ttatcacaca | tcgtatcctt | tcatccacaa | aggatcattc | 1140 |
| ctcaaacatt | atgctgggga | gctaccaatc | aagaatgaga | accattggca | gattttgctt | 1200 |
| aatgtcgtac | ttgctctagg | atgttggtgt | ttgaatggag | aatcttcctc | gattgatctt | 1260 |
| tgctactaca | atagagcaaa | gatgctttta | aagcaggtgg | gtattttga | atgtggtaac | 1320 |
| attatgctgt | tagagtcttt | gattctcctt | tcgaactata | cgcagaagag | aaataagcct | 1380 |
| aatacaggat | ggagttactt | aggtattgct | attagaatgg | ctatgtcttt | agggctttac | 1440 |
| aaagagttca | acttggacca | tacagaaaag | gaccactatc | tcaacttaga | aatcagaaga | 1500 |
| cggttatggt | ggggtttgta | cattttcgat | gctggagctt | caataacttt | tggtcgtcct | 1560 |
| atcactttac | caagcagaga | ttcgtgtgat | attcaactgt | gttccaatat | caatgatgcc | 1620 |
| gagttggaag | aattgatcga | aataaaatcg | gattcaatca | ctactgagga | ccttaacaaa | 1680 |
| ccatacccaa | cagcatactc | cggtttgatt | cagcaaaccc | agtttactga | attatctatg | 1740 |
| aaaatttaca | accgtttggt | ttccaaacca | gctccaactg | ttgaagaatg | tctagacatg | 1800 |
| aacatggaaa | ttgaaaattt | cataaagggt | cttcccgctt | acttccatga | aagcaatgaa | 1860 |
| attgcaatgt | ctcagttcta | caaggttacg | ccgtccaaat | attacgatta | tgacagcaac | 1920 |
| aaacaggtgg | actatacccg | cttaccgcaa | tggtttgatc | taagtcgaag | tagattgatt | 1980 |
| tggagataca | agaacctgca | aattacccct | ttccgagcat | ttatttggca | acgagtcatt | 2040 |
| ggagtaacca | atcccaaggt | acttcaacag | tgtaagacta | gcagaggtaa | ggaatgtcga | 2100 |

-continued

```
actatttgtt tgagagttgc tcatgaaaca attttgtcta ttcaacagtt cgtgaatatt    2160
gacgatgatg atgacttctc tagactatcg gtcattggat gttggtatgc tacgtacttc    2220
ctattccagg ctgtcctgat tccaatcgct tgtctttgtt ctgaaccgga tagcaaatat    2280
gctccaattt ggatcgagga tattcaaatt agtaagaaga tcttcttgaa gctcaacaag    2340
ctcaactcgt tggcatctaa gtttgccaat gttattgaca gatcaatgag tcaagtaatg    2400
ccacagttcg acacaacaag cgccaaggac tctccactca acattaacga tttgatcgat    2460
atgcacggtc tcatgggtaa cagccccgct cctggttcta caacaatag caacaccaaa     2520 agcagcccca gcactaccaa caataccagg accccaaca ctatcaacaa aaacaacagt     2580
aacatgaaca ataatagtat caataactat tttaacaaca acagcaacaa caataactcc    2640
ttctccagtt cgaaggctgg accagtgaaa caggaatttg aagattactg tttaaagctg    2700
gaccctgaag acgaagacat gtctgcctta gagtttaccg cagttcgatt cccccaacttt   2760 tcagctacga caacagcccc gcctcctact ccagtcaatt gcaacagtcc tgaaaacatc    2820
aagacctcca ctgtggacga ttttttgaaa gctactcaag atccaaataa caagagata    2880 ctcaacgaca tttacagttt gattttttgat gactccatgg atcctatgag cttcggaagt   2940
atggaaccaa gaaacgattt ggaagttccg gacactataa tggat                    2985
```

<210> SEQ ID NO 2
<211> LENGTH: 2990
<212> TYPE: DNA
<213> ORGANISM: Pichia pastoris

<400> SEQUENCE: 2

```
atgcatcata aagaaagact catagatcat atttcttcgg agtctaactt ctcccttttcc     60 acttcgtcga tgccgtcctt cagccatgaa tcgaatcaaa tcaatcgccg aacccaatgc    120
tgatcgaaca agcttgcgat tcctgtcgta agcgcaaatt aaggtgttct aaggaatacc    180
caaagtgttc caaatgtgtc acccacaaat ggagttgcgt ttattcacca aggacagtga    240
gatctccgtt gacgagagct catctgacca aagtggaaaa tcgtgtacga atgttggaag    300
atctgttgga acgagttttc cctactcaga gtgtcgacca gttactggaa aagagaacca    360
gtctatccgg caactccacg gggcattctc catcttatcc aaatagtaat tccgtttccc    420
cccagaattc ctccccaaaa gttagcgact cttcctcaac gactgctgaa cccgctccag    480
tccttccatc caaacccaaa tcttcattcc gtccaatagt tccagatgac tacttcctga    540
atgatgaaat caacggtttc gattgggagg aggaagacac cccagatcaa ttgttggtaa    600
tgcagcaacc tccgacatcc gtcgattcca cgaatgtctc acattcttac tggaatcata    660
gccgaagatc gcagaaaaat tccgtgactt cgttgaactc acttgcggag cacgaacaat    720
ccggttgctc ttcgttgata acgtccccca gcctacagcc actttctcag acaacaacca    780
atgattccca ccccgatgga atggctgctc tttcagttaa ccttaagggt ggatctggat    840
attttgggtt ctcttcaagt tctggacttc taagggcatt gaagctgggt caatttgatt    900
ccgcttccat atctcctatg agctctgtta ggaactcggt ctccaagact aatactgaac    960
ctactgaacc acaatcaatt cgttctttac taggagatcc caatgacttt ttggaacccg   1020
aaaagaaggc tgaattccca ggctacgatt ctcacttaaa tgaccctaac aaccaatccc   1080
aatatctcca ggcctacttc aagtattatc acacatcgta tccttttcatc cacaaaggat   1140 cattcctcaa acattatgct ggggagctac caatcaagaa tgaagaaccat ggcagatttt   1200
```

```
tgcttaatgt cgtacttgct ctaggatgtt ggtgtttgaa tggagaatct tcctcgattg    1260
atctttgcta ctacaataga gcaaagatgc ttttaaagca ggtgggtatt tttgaatgtg    1320
gtaacattat gctgttagag tctttgattc tcctttcgaa ctatacgcag aagagaaata    1380
agcctaatac aggatggagt tacttaggta ttgctattag aatggctatg tctttagggc    1440
tttacaaaga gttcaacttg gaccatacag aaaaggacca ctatctcaac ttagaaatca    1500
gaagacggtt atggtggggt tgtacatttt cgatgctgg agcttcaata acttttggtc     1560
gtcctatcac tttaccaagc agagattcgt gtgatattca actgtgttcc aatatcaatg    1620
atgccgagtt ggaagaattg atcgaaataa aatcggattc aatcactact gaggacctta    1680
acaaaccata cccaacagca tactccggtt tgattcagca aacccagttt actgaattat    1740
ctatgaaaat ttacaaccgt ttggtttcca accagctcc aactgttgaa gaatgtctag      1800
acatgaacat ggaaattgaa aatttcataa agggtcttcc cgcttacttc catgaaagca    1860
atgaaattgc aatgtctcag ttctacaagg ttacgccgtc caaatattac gattatgaca    1920
gcaacaaaca ggtggactat acccgcttac cgcaatggtt tgatctaagt cgaagtagat    1980
tgatttggag atacaagaac ctgcaaatta cccttttccg agcatttatt tggcaacgag    2040
tcattggagt aaccaatccc aaggtacttc aacagtgtaa gactagcaga ggtaaggaat    2100
gtcgaactat ttgtttgaga gttgctcatg aaacaatttt gtctattcaa cagttcgtga    2160
atattgacga tgatgatgac ttctctagac tatcggtcat ggatgttgg tatgctacgt      2220 acttcctatt ccaggctgtc ctgattccaa tcgcttgtct tgttctgaa ccggatagca      2280 aatatgctcc aatttggatc gaggatattc aaattagtaa gaagatcttc ttgaagctca    2340
acaagctcaa ctcgttggca tctaagtttg ccaatgttat tgacagatca atgagtcaag    2400
taatgccaca gttcgacaca caagcgcca aggactctcc actcaacatt aacgatttga     2460
tcgatatgca cggtctcatg ggtaacagcc ccgctcctgg ttctaacaac aatagcaaca    2520
ccaaaagcag ccccagcact accaacaata ccaggacccc caacactatc aacaaaaaca    2580
acagtaacat gaacaataat agtatcaata actattttaa caacaacagc aacaacaata    2640
actccttctc cagttcgaag gctggaccag tgaaacagga atttgaagat tactgtttaa    2700
agctggaccc tgaagacgaa gacatgtctg ccttagagtt taccgcagtt cgattcccca    2760
acttttcagc tacgacaaca gccccgcctc ctactccagt caattgcaac agtcctgaaa    2820
acatcaagac ctccactgtg gacgattttt tgaaagctac tcaagatcca aataacaaag    2880
agatactcaa cgacatttac agtttgattt ttgatgactc catggatcct atgagcttcg    2940
gaagtatgga accaagaaac gatttggaag ttccggacac tataatggat           2990
```

<210> SEQ ID NO 3
<211> LENGTH: 2985
<212> TYPE: DNA
<213> ORGANISM: Pichia pastoris

<400> SEQUENCE: 3

```
atgcatcata agaaagact catagatcat atttcttcgg agtctaactt ctccctttcc      60
acttcgtcga tgccgtcctt cagccatgaa tcaaatcaat cgccgaaccc aatgctgatc    120
gaacaagctt gcgattcctg tcgtaagcgc aaattaaggt gttctaagga atacccaaag    180
tgttccaaat gtgtcaccca caatggagt tgcgtttatt caccaaggac agtgagatct      240
ccgttgacga gagctcatct gaccaaagtg gaaaatcgtg tacgaatgtt ggaagatctg    300
ttggaacgag ttttccctac ttagagtgtc gaccagttac tggaaaagag aaccagtcta    360
```

```
tccggcaact ccacggggca ttctccatct tatccaaata gtaattccgt ttcccccag       420 aattcctccc caaaagttag cgactcttcc tcaacgactg ctgaacccgc tccagtcctt      480
ccatccaaac ccaaatcttc attccgtcca atagttccag atgactactt cctgaatgat      540
gaaatcaacg gtttcgattg ggaggaggaa gacaccccag atcaattgtt ggtaatgcag      600
caacctccga catccgtcga ttccacgaat gtctcacatt cttactggaa tcatagccga      660
agatcgcaga aaaattccgt gacttcgttg aactcacttg cggagcacga acaatccggt      720
tgctcttcgt tgataacgtc ccccagccta cagccacttt ctcagacaac aaccaatgat      780
tcccaccccg atggaatggc tgctctttca gttaaccta agggtggatc tggatatttt       840
gggttctctt caagttctgg acttctaagg gcattgaagc tgggtcaatt tgattccgct      900
tccatatctc ctatgagctc tgttaggaac tcggtctcca agactaatac tgaacctact      960
gaaccacaat caattcgttc tttactagga gatcccaatg acttttgga acccgaaaag       1020 aaggctgaat tccgaggcta cgattctcac ttaaatgacc ctaacaacca atcccaatat      1080
ctccaggcct acttcaagta ttatcacaca tcgtatcctt tcatccacaa aggatcattc      1140
ctcaaacatt atgctgggga gctaccaatc aagaatgaga accattggca gattttgctt      1200
aatgtcgtac ttgctctagg atgttggtgt ttgaatggag aatcttcctc gattgatctt      1260
tgctactaca atagagcaaa gatgctttta aagcaggtgg gtattttga atgtggtaac        1320 attatgctgt tagagtcttt gattctcctt tcgaactata cgcagaagag aaataagcct      1380
aatacaggat ggagttactt aggtattgct attagaatgg ctatgtcttt agggctttac      1440
aaagagttca acttggacca tacagaaaag gaccactatc tcaacttaga aatcagaaga      1500
cggttatggt ggggtttgta cattttcgat gctggagctt caataacttt tggtcgtcct       1560
atcactttac caagcagaga ttcgtgtgat attcaactgt gttccaatat caatgatgcc      1620
gagttggaag aattgatcga aataaaatcg gattcaatca ctactgagga ccttaacaaa      1680
ccatacccaa cagcatactc cggtttgatt cagcaaaccc agttactga attatctatg       1740 aaaatttaca accgtttggt ttccaaacca gctccaactg ttgaagaatg tctagacatg      1800
aacatggaaa ttgaaaattt cataaagggt cttcccgctt acttccatga aagcaatgaa      1860
attgcaatgt ctcagttcta caaggttacg ccgtccaaat attacgatta tgacagcaac      1920
aaacaggtgg actatacccg cttaccgcaa tggtttgatc taagtcgaag tagattgatt       1980
tggagataca agaacctgca aattacccct ttccgagcat ttatttggca acgagtcatt      2040
ggagtaacca atcccaaggt acttcaacag tgtaagacta gcagaggtaa ggaatgtcga     2100
actatttgtt tgagagttgc tcatgaaaca atttgtcta ttcaacagtt cgtgaatatt        2160
gacgatgatg atgacttctc tagactatcg gtcattggat gttggtatgc tacgtacttc      2220
ctattccagg ctgtcctgat tccaatcgct tgtctttgtt ctgaaccgga tagcaaatat      2280
gctccaattt ggatcgagga tattcaaatt agtaagaaga tcttcttgaa gctcaacaag      2340
ctcaactcgt tggcatctaa gtttgccaat gttattgaca gatcaatgag tcaagtaatg      2400
ccacagttcg acacaacaag cgccaaggac tctccactca acattaacga tttgatcgat       2460
atgcacggtc tcatgggtaa cagcccgcct cctggttcta caacaatag caacaccaaa       2520 agcagcccca gcactaccaa caataccagg accccaaca ctatcaacaa aaacaacagt       2580
aacatgaaca ataatagtat caataactat tttaacaaca acagcaacaa caataactcc      2640
ttctccagtt cgaaggctgg accagtgaaa caggaatttg aagattactg tttaaagctg      2700
```

```
gaccctgaag acgaagacat gtctgcctta gagtttaccg cagttcgatt ccccaacttt    2760
tcagctacga caacagcccc gcctcctact ccagtcaatt gcaacagtcc tgaaaacatc    2820
aagacctcca ctgtggacga ttttttgaaa gctactcaag atccaaataa caaagagata    2880
ctcaacgaca tttacagttt gattttttgat gactccatgg atcctatgag cttcggaagt    2940
atggaaccaa gaaacgattt ggaagttccg gacactataa tggat                    2985

<210> SEQ ID NO 4
<211> LENGTH: 2985
<212> TYPE: DNA
<213> ORGANISM: Pichia pastoris

<400> SEQUENCE: 4
atgcatcata aagaaagact catagatcat atttcttcgg agtctaactt ctcccttttcc     60 acttcgtcga tgccgtcctt cagccatgaa tcaaatcaat cgccgaaccc aatgctgatc    120
gaacaagctt gcgattcctg tcgtaagcgc aaattaaggt gttctaagga atacccaaag    180
tgttccaaat gtgtcaccca caaatggagt tgcgtttatt caccaaggac agtgagatct    240
ccgttgacga gagctcatct gaccaaagtg gaaaatcgtg tacgaatgtt ggaagatctg    300
ttggaacgag ttttccctac tcagagtgtc gaccagttac tggaaaagag aaccagtcta    360
tccggcaact ccacggggca ttctccatct tatccaaata gtaattccgt tccccccag     420 aattcctccc caaagttag cgactcttcc tcaacgactg ctgaacccgc tccagtcctt    480
ccatccaaac cctaatcttc attccgtcca atagttccag atgactactt cctgaatgat    540
gaaatcaacg gtttcgattg ggaggaggaa gacaccccag atcaattgtt ggtaatgcag    600
caacctccga catccgtcga ttccacgaat gtctcacatt cttactggaa tcatagccga    660
agatcgcaga aaaattccgt gacttcgttg aactcacttg cggagcacga acaatccggt    720
tgctcttcgt tgataacgtc ccccagccta cagccacttt tcagacaac aaccaatgat     780 tcccacccccg atgaatggc tgctcttttca gttaaccttta agggtggatc tggatatttt    840
gggttctctt caagttctgg acttctaagg gcattgaagc tgggtcaatt tgattccgct    900
tccatatctc ctatgagctc tgttaggaac tcggtctcca agactaatac tgaacctact    960
gaaccacaat caattcgttc tttactagga gatcccaatg acttttttgga acccgaaaag    1020 aaggctgaat cccaggcta cgattctcac ttaaatgacc ctaacaacca atcccaatat    1080
ctccaggcct acttcaagta ttatcacaca tcgtatcctt tcatccacaa aggatcattc    1140
ctcaaacatt atgctgggga gctaccaatc aagaatgaga accattggca gattttgctt    1200
aatgtcgtac ttgctctagg atgttggtgt ttgaatggag aatcttcctc gattgatctt    1260
tgctactaca atagagcaaa gatgctttta aagcaggtgg gtattttttga atgtggtaac    1320 attatgctgt tagagtcttt gattctcctt tcgaactata cgcagaagag aaataagcct    1380
aatacaggat ggagttactt aggtattgct attagaatgg ctatgtcttt agggctttac    1440
aaagagttca acttggacca tacagaaaag gaccactatc tcaacttaga aatcagaaga    1500
cggttatggt ggggtttgta cattttcgat gctggagctt caataacttt tggtcgtcct    1560 atcacttttac caagcagaga ttcgtgtgat attcaactgt gttccaatat caatgatgcc    1620
gagttggaag aattgatcga aataaaatcg gattcaatca ctactgagga ccttaacaaa    1680
ccatacccaa cagcatactc cggttttgatt cagcaaaccc agtttactga attatctatg    1740
aaaatttaca accgtttggt ttccaaacca gctccaactt gtgaagaatg tctagacatg    1800
aacatggaaa ttgaaaattt cataaagggt cttcccgctt acttccatga aagcaatgaa    1860
```

```
attgcaatgt ctcagttcta caaggttacg ccgtccaaat attacgatta tgacagcaac    1920
aaacaggtgg actatacccg cttaccgcaa tggtttgatc taagtcgaag tagattgatt    1980
tggagataca agaacctgca aattaccctt ttccgagcat ttatttggca acgagtcatt    2040
ggagtaacca atcccaaggt acttcaacag tgtaagacta gcagaggtaa ggaatgtcga    2100
actatttgtt tgagagttgc tcatgaaaca attttgtcta ttcaacagtt cgtgaatatt    2160
gacgatgatg atgacttctc tagactatcg gtcattggat gttggtatgc tacgtacttc    2220
ctattccagg ctgtcctgat tccaatcgct tgtctttgtt ctgaaccgga tagcaaatat    2280
gctccaattt ggatcgagga tattcaaatt agtaagaaga tcttcttgaa gctcaacaag    2340
ctcaactcgt tggcatctaa gtttgccaat gttattgaca gatcaatgag tcaagtaatg    2400
ccacagttcg acacaacaag cgccaaggac tctccactca acattaacga tttgatcgat    2460
atgcacggtc tcatgggtaa cagccccgct cctggttcta caacaatag caacaccaaa    2520 agcagcccca gcactaccaa caataccagg accccaaca ctatcaacaa aaacaacagt    2580
aacatgaaca ataatagtat caataactat tttaacaaca acagcaacaa caataactcc    2640
ttctccagtt cgaaggctgg accagtgaaa caggaatttg aagattactg tttaaagctg    2700
gaccctgaag acgaagacat gtctgcctta gagtttaccg cagttcgatt ccccaacttt    2760
tcagctacga caacagcccc gcctcctact ccagtcaatt gcaacagtcc tgaaaacatc    2820
aagacctcca ctgtggacga ttttttgaaa gctactcaag atccaaataa caaagagata    2880
ctcaacgaca tttacagttt gattttttgat gactccatgg atcctatgag cttcggaagt    2940
atggaaccaa gaaacgattt ggaagttccg gacactataa tggat                     2985

<210> SEQ ID NO 5
<211> LENGTH: 2985
<212> TYPE: DNA
<213> ORGANISM: Pichia pastoris

<400> SEQUENCE: 5
atgcatcata aagaaaagact catagatcat atttcttcgg agtctaactt ctcccttttcc    60 acttcgtcga tgccgtcctt cagccatgaa tcaaatcaat cgccgaaccc aatgctgatc    120
gaacaagctt gcgattcctg tcgtaagcgc aaattaaggt gttctaagga atacccaaag    180
tgttccaaat gtgtcaccca caaatggagt tgcgtttatt caccaaggac agtgagatct    240
ccgttgacga gagctcatct gaccaaagtg gaaaatcgtg tacgaatgtt ggaagatctg    300
ttggaacgag ttttccctac tcagagtgtc gaccagttac tggaaaagag aaccagtcta    360
tccggcaact ccacggggca ttctccatct tatccaaata gtaattccgt ttccccccag    420
aattcctccc aaaagttag cgactcttcc tcaacgactg ctgaacccgc tccagtcctt    480
ccatccaaac ccaaatcttc attccgtcca atagttccag atgactactt cctgaatgat    540
gaaatcaacg gttcgattg ggaggaggaa gacaccccag atcaattgtt ggtaatgcag    600
caacctccga catccgtcga ttccacgaat gtctcacatt cttactggaa tcatagccga    660
agatcgcaga aaaattccgt gacttcgttg aactcacttg cggagcacga acaatccggt    720
tgctcttcgt tgataacgtc ccccagccta cagccacttt ctcagacaac aaccaatgat    780
tcccaccccg atggaatggc tgctctttca gttaacctta agggtggatc tggatatttt    840
gggttctctt caagttctgg acttctaagg gcattgaagc tgggtcaatt tgattccgct    900
tccatatctc ctatgagctc tgttaggaac tcggtctcca agactaatac tgaacctact    960
```

```
gaaccacaat caattcgttc tttactagga gatcccaatg acttttttgga acccgaaaag    1020 aaggctgaat tcccaggcta cgattctcac ttaaatgacc ctaacaacca atcccaatat    1080
ctccaggcct acttcaagta ttatcacaca tcgtatcctt tcatccacaa aggatcattc    1140
ctcaaacatt atgctgggga gctaccaatc aagaatgaga accattggca gattttgctt    1200
aatgtcgtac ttgctctagg atgttggtgt ttgaatggag aatcttcctc gattgatctt    1260
tgctactaca atagagcaaa gatgctttta aagcaggtgg gtattttga atgtggtaac    1320 attatgctgt tagagtcttt gattctcctt tcgaactata cgcagaagag aaataagcct    1380
aatacaggat ggagttactt aggtattgct attagaatgg ctatgtcttt agggctttac    1440
aaagagttca acttggacca tacagaaaag gaccactatc tcaacttaga aatcagaaga    1500
cggttatggt ggggttttgta cattttcgat gctggagctt caataacttt tggtcgtcct    1560
atcactttac caagcagaga ttcgtgtgat attcaactgt gttccaatat caatgatgcc    1620
gagttggaag aattgatcga ataaaaatcg gattcaatca ctactgagga ccttaacaaa    1680
ccatacccaa cagcatactc cggtttgatt cagcaaaccc agtttactga attatctatg    1740
aaaatttaca accgtttggt ttccaaacca gctccaactg ttgaagaatg tctagacatg    1800
aacatggaaa ttgaaaattt cataaagggt cttcccgctt acttccatga aagcaatgaa    1860
attgcaatgt ctcagttcta caaggttacg ccgtccaaat attacgatta tgacagcaac    1920
aaacaggtgg actatacccg cttaccgcaa tggtttgatc taagttgaag tagattgatt    1980
tggagataca agaacctgca aattacccctt ttccgagcat ttatttggca acgagtcatt    2040
ggagtaacca atcccaaggt acttcaacag tgtaagacta gcagaggtaa ggaatgtcga    2100
actatttgtt tgagagttgc tcatgaaaca attttgtcta ttcaacagtt cgtgaatatt    2160
gacgatgatg atgacttctc tagactatcg gtcattggat gttggtatgc tacgtacttc    2220
ctattccagg ctgtcctgat tccaatcgct tgtctttgtt ctgaaccgga tagcaaatat    2280
gctccaattt ggatcgagga tattcaaatt agtaagaaga tcttcttgaa gctcaacaag    2340
ctcaactcgt tggcatctaa gtttgccaat gttattgaca gatcaatgag tcaagtaatg    2400
ccacagttcg acacaacaag cgccaaggac tctccactca acattaacga tttgatcgat    2460
atgcacggtc tcatgggtaa cagccccgct cctggttcta caacaatag caacaccaaa    2520 agcagcccca gcactaccaa caataccagg accccaacac ctatcaacaa aaacaacagt    2580
aacatgaaca ataatagtat caataactat tttaacaaca acagcaacaa caataactcc    2640
ttctccagtt cgaaggctgg accagtgaaa caggaatttg aagattactg tttaaagctg    2700
gaccctgaag acgaagacat gtctgcctta gagtttaccg cagttcgatt ccccaacttt    2760
tcagctacga caacagcccc gcctcctact ccagtcaatt gcaacagtcc tgaaaacatc    2820
aagacctcca ctgtggacga ttttttgaaa gctactcaag atccaaataa caaagagata    2880
ctcaacgaca tttacagttt gatttttgat gactccatgg atcctatgag cttcggaagt    2940
atggaaccaa gaaacgattt ggaagttccg gacactataa tggat              2985
```

<210> SEQ ID NO 6
<211> LENGTH: 1000
<212> TYPE: DNA
<213> ORGANISM: Pichia pastoris

<400> SEQUENCE: 6

```
gtatttgaca ggttggggag caaataagtg atgatgtccc atgaaagtag aaaatggcta      60
gtagaaggca aaaatttgaa attcttagag tcaaatagtt agactccaag ttctaatcca     120
```

```
catttggtca gtttcatagc atccagagct tttgccactg gtgaacatat ctacccattg      180
cgatgcaaca agtcactgaa agcctaaaac ggagattccc ctatcttaca gcctcgttca      240
aaaaaactgc taccgtttat ctgctatggc cgatgtgagg atgcgctcat gcccaagagt      300
ccaactttat caaaaacttg acccgtcata caggctctag atcaagaagc aaacttaatc      360
tcagcatctg gttacgtaac tctggcaacc agtaacacgc ttaaggtttg aacaacact       420 aaactacctt gcggtactac cattgacact acacatcctt aattccaatc ctgtctggcc      480
tccttcacct tttaaccatc ttgcccattc caactcgtgt cagattgcgt atcaagtgaa      540
aaaaaaaaaa ttttaaatct ttaacccaat caggtaataa ctgtcgcctc ttttatctgc      600
cgcactgcat gaggtgtccc cttagtggga agagtactg agccaaccct ggaggacagc       660
aagggaaaaa tacctacaac ttgcttcata atggtcgtaa aaacaatcct tgtcggatat      720
aagtgttgta gactgtccct tatcctctgc gatgttcttc ctctcaaagt ttgcgatttc      780
tctctatcag aattgccatc aagagactca ggactaattt cgcagtccca cacgcactcg      840
tacatgattg gctgaaattt ccctaaagaa tttcttttc acgaaaattt ttttttaca        900 caagattttc agcagatata aaatggagag caggacctcc gctgtgactc ttctttttt      960 tcttttattc tcactacata cattttagtt attcgccaac                          1000

<210> SEQ ID NO 7
<211> LENGTH: 995
<212> TYPE: PRT
<213> ORGANISM: Pichia pastoris

<400> SEQUENCE: 7

Met His His Lys Glu Arg Leu Ile Asp His Ile Ser Ser Glu Ser Asn
1               5                   10                  15

Phe Ser Leu Ser Thr Ser Ser Met Pro Ser Phe Ser His Glu Ser Asn
                20                  25                  30

Gln Ser Pro Asn Pro Met Leu Ile Glu Gln Ala Cys Asp Ser Cys Arg
            35                  40                  45

Lys Arg Lys Leu Arg Cys Ser Lys Glu Tyr Pro Lys Cys Ser Lys Cys
        50                  55                  60

Val Thr His Lys Trp Ser Cys Val Tyr Ser Pro Arg Thr Val Arg Ser
65                  70                  75                  80

Pro Leu Thr Arg Ala His Leu Thr Lys Val Glu Asn Arg Val Arg Met
                85                  90                  95

Leu Glu Asp Leu Leu Glu Arg Val Phe Pro Thr Gln Ser Val Asp Gln
            100                 105                 110

Leu Leu Glu Lys Arg Thr Ser Leu Ser Gly Asn Ser Thr Gly His Ser
        115                 120                 125

Pro Ser Tyr Pro Asn Ser Asn Ser Val Ser Pro Gln Asn Ser Ser Pro
    130                 135                 140

Lys Val Ser Asp Ser Ser Thr Thr Ala Glu Pro Ala Pro Val Leu
145                 150                 155                 160

Pro Ser Lys Pro Lys Ser Ser Phe Arg Pro Ile Val Pro Asp Tyr
                165                 170                 175

Phe Leu Asn Asp Glu Ile Asn Gly Phe Asp Trp Glu Glu Glu Asp Thr
            180                 185                 190

Pro Asp Gln Leu Leu Val Met Gln Gln Pro Thr Ser Val Asp Ser
        195                 200                 205

Thr Asn Val Ser His Ser Tyr Trp Asn His Ser Arg Arg Ser Gln Lys
```

```
            210                 215                 220
Asn Ser Val Thr Ser Leu Asn Ser Leu Ala Glu His Glu Gln Ser Gly
225                 230                 235                 240

Cys Ser Ser Leu Ile Thr Ser Pro Ser Leu Gln Pro Leu Ser Gln Thr
                    245                 250                 255

Thr Thr Asn Asp Ser His Pro Asp Gly Met Ala Ala Leu Ser Val Asn
                260                 265                 270

Leu Lys Gly Gly Ser Gly Tyr Phe Gly Phe Ser Ser Ser Gly Leu
                275                 280                 285

Leu Arg Ala Leu Lys Leu Gly Gln Phe Asp Ser Ala Ser Ile Ser Pro
        290                 295                 300

Met Ser Ser Val Arg Asn Ser Val Ser Lys Thr Asn Thr Glu Pro Thr
305                 310                 315                 320

Glu Pro Gln Ser Ile Arg Ser Leu Leu Gly Asp Pro Asn Asp Phe Leu
                    325                 330                 335

Glu Pro Glu Lys Lys Ala Glu Phe Pro Gly Tyr Asp Ser His Leu Asn
                340                 345                 350

Asp Pro Asn Asn Gln Ser Gln Tyr Leu Gln Ala Tyr Phe Lys Tyr Tyr
                    355                 360                 365

His Thr Ser Tyr Pro Phe Ile His Lys Gly Ser Phe Leu Lys His Tyr
        370                 375                 380

Ala Gly Glu Leu Pro Ile Lys Asn Glu Asn His Trp Gln Ile Leu Leu
385                 390                 395                 400

Asn Val Val Leu Ala Leu Gly Cys Trp Cys Leu Asn Gly Glu Ser Ser
                    405                 410                 415

Ser Ile Asp Leu Cys Tyr Tyr Asn Arg Ala Lys Met Leu Leu Lys Gln
                420                 425                 430

Val Gly Ile Phe Glu Cys Gly Asn Ile Met Leu Leu Glu Ser Leu Ile
            435                 440                 445

Leu Leu Ser Asn Tyr Thr Gln Lys Arg Asn Lys Pro Asn Thr Gly Trp
450                 455                 460

Ser Tyr Leu Gly Ile Ala Ile Arg Met Ala Met Ser Leu Gly Leu Tyr
465                 470                 475                 480

Lys Glu Phe Asn Leu Asp His Thr Glu Lys Asp His Tyr Leu Asn Leu
                485                 490                 495

Glu Ile Arg Arg Arg Leu Trp Trp Gly Leu Tyr Ile Phe Asp Ala Gly
                500                 505                 510

Ala Ser Ile Thr Phe Gly Arg Pro Ile Thr Leu Pro Ser Arg Asp Ser
            515                 520                 525

Cys Asp Ile Gln Leu Cys Ser Asn Ile Asn Asp Ala Glu Leu Glu Glu
        530                 535                 540

Leu Ile Glu Ile Lys Ser Asp Ser Ile Thr Thr Glu Asp Leu Asn Lys
545                 550                 555                 560

Pro Tyr Pro Thr Ala Tyr Ser Gly Leu Ile Gln Gln Thr Gln Phe Thr
                565                 570                 575

Glu Leu Ser Met Lys Ile Tyr Asn Arg Leu Val Ser Lys Pro Ala Pro
                580                 585                 590

Thr Val Glu Glu Cys Leu Asp Met Asn Met Glu Ile Glu Asn Phe Ile
                595                 600                 605

Lys Gly Leu Pro Ala Tyr Phe His Glu Ser Asn Glu Ile Ala Met Ser
            610                 615                 620

Gln Phe Tyr Lys Val Thr Pro Ser Lys Tyr Tyr Asp Tyr Asp Ser Asn
625                 630                 635                 640
```

```
Lys Gln Val Asp Tyr Thr Arg Leu Pro Gln Trp Phe Asp Leu Ser Arg
                645                 650                 655

Ser Arg Leu Ile Trp Arg Tyr Lys Asn Leu Gln Ile Thr Leu Phe Arg
            660                 665                 670

Ala Phe Ile Trp Gln Arg Val Ile Gly Val Thr Asn Pro Lys Val Leu
        675                 680                 685

Gln Gln Cys Lys Thr Ser Arg Gly Lys Glu Cys Arg Thr Ile Cys Leu
    690                 695                 700

Arg Val Ala His Glu Thr Ile Leu Ser Ile Gln Gln Phe Val Asn Ile
705                 710                 715                 720

Asp Asp Asp Asp Phe Ser Arg Leu Ser Val Ile Gly Cys Trp Tyr
                725                 730                 735

Ala Thr Tyr Phe Leu Phe Gln Ala Val Leu Ile Pro Ile Ala Cys Leu
            740                 745                 750

Cys Ser Glu Pro Asp Ser Lys Tyr Ala Pro Ile Trp Ile Glu Asp Ile
        755                 760                 765

Gln Ile Ser Lys Lys Ile Phe Leu Lys Leu Asn Lys Leu Asn Ser Leu
    770                 775                 780

Ala Ser Lys Phe Ala Asn Val Ile Asp Arg Ser Met Ser Gln Val Met
785                 790                 795                 800

Pro Gln Phe Asp Thr Thr Ser Ala Lys Asp Ser Pro Leu Asn Ile Asn
                805                 810                 815

Asp Leu Ile Asp Met His Gly Leu Met Gly Asn Ser Pro Ala Pro Gly
            820                 825                 830

Ser Asn Asn Ser Asn Thr Lys Ser Ser Pro Ser Thr Thr Asn Asn
        835                 840                 845

Thr Arg Thr Pro Asn Thr Ile Asn Lys Asn Asn Ser Asn Met Asn Asn
    850                 855                 860

Asn Ser Ile Asn Asn Tyr Phe Asn Asn Asn Ser Asn Asn Asn Asn Ser
865                 870                 875                 880

Phe Ser Ser Ser Lys Ala Gly Pro Val Lys Gln Glu Phe Glu Asp Tyr
                885                 890                 895

Cys Leu Lys Leu Asp Pro Glu Asp Glu Asp Met Ser Ala Leu Glu Phe
            900                 905                 910

Thr Ala Val Arg Phe Pro Asn Phe Ser Ala Thr Thr Ala Pro Pro
        915                 920                 925

Pro Thr Pro Val Asn Cys Asn Ser Pro Glu Asn Ile Lys Thr Ser Thr
    930                 935                 940

Val Asp Asp Phe Leu Lys Ala Thr Gln Asp Pro Asn Asn Lys Glu Ile
945                 950                 955                 960

Leu Asn Asp Ile Tyr Ser Leu Ile Phe Asp Asp Ser Met Asp Pro Met
                965                 970                 975

Ser Phe Gly Ser Met Glu Pro Arg Asn Asp Leu Glu Val Pro Asp Thr
            980                 985                 990

Ile Met Asp
        995

<210> SEQ ID NO 8
<211> LENGTH: 40
<212> TYPE: PRT
<213> ORGANISM: Pichia pastoris

<400> SEQUENCE: 8

Met His His Lys Glu Arg Leu Ile Asp His Ile Ser Ser Glu Ser Asn
```

```
                1               5                   10                  15
              Phe Ser Leu Ser Thr Ser Ser Met Pro Ser Phe Ser His Glu Ser Asn
                              20                  25                  30

Gln Ile Asn Arg Arg Thr Gln Cys
                              35                  40

<210> SEQ ID NO 9
<211> LENGTH: 107
<212> TYPE: PRT
<213> ORGANISM: Pichia pastoris

<400> SEQUENCE: 9

Met His His Lys Glu Arg Leu Ile Asp His Ile Ser Ser Glu Ser Asn
 1               5                  10                  15

Phe Ser Leu Ser Thr Ser Ser Met Pro Ser Phe Ser His Glu Ser Asn
                20                  25                  30

Gln Ser Pro Asn Pro Met Leu Ile Glu Gln Ala Cys Asp Ser Cys Arg
                35                  40                  45

Lys Arg Lys Leu Arg Cys Ser Lys Glu Tyr Pro Lys Cys Ser Lys Cys
        50                  55                  60

Val Thr His Lys Trp Ser Cys Val Tyr Ser Pro Arg Thr Val Arg Ser
 65                  70                  75                  80

Pro Leu Thr Arg Ala His Leu Thr Lys Val Glu Asn Arg Val Arg Met
                85                  90                  95

Leu Glu Asp Leu Leu Glu Arg Val Phe Pro Thr
                100                 105

<210> SEQ ID NO 10
<211> LENGTH: 164
<212> TYPE: PRT
<213> ORGANISM: Pichia pastoris

<400> SEQUENCE: 10

Met His His Lys Glu Arg Leu Ile Asp His Ile Ser Ser Glu Ser Asn
 1               5                  10                  15

Phe Ser Leu Ser Thr Ser Ser Met Pro Ser Phe Ser His Glu Ser Asn
                20                  25                  30

Gln Ser Pro Asn Pro Met Leu Ile Glu Gln Ala Cys Asp Ser Cys Arg
                35                  40                  45

Lys Arg Lys Leu Arg Cys Ser Lys Glu Tyr Pro Lys Cys Ser Lys Cys
        50                  55                  60

Val Thr His Lys Trp Ser Cys Val Tyr Ser Pro Arg Thr Val Arg Ser
 65                  70                  75                  80

Pro Leu Thr Arg Ala His Leu Thr Lys Val Glu Asn Arg Val Arg Met
                85                  90                  95

Leu Glu Asp Leu Leu Glu Arg Val Phe Pro Thr Gln Ser Val Asp Gln
                100                 105                 110

Leu Leu Glu Lys Arg Thr Ser Leu Ser Gly Asn Ser Thr Gly His Ser
        115                 120                 125

Pro Ser Tyr Pro Asn Ser Asn Ser Val Ser Pro Gln Asn Ser Ser Pro
        130                 135                 140

Lys Val Ser Asp Ser Ser Ser Thr Thr Ala Glu Pro Ala Pro Val Leu
145                 150                 155                 160

Pro Ser Lys Pro

<210> SEQ ID NO 11
```

```
<211> LENGTH: 655
<212> TYPE: PRT
<213> ORGANISM: Pichia pastoris

<400> SEQUENCE: 11
```

| | | | | | | | | | | | | | | |
|---|---|---|---|---|---|---|---|---|---|---|---|---|---|---|
Met His His Lys Glu Arg Leu Ile Asp His Ile Ser Ser Glu Ser Asn
1               5                   10                  15

Phe Ser Leu Ser Thr Ser Ser Met Pro Ser Phe Ser His Glu Ser Asn
            20                  25                  30

Gln Ser Pro Asn Pro Met Leu Ile Glu Gln Ala Cys Asp Ser Cys Arg
        35                  40                  45

Lys Arg Lys Leu Arg Cys Ser Lys Glu Tyr Pro Lys Cys Ser Lys Cys
50              55                  60

Val Thr His Lys Trp Ser Cys Val Tyr Ser Pro Arg Thr Val Arg Ser
65              70                  75                  80

Pro Leu Thr Arg Ala His Leu Thr Lys Val Glu Asn Arg Val Arg Met
                85                  90                  95

Leu Glu Asp Leu Leu Glu Arg Val Phe Pro Thr Gln Ser Val Asp Gln
            100                 105                 110

Leu Leu Glu Lys Arg Thr Ser Leu Ser Gly Asn Ser Thr Gly His Ser
        115                 120                 125

Pro Ser Tyr Pro Asn Ser Asn Ser Val Ser Pro Gln Asn Ser Ser Pro
    130                 135                 140

Lys Val Ser Asp Ser Ser Ser Thr Thr Ala Glu Pro Ala Pro Val Leu
145                 150                 155                 160

Pro Ser Lys Pro Lys Ser Ser Phe Arg Pro Ile Val Pro Asp Asp Tyr
                165                 170                 175

Phe Leu Asn Asp Glu Ile Asn Gly Phe Asp Trp Glu Glu Glu Asp Thr
            180                 185                 190

Pro Asp Gln Leu Leu Val Met Gln Gln Pro Thr Ser Val Asp Ser
        195                 200                 205

Thr Asn Val Ser His Ser Tyr Trp Asn His Ser Arg Arg Ser Gln Lys
    210                 215                 220

Asn Ser Val Thr Ser Leu Asn Ser Leu Ala Glu His Glu Gln Ser Gly
225                 230                 235                 240

Cys Ser Ser Leu Ile Thr Ser Pro Ser Leu Gln Pro Leu Ser Gln Thr
                245                 250                 255

Thr Thr Asn Asp Ser His Pro Asp Gly Met Ala Ala Leu Ser Val Asn
            260                 265                 270

Leu Lys Gly Gly Ser Gly Tyr Phe Gly Phe Ser Ser Ser Ser Gly Leu
        275                 280                 285

Leu Arg Ala Leu Lys Leu Gly Gln Phe Asp Ser Ala Ser Ile Ser Pro
    290                 295                 300

Met Ser Ser Val Arg Asn Ser Val Ser Lys Thr Asn Thr Glu Pro Thr
305                 310                 315                 320

Glu Pro Gln Ser Ile Arg Ser Leu Leu Gly Asp Pro Asn Asp Phe Leu
                325                 330                 335

Glu Pro Glu Lys Lys Ala Glu Phe Pro Gly Tyr Asp Ser His Leu Asn
            340                 345                 350

Asp Pro Asn Asn Gln Ser Gln Tyr Leu Gln Ala Tyr Phe Lys Tyr Tyr
        355                 360                 365

His Thr Ser Tyr Pro Phe Ile His Lys Gly Ser Phe Leu Lys His Tyr
    370                 375                 380

Ala Gly Glu Leu Pro Ile Lys Asn Glu Asn His Trp Gln Ile Leu Leu

```
            385                 390                 395                 400
    Asn Val Val Leu Ala Leu Gly Cys Trp Cys Leu Asn Gly Glu Ser Ser
                    405                 410                 415

Ser Ile Asp Leu Cys Tyr Tyr Asn Arg Ala Lys Met Leu Leu Lys Gln
                420                 425                 430

Val Gly Ile Phe Glu Cys Gly Asn Ile Met Leu Leu Glu Ser Leu Ile
                435                 440                 445

Leu Leu Ser Asn Tyr Thr Gln Lys Arg Asn Lys Pro Asn Thr Gly Trp
    450                 455                 460

Ser Tyr Leu Gly Ile Ala Ile Arg Met Ala Met Ser Leu Gly Leu Tyr
    465                 470                 475                 480

Lys Glu Phe Asn Leu Asp His Thr Glu Lys Asp His Tyr Leu Asn Leu
                    485                 490                 495

Glu Ile Arg Arg Arg Leu Trp Trp Gly Leu Tyr Ile Phe Asp Ala Gly
                500                 505                 510

Ala Ser Ile Thr Phe Gly Arg Pro Ile Thr Leu Pro Ser Arg Asp Ser
                515                 520                 525

Cys Asp Ile Gln Leu Cys Ser Asn Ile Asn Asp Ala Glu Leu Glu Glu
    530                 535                 540

Leu Ile Glu Ile Lys Ser Asp Ser Ile Thr Thr Glu Asp Leu Asn Lys
    545                 550                 555                 560

Pro Tyr Pro Thr Ala Tyr Ser Gly Leu Ile Gln Gln Thr Gln Phe Thr
                    565                 570                 575

Glu Leu Ser Met Lys Ile Tyr Asn Arg Leu Val Ser Lys Pro Ala Pro
                580                 585                 590

Thr Val Glu Glu Cys Leu Asp Met Asn Met Glu Ile Glu Asn Phe Ile
                595                 600                 605

Lys Gly Leu Pro Ala Tyr Phe His Glu Ser Asn Glu Ile Ala Met Ser
                610                 615                 620

Gln Phe Tyr Lys Val Thr Pro Ser Lys Tyr Tyr Asp Tyr Asp Ser Asn
    625                 630                 635                 640

Lys Gln Val Asp Tyr Thr Arg Leu Pro Gln Trp Phe Asp Leu Ser
                    645                 650                 655

<210> SEQ ID NO 12
<211> LENGTH: 20
<212> TYPE: DNA
<213> ORGANISM: Pichia pastoris

<400> SEQUENCE: 12
tttcgaaagt ggcttggaat                                                    20

<210> SEQ ID NO 13
<211> LENGTH: 19
<212> TYPE: DNA
<213> ORGANISM: Pichia pastoris

<400> SEQUENCE: 13
tggggagaag gtaccgaag                                                     19

<210> SEQ ID NO 14
<211> LENGTH: 20
<212> TYPE: DNA
<213> ORGANISM: Pichia pastoris

<400> SEQUENCE: 14
cactacgcgt actgtgagcc                                                    20
```

```
<210> SEQ ID NO 15
<211> LENGTH: 20
<212> TYPE: DNA
<213> ORGANISM: Pichia pastoris

<400> SEQUENCE: 15
gcttggtacg gtagcctcaa                                              20

<210> SEQ ID NO 16
<211> LENGTH: 20
<212> TYPE: DNA
<213> ORGANISM: Pichia pastoris

<400> SEQUENCE: 16
agtctgcgct ttccatgtct                                              20

<210> SEQ ID NO 17
<211> LENGTH: 20
<212> TYPE: DNA
<213> ORGANISM: Pichia pastoris

<400> SEQUENCE: 17
ggcctggaga tattgggatt                                              20

<210> SEQ ID NO 18
<211> LENGTH: 10
<212> TYPE: DNA
<213> ORGANISM: Pichia pastoris
<220> FEATURE:
<221> NAME/KEY: misc_feature
<223> OTHER INFORMATION: unknown nucleic acid
<220> FEATURE:
<221> NAME/KEY: misc_feature
<222> LOCATION: (7)..(10)
<223> OTHER INFORMATION: n is a, c, g, or t

<400> SEQUENCE: 18 tgaatcnnnn                                                         10

<210> SEQ ID NO 19
<211> LENGTH: 24
<212> TYPE: DNA
<213> ORGANISM: Pichia pastoris

<400> SEQUENCE: 19
cagatcttcc aacattcgta cacg                                         24

<210> SEQ ID NO 20
<211> LENGTH: 28
<212> TYPE: DNA
<213> ORGANISM: Pichia pastoris

<400> SEQUENCE: 20
gcttactttc ataattgcga ctggttcc                                     28

<210> SEQ ID NO 21
<211> LENGTH: 26
<212> TYPE: DNA
<213> ORGANISM: Pichia pastoris

<400> SEQUENCE: 21
cgcagtccca cacgcactcg tacatg                                       26
```

<210> SEQ ID NO 22
<211> LENGTH: 934
<212> TYPE: DNA
<213> ORGANISM: Pichia pastoris

<400> SEQUENCE: 22

| | | | | | |
|---|---|---|---|---|---|
| aacatccaaa | gacgaaaggt | tgaatgaaac | cttttttgcca | tccgacatcc | acaggtccat | 60 |
| tctcacacat | aagtgccaaa | cgcaacagga | ggggatacac | tagcagcaga | ccgttgcaaa | 120 |
| cgcaggacct | ccactcctct | tctcctcaac | acccacttttt | gccatcgaaa | aaccagccca | 180 |
| gttattgggc | ttgattggag | ctcgctcatt | ccaattcctt | ctattaggct | actaacacca | 240 |
| tgactttatt | agcctgtcta | tcctggcccc | cctggcgagg | ttcatgtttg | tttatttccg | 300 |
| aatgcaacaa | gctccgcatt | acacccgaac | atcactccag | atgagggctt | tctgagtgtg | 360 |
| gggtcaaata | gtttcatgtt | ccccaaatgg | cccaaaactg | acagtttaaa | cgctgtcttg | 420 |
| gaacctaata | tgacaaaagc | gtgatctcat | ccaagatgaa | ctaagtttgg | ttcgttgaaa | 480 |
| tgctaacggc | cagttggtca | aaaagaaact | tccaaaagtc | ggcataccgt | ttgtcttgtt | 540 |
| tggtattgat | tgacgaatgc | tcaaaaataa | tctcattaat | gcttagcgca | gtctctctat | 600 |
| cgcttctgaa | ccccggtgca | cctgtgccga | aacgcaaatg | gggaaacacc | cgcttttttgg | 660 |
| atgattatgc | attgtctcca | cattgtatgc | ttccaagatt | ctggtgggaa | tactgctgat | 720 |
| agcctaacgt | tcatgatcaa | aatttaactg | ttctaacccc | tacttgacag | caatatataa | 780 |
| acagaaggaa | gctgccctgt | cttaaaacctt | tttttttatc | atcattatta | gcttactttc | 840 |
| ataattgcga | ctggttccaa | ttgacaagct | tttgatttta | acgacttttta | acgacaactt | 900 |
| gagaagatca | aaaacaact | aattattcga | aacg | | | 934 |

<210> SEQ ID NO 23
<211> LENGTH: 1111
<212> TYPE: PRT
<213> ORGANISM: H. polymorpha

<400> SEQUENCE: 23

Met Glu Gly Ile Ser Lys Pro Val Gly Phe Gly Glu Asn Lys Glu Ser
1               5                   10                  15

Met Val Lys Arg Glu Leu Ser Asp Glu Asp Leu Phe Val Leu Glu Ser
                20                  25                  30

Arg Leu Ser Glu Ser Ala Ser Ala Asn Leu Thr Asn Ser Pro Ser
            35                  40                  45

Pro Pro Gln Asn Ser Asn Leu Ser Asn Gly His Ser Thr Lys Pro Thr
        50                  55                  60

Ile Ser Arg Thr Thr Ser Ser Gly Ser Ser Tyr Val His Arg Gln His
65                  70                  75                  80

Thr Pro Ser His Gly His Gly Ser Arg His Leu Ala His His His
                85                  90                  95

Asn Asn Ser Val Phe Pro Gln Arg Thr Ile Lys Arg Glu Pro Ser Asp
            100                 105                 110

Ser Leu Glu Asp Asp Ala Ile Glu Glu Ala Glu Gly Tyr Glu Asn Lys
        115                 120                 125

Ser His Ser Arg Asn Lys Pro Leu Ile Glu Gln Ala Cys Asp Ser Cys
    130                 135                 140

Arg Arg Arg Lys Leu Arg Cys Thr Lys Glu Leu Pro Lys Cys Ser Lys
145                 150                 155                 160

Cys Met Asp His Gly Trp Glu Cys Val Tyr Ser Pro Arg Ala Val Arg
                165                 170                 175

```
Ser Pro Leu Thr Arg Ala Tyr Leu Thr Lys Val Glu Asn Arg Val Lys
            180                 185                 190

Gln Leu Glu Thr Phe Leu Leu Lys Ala Phe Pro Gly Glu Asp Leu Glu
            195                 200                 205

Gln Met Leu Gly Gly Phe Ser Arg Thr Gly Ser Ser Ile Gln Ser Leu
210                 215                 220

Cys Asn Ser Pro Asn Met Ser Ala Tyr Ser Leu Leu Ser Gln Asn Lys
225                 230                 235                 240

Gln His Cys Asp Asn Thr Ser Ser Thr Gln Thr Met Gln Asp Phe Ser
                245                 250                 255

Leu Asp Ala Ser Ser Thr Ser Ile Phe Lys Lys Glu Thr Pro Gln Gln
            260                 265                 270

Ile Leu Ser Arg Leu Pro Asp Glu Phe Met Ala Thr Asp Leu Ser Asn
            275                 280                 285

Asn Thr Asn Phe Asp Trp Ser Glu Asp Glu Glu Arg Glu Lys Gly
            290                 295                 300

Leu Met Met Asn Gly Ser Pro Ser Ser Pro Ser Ser Ile Thr Ser Leu
305                 310                 315                 320

His Glu Pro Lys Asn Ser Val Ile Ser Phe Asn Ser Leu Asp His Leu
                325                 330                 335

His Thr Ser Gln Ala Gln Ser Ser Thr Ile Ser Thr Lys Thr Asn Asn
            340                 345                 350

Ser Ser Leu Cys Thr Ser Pro Tyr Leu Arg Ala Val Ala Pro Ser Phe
            355                 360                 365

Ser Thr Asp Gly Met Gly Val Asn Pro Thr Thr Lys Ser Gly Phe Leu
            370                 375                 380

Gly Val Gly Ser Ser Ser Phe Leu Arg Val Met Lys Ile Asp Lys
385                 390                 395                 400

Ile Asp Glu Glu Asp Val Ala Asp Phe Val Asn Ser Gly Ala Thr Asp
                405                 410                 415

Thr Asp Phe Val Met Asp Asp Phe Asp Leu Thr Ser Cys Asn Asn Ser
            420                 425                 430

Ser Glu Thr Arg Lys Pro Met Lys Ser Pro Asn Val Thr Met Asn
            435                 440                 445

Pro Gln Ile Lys Lys Gln Ile Val Glu Gly Leu Lys Arg Gly Leu Asp
450                 455                 460

Asn Met Glu Gln Asn Lys Ile Gly Glu Glu Leu Glu Gln Tyr Leu Asn
465                 470                 475                 480

Met Arg Ser Thr Gln Glu Glu Phe Leu Gln Ser Tyr Phe Arg Tyr Tyr
                485                 490                 495

His Thr Ser Tyr Pro Phe Ile His Lys Glu Thr Phe Met Lys His Tyr
            500                 505                 510

Arg Lys Gln Leu Pro Val Lys Asn Glu Ala His Trp Leu Val Leu Phe
            515                 520                 525

Asn Thr Val Leu Ala Leu Gly Cys Trp Cys Leu His Gly Asp His Thr
            530                 535                 540

Thr Ile Asp Leu Ala Tyr Tyr His Arg Ala Lys Lys Ala Leu Asn Thr
545                 550                 555                 560

Gly Ala Asn Val Phe Glu Cys Gly Asn Ile Met Leu Leu Ser Ala Leu
                565                 570                 575

Ile Leu Leu Ser Asn Tyr Ser Gln Lys Arg Asn Lys Pro Asn Thr Gly
            580                 585                 590
```

```
Trp Asn Phe Leu Gly Leu Ala Val Arg Met Ala Ile Ser Leu Gly Met
            595                 600                 605

His Lys Glu Phe Asn Glu Gln Ser Asn Ser Arg Glu Thr Arg Lys Glu
    610                 615                 620

Asp Leu Leu Asn Leu Glu Ile Lys Arg Arg Leu Trp Trp Gly Leu Tyr
625                 630                 635                 640

Ile Phe Asp Ala Gly Ala Ser Ile Thr Phe Gly Arg Pro Ile Asn Leu
                645                 650                 655

Pro Pro Pro Glu Val Val Asp Val Lys Met Val Ser Asn Ile Asn Asp
            660                 665                 670

Asp Glu Leu Ser Gln Ile Ile Glu Asn Met Asp Gly Cys Asn Thr Val
        675                 680                 685

Thr Glu Glu Met Ile Asn Lys Pro Tyr Pro Thr Leu Tyr Ser Ala Leu
    690                 695                 700

Ile Ala Gln Thr Lys Leu Thr Phe Leu Thr Thr Pro Phe Tyr Ser Lys
705                 710                 715                 720

Leu Ile Ser Lys Pro Ala Pro Thr Leu Gln Glu Cys Phe Ser Met Asn
                725                 730                 735

Ala Thr Leu Glu Lys Phe Ile Asp Glu Leu Pro Gly Tyr Phe His Glu
            740                 745                 750

Asp Glu Ser Val Ala Lys Arg Glu Phe Phe Asn Ser Leu Pro Thr Asn
        755                 760                 765

Leu Arg Gln Ser Thr Asn Glu Ser His Leu Pro Glu Trp Phe Leu Leu
    770                 775                 780

Ser Arg Asn Arg Leu Ile Trp Arg Tyr Arg Asn Met Gln Ile Ile Leu
785                 790                 795                 800

Phe Arg Pro Phe Ile Trp Gln Arg Ile Val Gly Ile Ser Asn Pro Glu
                805                 810                 815

Val Met Glu Ser Cys Lys Thr Glu Glu Ala Lys Glu Gly Arg Arg Ile
            820                 825                 830

Cys Leu Lys Ala Ala Ser Glu Thr Ile Lys Ser Ile Asp Lys Phe Val
        835                 840                 845

Lys Asp Asn Glu Ser His Leu Ser Ile Ile Ala Val Trp Tyr Ala Thr
    850                 855                 860

Tyr Phe Leu Phe Gln Ala Val Leu Ile Pro Ile Ala Cys Leu Cys Ser
865                 870                 875                 880

Asp Ser Ser Ser His Ser Thr Ser Trp Met Asp Ile Asn Arg
                885                 890                 895

Ala Lys Asn Ala Leu Leu Val Met Ser Lys Tyr Asn Ser Met Gly Ser
            900                 905                 910

Lys Leu Thr Lys Val Ile Asn Lys Leu Leu Gly Gln Lys Ser Thr Pro
        915                 920                 925

Ser Asn Ser Lys Gln Thr Ala Pro Ser Glu Lys Gln Phe Ala Ser Tyr
    930                 935                 940

Pro Val Thr Lys Val Asn Ser Ser Ser Asn Asp Ser Leu Tyr Ser
945                 950                 955                 960

His Pro Ser Ser Cys Phe Ala Asn Gln Arg Tyr Pro Thr Thr Val Ser
                965                 970                 975

Phe Asp Gly Ser Lys Leu Ala Lys Leu Thr Glu Pro Ser Lys Asn Phe
            980                 985                 990

Met Asp Asn Val Ser Glu Asp Ile Ser Ala Gln Asn Met Glu Ser Phe
        995                 1000                1005

Val Ser Leu Asp Thr Tyr Leu Asn Leu Asp Thr Asp Asn Thr Pro
```

```
            1010                1015                1020

Asp Ser  Ala Met Phe Asp Phe  Glu Lys Lys Arg Lys  Leu Ser Asn
    1025                1030                1035

Ala Glu  Asn Met Lys Pro Phe  Asn Ser Ser Thr Ser  Leu Phe
    1040                1045                1050

Asn Thr  Gly His Thr Thr Ser  Ala Ser Asn Ser Val  Ala Thr Leu
    1055                1060                1065

Asn Asn  Phe Asp Leu Asp Pro  Gly Thr Glu His Lys  Asp Lys Glu
    1070                1075                1080

Gln His  Ser Asn Lys Lys Glu  Leu Leu Asn Asp Ile  Tyr Ser Met
    1085                1090                1095

Leu Phe  Asp Glu Phe Thr Asp  Pro Met Ala Phe Ser  Val
    1100                1105                1110

<210> SEQ ID NO 24
<211> LENGTH: 776
<212> TYPE: PRT
<213> ORGANISM: Pichia stipitis

<400> SEQUENCE: 24

Met Ser Val Ser Thr Arg Ser Pro Asn Thr His Gln Ala Cys Asp Ser
1               5                   10                  15

Cys Arg Leu Arg Lys Met Lys Cys Ser Lys Glu Tyr Pro Gln Cys Gln
            20                  25                  30

Lys Cys Lys Glu Gln Asn Trp Lys Cys Val Tyr Ser Leu Lys Thr Ile
        35                  40                  45

Arg Ser Pro Leu Thr Arg Thr His Leu Ser Lys Val Glu Asp Arg Val
    50                  55                  60

Lys Ala Leu Glu Lys Leu Leu Val Arg Leu Leu Pro Gly Asp Val Glu
65                  70                  75                  80

Ile Asn Asp Leu Leu Arg Ala Ser Glu Ser Asn Ser Asp Ile Lys Glu
                85                  90                  95

Glu Val Glu Thr Ile Asp Asn Pro Gln Phe Tyr Lys Gln Ile Ser Leu
            100                 105                 110

Thr Thr Glu Asp Leu Ser Asn Ile Pro Ile Thr Phe Lys Asn Ile Asn
        115                 120                 125

Lys Ile Ser Arg Glu Lys Val Gln Lys Thr Pro Ser Glu Gln Thr Leu
    130                 135                 140

Asp Tyr Gln Pro Glu Asp Tyr Leu Ile Asp Leu Glu Lys Ser Asp Leu
145                 150                 155                 160

Asn Gln Tyr Asp Glu Arg Glu Asp Ser Leu Asn Asn Asn Ile Ser Asn
                165                 170                 175

Ile Asp Gln Pro Leu Tyr Ser Pro Asn Thr Asp Gly Met Ala Val Leu
            180                 185                 190

Ser Asn Asp Ile Gly Leu Asn Tyr Asp Ser Pro Lys Ser Asn Gly Tyr
        195                 200                 205

Phe Gly Ile Asn Ser Thr Asn Gly Leu Leu Lys Phe Leu Ser Leu Lys
    210                 215                 220

Ser Lys Lys Thr Gly Gly Lys Asp Val Val Leu Asn Leu Asn Asn Phe
225                 230                 235                 240

Ser Tyr Asn Asp Asp Glu Glu Glu Glu Ala Ala Thr Val Leu Asp
                245                 250                 255

Val His Leu Asn Glu Ile Trp Lys Gly Ile Asn Ser Gly Arg Ile Ala
            260                 265                 270
```

```
Asp Leu Leu Asp Asn Ala Ala Phe Gln Thr Leu Ala Val Ser Ser Tyr
            275                 280                 285

Phe Asp Ile Tyr His Asn Ala Tyr Pro Phe Val Asp Lys Ser Lys Phe
    290                 295                 300

Met Lys Gln Phe Asn Ala Met Ile Ser Gly Asp Asn Pro Ser Glu Tyr
305                 310                 315                 320

Asp Tyr Ala Lys Ile Glu Asp Asn Glu Lys Lys Leu Ser Phe His Val
                325                 330                 335

Leu Leu Asn Thr Ile Leu Ala Ile Gly Ile Trp Cys Ile Ser Gly Glu
            340                 345                 350

Ser Ser Arg Val His Thr Tyr Tyr Gln Arg Val Lys Asn Leu Leu
            355                 360                 365

Gln Leu Ile Asn Val Phe Glu Tyr Ser Asp Ser Gln Leu Phe Val Ser
    370                 375                 380

Tyr Val Leu Leu Ser Asn Tyr Val Gln Lys Asn Asn Lys Pro Asn Thr
385                 390                 395                 400

Gly Trp Ser Tyr Leu Gly Leu Ser Ala Arg Val Ala Thr Ala Leu Gly
                405                 410                 415

Leu His Lys Glu Val Lys Leu Asp Gln Phe Ile Asp His Thr Asn Gly
            420                 425                 430

Asp Ser Pro Arg Thr Asn Leu Lys Leu Tyr Lys Glu Ile Glu His Arg
    435                 440                 445

Lys Arg Leu Trp Trp Gly Met Tyr Phe Phe Asp Val Gly Thr Thr Leu
450                 455                 460

Thr Phe Gly Arg Pro Leu Thr Ile Pro Ala Leu Asn Thr Ile Asp Leu
465                 470                 475                 480

Glu Pro Val Leu Asn Ile Asp Asp Ile Leu Asn Tyr Gly Asn Met
                485                 490                 495

Ser Arg Ile Glu Asp Ala Glu Val Lys Tyr Pro Thr Ile Tyr Thr Gly
            500                 505                 510

Leu Ile Tyr Glu Ser Glu Leu Thr Lys Ile Ser Thr Arg Ile Tyr Asn
            515                 520                 525

Tyr Asn Ser Ser Val Leu Lys Leu Lys Asn Asp Leu Ser Lys Met Ile
    530                 535                 540

Gly Leu Leu Asp Met Asn Glu Leu Leu Glu Asp Phe Val Gly Lys Leu
545                 550                 555                 560

Pro Leu Tyr Phe Asn Gln Asn Asp Glu Ile Ser Thr Pro Asn Leu Tyr
                565                 570                 575

Gln Gln Trp Gln Asn Thr Lys Tyr Ala Ala Gln Pro Ile Pro Lys Trp
            580                 585                 590

Phe Ser Leu Thr Arg Leu Arg Leu Asn Cys Arg Ile Lys Asn Leu Gln
    595                 600                 605

Met Leu Ile Phe Arg Tyr Ile Leu Trp Glu Ser Asn Glu Gly Phe Glu
610                 615                 620

Asp Pro Asn Phe Ile Ala Leu Ile Lys Arg Cys Arg Asn Ile Cys Phe
625                 630                 635                 640

Lys Ser Ser Val Glu Thr Ile Glu Met Val Ala Lys Phe Leu Glu Lys
            645                 650                 655

Phe Glu Ile Asp Arg Leu Thr Ala Trp Tyr Leu Thr Tyr Phe Leu Phe
            660                 665                 670

Gln Ala Val Leu Val Pro Ile Leu Lys Leu Gly Ile Lys Asp Ile Gly
    675                 680                 685

Leu Asp Arg Thr Asp Glu Val Tyr Tyr Arg Thr Asp Asp Val Ile Ser
```

```
                690               695               700
Arg Tyr Ile Asp Ile Ser Gln Arg Ser Phe Asn Lys Leu Lys Pro Tyr
705                 710               715               720

Asn Lys Leu Ala Gly Lys Phe Val Lys Ile Ile Asp Ile Leu Thr Thr
                    725               730               735

Lys Asp Arg Glu Ala Thr Ile Asn Tyr Glu Ser Leu Phe Ala Ile Glu
                740               745               750

Pro Asn Asn Val Ser Leu Phe Asp Ser Met Glu Asp Phe Phe Asn Phe
                755               760               765

Glu Asn Asp Val Met Gln Phe Lys
                770               775

<210> SEQ ID NO 25
<211> LENGTH: 674
<212> TYPE: PRT
<213> ORGANISM: Pichia guilliermondii

<400> SEQUENCE: 25

Met Thr Glu Ser Pro Gln Arg Lys Arg Val Cys Glu Asp Asn Asp Ser
1               5                   10                  15

Gln Phe Ala Cys Asn Glu Cys Lys Arg Arg Leu Lys Cys Ser Arg
            20                  25                  30

Asp Val Pro Thr Cys Ser Leu Cys Leu Lys His His Arg His Cys Leu
                35                  40                  45

Tyr Glu Lys Thr Asn Arg Ser Pro Leu Thr Arg Lys His Leu Thr Gln
        50                  55                  60

Val Glu Glu Glu Leu Arg Ile Ser Arg Lys Val Ile Gln Arg His Phe
65                  70                  75                  80

Pro Thr Met Asp Ile Ser Arg Met Val Gln Glu Ile Lys Asn Gly Ser
                85                  90                  95

Asn Ile Asp Glu Leu Ile Asp Leu Phe Thr Thr Gln Ser Ser Pro
            100                 105                 110

Thr Gln Lys Asn Ser Ser Pro Thr Lys Asn Asn Ile Lys Asn Leu Leu
        115                 120                 125

Thr Ile Asp Asp Gly Leu Glu Asp Leu Gln Val Pro Gln Leu Val Pro
    130                 135                 140

Ser Ser Val Thr Glu Asn Gly Ser His Lys Ser Ser Thr Asp Leu Ser
145                 150                 155                 160

Pro Val Ser Tyr Asn Trp Asp Glu Arg Asn Leu Pro His Gly Asn Arg
                165                 170                 175

Gln Ala Ser Ile Ile Asp Gly Ile Ala Thr Met Asp Thr Asn Gly Tyr
            180                 185                 190

Leu Gly Ser Pro Ser Ser Ala Ala Leu Ile Asn Leu Val Gly Gly Gly
        195                 200                 205

Phe Phe Phe His Lys Pro His Gly Asp Gly Asp Gly Asn His Val
    210                 215                 220

Asn Glu Glu Val Leu Thr Asn Ile Pro Arg Asn Thr Leu Glu Gly Tyr
225                 230                 235                 240

Ile Asn Gln Tyr Phe Gln Thr Phe His Val Ser Tyr Pro Ile Ile Tyr
                245                 250                 255

Glu Pro Ile Phe Met Ala His Phe Asn Glu Ile Ile Val Pro Pro Gln
            260                 265                 270

Gly Trp Glu Ser Leu Met Tyr Met Val Ala Ala Ile Gly Ser Phe Met
        275                 280                 285
```

```
Ser Gly Val Ser Pro Glu Gln Asn Asp Asp Leu Thr Leu Phe Glu Leu
        290                 295                 300
Ala Lys Ser Lys Leu Ser Met Glu Ile Met Glu Arg Gly Asn Leu Thr
305                 310                 315                 320
Leu Val Thr Thr Ile Thr Leu Met Ser Asn Tyr Leu Gln Lys Arg Asp
                    325                 330                 335
Lys Pro Asn Ser Gly Tyr Ser Tyr Leu Gly Leu Ala Val Arg Met Ala
                340                 345                 350
Leu Gly Leu Gly Ile His Arg Glu Ile Asp Arg His Gly Glu Ser Leu
            355                 360                 365
Leu Glu Lys Glu Met Arg Arg Arg Ile Trp Trp Cys Leu Tyr Ile Phe
370                 375                 380
Asp Cys Gly Gln Asn Ile Thr Phe Gly Arg Pro Leu Cys Ile Pro Cys
385                 390                 395                 400
Ala Gly Ile Asp Thr Ser Leu Pro Met Asn Ile Pro Asp Ser Cys Leu
                405                 410                 415
Thr Ala Leu Thr Lys Gln Met Pro Val Pro Glu Asn Glu Pro Thr Ile
            420                 425                 430
Tyr Thr Ser Val Arg Leu Gln Ser Leu Leu His Leu Leu Thr Asn Gly
        435                 440                 445
Ile Tyr Glu Arg Ile Ile Thr Asp Pro Phe Pro Ser Ala Ser Gln Leu
    450                 455                 460
Leu Ala Arg Asp Lys Lys Tyr Leu Glu Arg Trp Lys Lys Leu Val Pro
465                 470                 475                 480
Pro Tyr Tyr Asp Glu Ser Ala Ser Val Gly Asp Lys Phe Lys Leu Ser
                485                 490                 495
Lys Cys Glu Leu Glu Trp Arg Phe Arg Asn Leu Arg Ile Leu Met Tyr
            500                 505                 510
Arg Thr Phe Leu Leu Lys Arg Val Val Ile Ser Ser Gln Asp Ser Ser
        515                 520                 525
Asp Gln Tyr Glu Arg Gln Ala Gly Glu Ile Cys Leu Gln Glu Cys Ser
    530                 535                 540
Lys Val Ile Lys Ser Met Asn His Phe Trp Cys Ser Lys Pro Asp His
545                 550                 555                 560
Asn Arg Met Glu Thr Trp Tyr Thr Leu Cys Phe Val Val Pro Ala Ala
                565                 570                 575
Leu Met Pro Leu Val Cys Leu Arg Asn Asn Pro Ser Ser Ala Asn Ala
            580                 585                 590
Asp Ser Trp Arg Asn Asp Val Ile Thr Ala Gln Asn Ile Ile Ala Ser
        595                 600                 605
Leu Thr Ser Ile Cys Pro Ser Ala Ala Lys Leu Leu Asp Leu Ile Ser
    610                 615                 620
Thr Leu Gly His Gly Tyr Leu Tyr Thr Gln Pro Asn Ala Thr Ser Pro
625                 630                 635                 640
Glu Pro Thr Ala Thr Asp Glu Ser Pro Thr Ser Gln Leu Leu Gln Leu
                645                 650                 655
His Ser Met Leu Trp Pro Val Ser Phe Asp Leu Glu Gln Gln Phe Asn
            660                 665                 670

Leu Thr

<210> SEQ ID NO 26
<211> LENGTH: 865
<212> TYPE: PRT
<213> ORGANISM: Kluyveromyces lactis
```

<400> SEQUENCE: 26

Met Gly Ser Arg Ala Ser Asn Ser Pro Ser Phe Ser Lys Ala Glu
1               5                   10                  15

Thr Leu Leu Pro Ser Glu Tyr Lys Lys Asn Ala Val Lys Lys Glu Thr
            20                  25                  30

Ile Arg Asn Gly Lys Lys Arg Lys Leu Pro Asp Thr Glu Ser Ser Asp
            35                  40                  45

Pro Glu Phe Ala Ser Arg Arg Leu Ile Ala Asn Thr Gly Thr Asp
50                  55                  60

Ala Val Ser Asn Gly Asn Lys Asn Asp Ser Asn Ala Asn Asn Asn
65                  70                  75                  80

Asn Asn Asn Asn Lys Lys Ser Ser Glu Val Met His Gln Ala Cys Asp
                85                  90                  95

Ala Cys Arg Lys Lys Lys Trp Lys Cys Ser Lys Thr Val Pro Thr Cys
            100                 105                 110

Thr Asn Cys Leu Lys Tyr Asn Leu Asp Cys Val Tyr Ser Pro Gln Val
            115                 120                 125

Val Arg Thr Pro Leu Thr Arg Ala His Leu Thr Glu Met Glu Asn Arg
130                 135                 140

Val Ala Glu Leu Glu Gln Phe Leu Lys Glu Leu Phe Pro Val Trp Asp
145                 150                 155                 160

Ile Asp Arg Leu Leu Gln Gln Lys Asp Thr Tyr Arg Ile Arg Glu Leu
            165                 170                 175

Leu Thr Met Gly Ser Thr Asn Thr Val Pro Gly Leu Ala Ser Asn Asn
            180                 185                 190

Ile Asp Ser Ser Leu Glu Gln Pro Val Ala Phe Gly Thr Ala Gln Pro
            195                 200                 205

Ala Gln Ser Leu Ser Thr Asp Pro Ala Val Gln Ser Gln Ala Tyr Pro
210                 215                 220

Met Gln Pro Val Pro Met Thr Glu Leu Gln Ser Ile Thr Asn Leu Arg
225                 230                 235                 240

His Thr Pro Ser Leu Leu Asp Glu Gln Gln Met Asn Thr Ile Ser Thr
            245                 250                 255

Ala Thr Leu Arg Asn Met Tyr Ser Ser Gly Asn Asn Asn Asn Asn Leu
            260                 265                 270

Gly Asn Ile Ser Gly Leu Ser Pro Val Thr Glu Ala Phe Phe Arg Trp
            275                 280                 285

Gln Glu Gly Glu Thr Ser Ile Asp Asn Ser Tyr Phe Gly Lys Gly Ser
            290                 295                 300

Ile Leu Phe Trp Leu Asn Gln Leu Leu Ser Ser Glu Lys Ile Ala Gly
305                 310                 315                 320

Val Thr Ser Lys Val Gly Asn Asp Ile Asn Thr Asn Asn Asn Ile
            325                 330                 335

Asn His Gln Lys Leu Pro Leu Ile Leu Asn Asn Ile Thr His Asn
            340                 345                 350

Val Ser Asp Ile Thr Thr Thr Ser Thr Ser Asn Lys Arg Ala Met
            355                 360                 365

Ser Pro Leu Ser Ala Asn Asp Ser Val Tyr Leu Ala Lys Arg Glu Thr
            370                 375                 380

Ile Ser Ala Tyr Ile Asp Ala Tyr Phe Lys His Tyr His Ala Leu Tyr
385                 390                 395                 400

Pro Leu Val Ser Lys Glu Met Phe Phe Ala Gln Tyr Asn Asp Gln Ile

```
                405                 410                 415
Lys Pro Glu Asn Val Glu Ile Trp His Ile Leu Leu Asn Ala Val Leu
            420                 425                 430

Ala Leu Gly Ser Trp Cys Ser Asn Ser Cys Ser Ser His His Thr Leu
            435                 440                 445

Tyr Tyr Gln Asn Ala Leu Ser Tyr Leu Ser Thr Ala Val Leu Glu Thr
            450                 455                 460

Gly Ser Thr Asp Leu Thr Ile Ala Leu Ile Leu Leu Thr His Tyr Val
465                 470                 475                 480

Gln Lys Met His Lys Pro Asn Thr Ala Trp Ser Leu Ile Gly Leu Cys
            485                 490                 495

Ser His Met Ala Thr Ser Leu Gly Leu His Arg Asp Leu Pro Asn Ser
            500                 505                 510

Thr Ile His Asp Gln Gln Leu Arg Arg Val Leu Trp Trp Thr Ile Tyr
            515                 520                 525

Cys Thr Gly Cys Asp Leu Ser Leu Glu Thr Gly Arg Pro Ser Leu Leu
            530                 535                 540

Pro Asn Leu Gln Ala Ile Asp Ile Pro Leu Pro Ala Ser Ser Ala Thr
545                 550                 555                 560

Ile Lys Glu Pro Ser Ile Tyr Ser Ser Ile Gln Glu Ser Gln Trp
            565                 570                 575

Ser Gln Ile Leu Gln Gln Lys Leu Ser Asn Asn Ser Tyr Gln Gln Ser
            580                 585                 590

Ala Gly Glu Cys Leu Ser Trp Phe Asp Ser Val Gln Ala Phe Leu Asp
            595                 600                 605

His Trp Pro Thr Pro Ser Thr Glu Ala Glu Leu Lys Ala Leu Asn Glu
            610                 615                 620

Thr Gln Leu Asp Trp Leu Pro Leu Val Lys Phe Arg Pro Tyr Trp Met
625                 630                 635                 640

Phe His Cys Ser Leu Ile Ser Leu Phe Ser Val Phe Phe Glu Glu Asp
            645                 650                 655

Ala Pro Thr Asp Asn Asn Val Ile Arg Cys Lys Glu Leu Cys Leu Gln
            660                 665                 670

Leu Ser Ser Arg Asn Ile Phe Ser Val Ala Thr Phe Val Arg Ser Tyr
            675                 680                 685

Ala Phe Asn Ser Leu Ser Cys Trp Tyr Ala Thr His Tyr Leu Val Arg
            690                 695                 700

Ser Ala Leu Val Pro Leu His Phe Ala Ser Arg Ile Ser Pro Gln His
705                 710                 715                 720

Ala Leu Trp Glu Thr Val Lys Ala Gln Leu Leu Ser Ala His Glu Ala
            725                 730                 735

Met Gly Ile Leu Ser Gln Glu Ser Leu Ala Ala Lys Phe Asp Gly
            740                 745                 750

Ile Leu Thr Lys Asn Tyr Ser Glu Ile Leu Gln Arg Glu Gly Ile Asn
            755                 760                 765

Lys Ser Gln Leu Met Pro Pro Thr Pro Leu Leu Gln Ser Thr Ser
770                 775                 780

Phe Ser Asp Leu Leu Ser Leu Trp Ser Ala Asn Ala Glu Asp Ala Pro
785                 790                 795                 800

Arg Val Ser Asn Ser Gln Met Pro Gln Ser Ile Thr Ile Thr Asp Ser
            805                 810                 815

Leu Leu Gln Ser Ser Thr Thr Gln Met Arg Pro Pro Thr Ser Gly
            820                 825                 830
```

```
Trp Pro Asp Thr Asn Asn Phe Leu Asn Pro Ser Thr Gln Gln Leu Phe
        835                 840                 845

Asn Thr Thr Thr Met Asp Asp Val Tyr Asn Tyr Ile Phe Asp Asn Asp
850                 855                 860

Glu
865

<210> SEQ ID NO 27
<211> LENGTH: 638
<212> TYPE: PRT
<213> ORGANISM: Aspergillus niger

<400> SEQUENCE: 27

Met Asn Ala Gly Ser Gly Ser Pro Ser Pro Lys Val Thr Arg Ser Pro
1               5                   10                  15

Leu Thr Arg Gln His Leu Thr Tyr Val Glu Arg Leu Gln Ala Phe
            20                  25                  30

Glu Thr Ala Leu Ser Arg Leu Phe Pro Gly Gly Asp Leu Asp Ala Thr
                35                  40                  45

Val Arg Ser Leu Leu His Asp Gln Glu Gly Pro Pro Lys Pro Gly Ser
50                  55                  60

Ser Lys Ser Ser Ser Arg His Ser Thr Pro Ala Lys Ala Glu Pro Asp
65                  70                  75                  80

Arg Ala Glu Pro Ala Pro Glu Ala Leu Pro Gln Gln Ala Asp Gly Phe
                85                  90                  95

Asp Trp Ala Glu Asn Lys Ile Thr Val Gly Asp Leu Thr Asp Gly Met
            100                 105                 110

Ala Ala Leu Ser Ile Lys Pro Glu Gly Ala Gly Tyr Phe Gly Ala Ser
        115                 120                 125

Ser Ser Val Val Pro Leu Arg Ala Leu Leu Lys His Gly Phe Asp Leu
130                 135                 140

Asn Ile Pro Ala Arg Ser Ser Lys Ser Ser Tyr Ser Met Glu Arg Val
145                 150                 155                 160

Pro Leu Lys Ala Gln Leu Leu Ser Thr Ala Pro Ser Gly Leu Val Glu
                165                 170                 175

Gln Ala Phe Met Asp Ala Phe Phe Leu Asn Tyr His Thr Ser Tyr Pro
            180                 185                 190

Phe Val His Glu Gly Thr Phe Arg Ala Gln Phe Tyr Glu Gln Val Pro
        195                 200                 205

Arg Pro His Gly Gln Ala Trp Gln Ile Leu Leu Asn Thr Ile Leu Ala
210                 215                 220

Leu Gly Ala Trp Ser Ile Gly Asp Asp Asn Ser Asp Leu Asp Ile Thr
225                 230                 235                 240

Phe Tyr Gln Glu Ala Arg Gly His Leu Gln Gln Val Ser Val Phe Glu
                245                 250                 255

Thr Gly Asn Leu Thr Leu Val Gln Ala Leu Leu Leu Ser Asn Tyr
            260                 265                 270

Ala Gln Lys Arg Asn Lys Pro Asn Thr Gly Trp Asn Phe Leu Gly Leu
        275                 280                 285

Ala Val Arg Met Ala Met Ser Leu Gly Leu His Lys Glu Phe Pro Gly
290                 295                 300

Trp Lys Ile Ser Leu Leu Gln Arg Glu Val Arg Arg Leu Trp Trp
305                 310                 315                 320

Gly Val Tyr Ile Phe Asp Ser Gly Ala Ala Lys Thr Phe Gly Arg Pro
```

```
               325                 330                 335
Ile Leu Leu Pro Glu Asp Asp Val Met Asp Ala Lys His Val Leu Asn
            340                 345                 350

Ile His Asp Glu Ala Leu Thr Pro Leu Thr Thr Leu Pro Pro Glu
            355                 360                 365

Val Asn Glu Pro Thr Leu Tyr Ser Gly Leu Ile Ala Gln Ala Arg Phe
            370                 375                 380

His Leu Leu Thr Asn Ser Val Tyr Gln Arg Leu Ile Ser Gly Pro Ser
385                 390                 395                 400

Leu Thr Pro Glu Glu Thr Leu Gly Leu Gln Arg Pro Met Glu Glu Trp
                405                 410                 415

Tyr Asn Gly Leu Pro Asp Tyr Phe Lys Gln Pro Pro Thr Pro Ile Ser
                420                 425                 430

Asp Ala Phe Ala Leu Val Arg Asn Arg Leu Met Trp Arg Asp Trp Asn
                435                 440                 445

Leu Arg Ile Leu Leu Tyr Arg Pro Ile Leu Leu Arg Trp Ala Ser Arg
            450                 455                 460

Arg Trp Thr Pro Asn Ser Ala Pro Glu Pro Glu Asp Pro Leu Glu Ala
465                 470                 475                 480

Asp Cys Arg Arg Leu Cys Leu Arg Asn Ala Arg Leu Thr Ile Ser Ser
                485                 490                 495

Ile Ala Asp Phe Val Asn Asn His Val Cys Thr Arg Ile Gly Ala Trp
                500                 505                 510

Tyr Met Leu Tyr Phe Leu Phe Gln Ala Gly Val Ile Pro Ile Ile Leu
            515                 520                 525

Leu Met Thr Asp Pro Thr Ser Thr Asp Ala Pro Ser Trp Leu Gln Glu
            530                 535                 540

Ile Glu Ser Thr Lys Lys Leu Leu Val His Pro Ser Leu Ser Asn Asn
545                 550                 555                 560

Arg Leu Ala Thr Arg Cys Leu Glu Val Val Asn Arg Leu Cys Ser Pro
                565                 570                 575

Ala Tyr Thr Ser Ala Ala Ala Asp Lys Thr Ala Gly Gln Thr Ala Pro
                580                 585                 590

Ile Leu Met Pro Phe Ser Asp Gln Leu Phe Asn Asp Pro Thr Phe Gly
            595                 600                 605

Ser Met Phe Pro Asp Val Asp Gln Glu Leu Asn Leu Ala Gly Met Asp
            610                 615                 620

Phe Ser Glu Trp Val Asn Phe Pro Pro Gln Asn Glu Phe Val
625                 630                 635

<210> SEQ ID NO 28
<211> LENGTH: 687
<212> TYPE: PRT
<213> ORGANISM: Aspergillus nidulans

<400> SEQUENCE: 28

Met Met Ser Lys Asn Lys Ile Thr Met Gly Ser Thr Arg Asp Ser His
1               5                   10                  15

Ser Tyr Ala Cys Asp Glu Cys Arg Leu Arg Lys Ser Arg Cys Ser Lys
                20                  25                  30

Glu Lys Pro Thr Cys Ala Gln Cys Lys Gln Leu Asp Lys Glu Cys Lys
            35                  40                  45

Tyr Ser Pro Lys Ile Thr Arg Ser Pro Leu Thr Arg Gln His Leu Thr
        50                  55                  60
```

```
Tyr Val Glu Asp Arg Leu Gln Ala Phe Glu Ser Ala Leu Gly Arg Leu
 65                  70                  75                  80

Phe Pro Gly Gly Asp Leu Asp Ala Thr Val Arg Ser Leu Leu Gln Asp
                 85                  90                  95

Gln Asp Pro Leu Ser Lys Glu Arg Ser Ser Lys Ser Ser Ser Arg
            100                 105                 110

His Ser Thr Pro Ala Lys Thr Glu Ala Asp Arg His Glu Ser Ala Pro
            115                 120                 125

Glu Ala Leu Pro Gln Gln Ala Asp Gly Phe Asp Trp Ala Glu Asn Arg
        130                 135                 140

Ile Thr Leu Gly Asp Leu Thr Asp Gly Met Ala Ala Leu Ser Ile Lys
145                 150                 155                 160

Pro Glu Gly Ala Gly Tyr Phe Gly Ala Ser Ser Val Val Pro Leu
                165                 170                 175

Arg Ala Leu Leu Lys His Gly Phe Asp Leu Asn Ile Pro Ser Gly Ser
                180                 185                 190

Ser Lys Arg Val Asp Asn Ser Asp Arg Val Pro Leu Lys Ser Gln Leu
        195                 200                 205

Leu Asn Ile Ala Pro Ser Gly Val Ile Glu Gln Ala Phe Met Asp Ala
210                 215                 220

Phe Phe Asn Asn Tyr His Met Ser Tyr Pro Phe Val His Glu Ala Thr
225                 230                 235                 240

Phe Arg Ala Gln Phe His Glu Gln Leu Pro Arg Pro His Gly Pro Ala
                245                 250                 255

Trp Gln Ile Leu Leu Asn Thr Ile Leu Ala Leu Gly Ala Trp Cys Ile
            260                 265                 270

Gly Asp Asp Asn Ser Asp Leu Asp Ile Thr Phe Tyr Gln Glu Ala Arg
        275                 280                 285

Ser Arg Leu Gln Gln Met Ser Val Phe Glu Ala Gly Asn Leu Thr Leu
    290                 295                 300

Val Gln Ala Leu Leu Phe Leu Ser Asn Tyr Ala Gln Lys Arg Asn Lys
305                 310                 315                 320

Pro Asn Thr Gly Trp Asn Phe Leu Gly Leu Ala Val Arg Met Ser Met
                325                 330                 335

Ser Leu Gly Leu His Lys Glu Phe His Gly Lys Ile Ser Leu Leu
            340                 345                 350

Gln Arg Glu Val Arg Arg Leu Trp Trp Gly Val Tyr Ile Phe Asp
    355                 360                 365

Ser Gly Ala Ala Lys Thr Phe Gly Arg Pro Ile Leu Leu Pro Glu Asp
    370                 375                 380

Ser Val Met Asp Val Lys His Val Leu Asn Ile His Asp Glu Ala Leu
385                 390                 395                 400

Thr Ser Thr Thr Thr Val Val Pro Pro Glu Val Asn Glu Pro Thr Leu
                405                 410                 415

Tyr Thr Gly Met Leu Ala Gln Ala Lys Phe His Ile Leu Thr Asn Ser
                420                 425                 430

Val Tyr Gln Arg Leu Ile Ser Gly Pro Asn Pro Thr Pro Glu Glu Thr
        435                 440                 445

Leu Ser Leu Gln Lys Pro Met Glu Glu Trp Tyr Asn Ser Leu Pro Asp
        450                 455                 460

Tyr Ile Lys Asn Pro Ala Pro Gly Ser Met Ser Asp Asn Phe Ala Leu
465                 470                 475                 480

Val Arg Ser Arg Leu Leu Trp Arg Asp Trp Asn Leu Arg Ile Leu Ile
```

```
                485                 490                 495
Tyr Arg Pro Ile Leu Arg Trp Ala Ser Lys Arg Trp Thr Pro Asn
            500                 505                 510

Thr Pro Thr Glu Pro Glu Asp Pro Tyr Glu Ala Glu Cys Arg Met Leu
        515                 520                 525

Cys Phe Arg Asn Ala Lys Leu Thr Ile Ser Ser Ile Thr Asp Phe Val
        530                 535                 540

Asn Asn Tyr Pro Cys Thr Arg Val Gly Ala Trp Tyr Met Leu Tyr Phe
545                 550                 555                 560

Leu Phe Gln Ala Gly Leu Ile Pro Ile Ile Leu Met Thr Asp Pro
                565                 570                 575

Thr Ser Ala Glu Ala Pro Ser Trp Ile Gln Glu Ile Glu Ala Thr Lys
            580                 585                 590

Ala Leu Leu Met Tyr Pro Ser Leu Ser Asn Asn Asn Leu Ala Gly Arg
            595                 600                 605

Cys Leu Asp Val Ile Tyr Arg Leu Cys Ala Pro Val Tyr Pro Ser Asn
            610                 615                 620

Ala Thr Ser Ser Ala Ser Ala Pro Ser Gln Gln Pro Gln Pro Ile Tyr
625                 630                 635                 640

Met Pro Phe Ala Asp Gln Leu Tyr Asn Asp Pro Thr Phe Gly Ser Leu
                645                 650                 655

Phe Pro Asp Val Asn Gln Asp Leu Asn Val Ser Ala Gly Met Asp Phe
                660                 665                 670

Ser Glu Trp Val Asn Phe Ala Pro Thr Pro His Asn Asp Phe Thr
                675                 680                 685

<210> SEQ ID NO 29
<211> LENGTH: 700
<212> TYPE: PRT
<213> ORGANISM: Aspergillus flavus

<400> SEQUENCE: 29

Met Arg Val Glu Asn Ala Asp Asp Cys Asp Arg Leu Leu Pro Ser Cys
1               5                   10                  15

Ser Leu Cys Asp Lys Phe Ser Arg Cys Ile Tyr Glu Thr Leu Ser
            20                  25                  30

Lys Thr Pro Leu Thr Arg Gln Tyr Leu Thr Glu Val Glu Glu Leu
        35                  40                  45

Thr Arg Thr Lys Ala Leu Leu Ser Glu Leu Leu Pro Gly Thr Ser Arg
    50                  55                  60

Asp Ile Ser Asn Gly Glu Arg Phe Ile Tyr Pro Gln Gly Thr Thr
65                  70                  75                  80

Gly Asp Arg Gly Leu Thr Ser Glu Ile Pro Asn Arg Glu Gly Ser Ser
                85                  90                  95

Glu Gln Pro Glu Arg Ala Tyr Val Pro His Ser Asn Ile Gly Ser Glu
            100                 105                 110

Thr Ile Pro Ala Pro Glu Val Pro Ser Arg Pro Ser Leu Gly Val Phe
        115                 120                 125

Ser Ala Ser Leu Ser Asn Ser Gly Gln Leu Tyr Asp Tyr Ser Asp Arg
    130                 135                 140

Asn Gln Thr Gly Ile Ser His Arg Ala Asn Arg Arg Ser Gln Asp Ala
145                 150                 155                 160

Val Met Ser Met Glu Thr Pro Pro Ser Ala Gly Asn Val Asn Phe Glu
                165                 170                 175
```

-continued

Trp Asp Glu Arg Thr Glu Asp Gln Gly Gly Asp Gly Phe Val Asp Gly
            180                 185                 190

Met Ala Ile Leu Pro Ser Arg Ser Asn Asp Gly Gly Tyr Leu Gly Thr
        195                 200                 205

Ala Ser Gly Ala Ala Leu Leu Arg Met Thr Asn Ser Gln Ser Gly Gly
    210                 215                 220

Glu Arg Leu Asp Met Pro Glu Pro Gly Arg Pro Phe Glu Thr Ala Ser
225                 230                 235                 240

Ser His Pro Ser Pro Ser Ile Pro Phe Ala Leu Ser Ser Leu Ser Gln
                245                 250                 255

Leu Glu Pro Phe Val Asp Ala Tyr Phe Ser Leu Tyr His Cys Ser Tyr
            260                 265                 270

Pro Ile Ile His Glu Ala Thr Phe Arg Ala Gln Phe Met Glu Val Ile
        275                 280                 285

Pro Arg Pro Thr Ser Asn Thr Trp Gln Val Leu Leu Tyr Val Val Ala
    290                 295                 300

Ala Leu Gly Ala Phe Thr Ala Val Thr Pro Thr Asp Val Asp Leu
305                 310                 315                 320

Ala Leu Phe Lys Ala Ala Lys Ala Arg Leu Thr Ile Asp Val Leu Glu
                325                 330                 335

Thr Gly Ser Leu Ile Leu Val Gln Ala Leu Thr Leu Ser Ser Asn Tyr
            340                 345                 350

Leu Gln Lys Arg Asn Lys Pro Asn Ser Gly Tyr Asn Tyr Leu Gly Leu
        355                 360                 365

Ala Arg Arg Thr Ala Met Gly Ile Gly Leu His Lys Glu Phe Pro Thr
    370                 375                 380

Ser Lys Ala Ser Pro Leu Ala Met Glu Met Arg Arg Arg Val Trp Tyr
385                 390                 395                 400

Cys Leu Tyr Ile Phe Asp Val Gly Ala Ile Ile Thr Phe Ser Arg Pro
                405                 410                 415

Leu Glu Phe Pro Glu Gln Gly Ile Glu Thr Arg Leu Pro Leu Asn Ile
            420                 425                 430

His Glu Ser Gly Ile Thr Ala Ser Thr Gln Thr Ala Pro Ser Pro Val
        435                 440                 445

Thr Glu Thr Thr Val Tyr Thr His Leu Arg Ala Gln Ala Met Phe His
    450                 455                 460

Leu Lys Thr Asn Leu Ile Tyr Thr Lys Ile Thr Ser Thr Ser Phe Pro
465                 470                 475                 480

Ser Ala Ala Glu Leu Ile Glu Leu Asp Asp Arg Leu Ile Gly Asp Trp
                485                 490                 495

Leu Ala Ser Leu Pro Tyr Phe Phe Asn Glu Gly Ala Ile Gln Ala Pro
            500                 505                 510

Lys Phe Ala Leu Cys His Ser Ile Leu Arg Trp Arg Tyr Arg Asn Leu
        515                 520                 525

Arg Ile Leu Met Tyr Arg Pro Phe Leu Val Gly Lys Trp Met Leu Asn
    530                 535                 540

Ser Asp Gln Gly Pro Asp Gly Leu Arg Glu Lys Asp Thr His Val
545                 550                 555                 560

Glu Leu Ala Ile Gln Arg Cys Phe Asp Ala Ala Arg Glu Ser Val Glu
                565                 570                 575

Leu Ile Ser Ser Phe Trp Ala Gln His Gln Lys Thr Thr Met Ala Cys
            580                 585                 590

Trp Tyr Gly Val Tyr Phe Leu Phe Gln Ala Ile Leu Ile Pro Val Ile

```
                     595                  600                  605
        Cys Leu Arg Asn Asn Pro Ser Asp Pro Ala Ala His Gly Trp Arg Glu
                    610                  615                  620

Gln Ile Phe Gln Ala Val Asn Thr Leu Glu Ser Met Val Pro Leu Asn
        625                  630                  635                  640

Ala Asn Ala Glu Arg Phe Leu Arg Val Ile Gln Ser Leu Cys Gly Cys
                        645                  650                  655

Tyr Leu Tyr Pro Arg Ser Asn Gly Trp Glu Gly Pro Ile Gln Glu Ser
                    660                  665                  670

Pro Glu Thr Gln Ile Ala Asn Leu Tyr Pro Leu Met Trp Pro Thr Leu
                        675                  680                  685

Glu Met Ala Gln Leu Asp Gly Val Asp Ser Ala Leu
        690                  695                  700

<210> SEQ ID NO 30
<211> LENGTH: 773
<212> TYPE: PRT
<213> ORGANISM: Debaryomyces hansenii

<400> SEQUENCE: 30

Met Lys Tyr Glu Arg Gly Ser Ser Val Gln Gln Ala Cys Asp Ser
        1               5                   10                  15

Cys Arg Leu Arg Lys Leu Lys Cys Ser Lys Gly Ser Pro Gln Cys His
                        20                  25                  30

Asn Cys Lys Glu His Ser Trp Lys Cys Val Tyr Ser Pro Lys Ala Val
                    35                  40                  45

Arg Thr Pro Leu Thr Arg Ala Tyr Leu Thr Arg Val Glu Lys Arg Val
        50                  55                  60

Lys Gly Leu Glu Ser Leu Leu Lys Arg Leu Leu Pro Glu Asp Val Glu
        65                  70                  75                  80

Ile Asn Glu Leu Leu Arg Thr Ile Glu Ile Asn Lys Ser His Ser Ile
                        85                  90                  95

Asp Gly Asp Ser Gly Gly Gly Val Asp Asp Val Ser Gln Gln Phe Tyr
                    100                 105                 110

Lys Gln Ile Asn Leu Thr Ser Asn Glu Leu Ser Glu Ile Pro Ile Thr
                        115                 120                 125

Leu Lys Asn Ile Asn Arg Ile Ser Gln Arg Lys Ala Lys Asp Ser Ala
        130                 135                 140

Thr Glu Lys Lys Arg Glu Phe Gln Pro Glu Asp Tyr Leu Ile Asn Ile
        145                 150                 155                 160

Glu Lys Ser Asp Leu Asn Ser Phe Asp Glu Arg Asp Phe Asn Ser
                        165                 170                 175

Asn Ser Gln Ile Leu Tyr Asp Ser Ile Asp Gly Met Ala Ala Leu
                    180                 185                 190

Ser Asn Asp Ile Gly Leu Asn Phe Asp Asn Ser Asn Gly Tyr Phe Gly
                    195                 200                 205

Ile Asn Ser Ser Asn Gly Leu Leu Lys Phe Leu Gln Ala Lys Ser Arg
                    210                 215                 220

Gln Asn Gly Asn Gly Ile Leu Lys Leu Asn Asn Tyr Asn Tyr Asp Phe
        225                 230                 235                 240

Asn Asn Glu Glu Asn Asp Asn Asp His Ile Leu Asp Asp Glu Ile Asn
                        245                 250                 255

Asn Ile Trp Lys Ser Ile Asn Ser Gly Lys Ile Glu Asp Leu Leu Asp
                    260                 265                 270
```

```
Asn Leu Asn Phe Gln Ser Ile Met Val Asn Ser Phe Phe Glu Asn Tyr
            275                 280                 285
Tyr Lys Val Tyr Pro Phe Ile Asn Lys Lys Phe Leu Ser Glu Tyr
        290                 295                 300
Ser Ala Phe Ile Glu Arg Gln Glu Ser Arg Tyr Asn Glu Tyr Asp Leu
305                 310                 315                 320
Asp Leu Asp Ile Asn Glu Asp Asn Lys Val Leu Ser Phe Gln Val
                325                 330                 335
Leu Leu Asn Thr Val Leu Ala Ile Gly Val Trp Cys Lys Val Gly Glu
            340                 345                 350
Asn Ser Lys Ile His Thr Phe Tyr Gln Arg Val Lys Gly Phe Ile
        355                 360                 365
Gln Leu Leu Asn Ile Phe Glu Tyr Ser Asp Thr Gln Leu Leu Glu Ser
    370                 375                 380
Phe Val Leu Leu Ser Asn Tyr Val Gln Lys Thr Asn Lys Pro Asn Thr
385                 390                 395                 400
Gly Trp Ser Tyr Leu Gly Leu Ser Thr Arg Ile Ala Thr Ser Leu Gly
                405                 410                 415
Leu His Lys Glu Val Arg Ile Asp Lys His Asp Phe Asn Ser Ala Asp
            420                 425                 430
Lys Leu Gly Leu Phe Glu Asp Ile Glu Ile Arg Lys Arg Leu Trp Trp
        435                 440                 445
Gly Met Tyr Phe Phe Asp Val Gly Thr Thr Leu Thr Phe Gly Arg Pro
    450                 455                 460
Leu Thr Ile Pro Pro Leu Gly Thr Ile Asp Leu Glu Pro Val Ser Asn
465                 470                 475                 480
Ile Asp Asp Asn Leu Leu His Gly Ser Lys Asn Ile Glu Glu Cys Ile
                485                 490                 495
Val Thr Tyr Pro Thr Ile Tyr Thr Thr Leu Ile Tyr Glu Ser Glu Leu
            500                 505                 510
Thr Lys Leu Ser Thr Arg Ile Tyr Asn Tyr Asn Ser Ser Val Leu Lys
        515                 520                 525
Leu Lys Asn Asp Lys Ser Lys Met Ile Gly Leu Leu Asp Met Asn Glu
    530                 535                 540
Leu Leu Glu Asn Phe Val Lys Asn Leu Pro Ser Cys Phe Asp Glu Asn
545                 550                 555                 560
Asp Glu Lys Ser Tyr Ala Tyr Val Leu Asn Ser Trp Ser Ser Asn His
                565                 570                 575
Tyr His Asn Asp Asn Gln Ser Ile Pro Lys Trp Phe Ala Val Ser Arg
            580                 585                 590
Leu Arg Leu Ile Cys Arg Tyr Lys Asn Leu Gln Met Leu Ile Phe Arg
        595                 600                 605
Tyr Ile Leu Trp Glu Ser Thr Asn Asp Asn Ser Phe Asp Leu Ser Tyr
    610                 615                 620
Leu Asn Leu Ile Lys Lys Cys Arg Lys Ala Cys Phe Lys Ser Ser Val
625                 630                 635                 640
Glu Thr Val Ile Leu Ile Asp Asn Phe Ile Lys Arg Asn Glu Leu Asp
                645                 650                 655
Tyr Leu Ser Ser Trp Tyr Ala Thr Tyr Phe Leu Phe Gln Ala Ile Leu
            660                 665                 670
Ile Pro Ile Leu Lys Leu Val Ile Asn Asp Lys Ser Glu Gly Ser Val
        675                 680                 685
Asp Asp Glu Tyr Tyr Ser Asn Asp Glu Glu Leu Phe Asn Tyr Ile Glu
```

```
                690                 695                 700

Leu Ser Arg Leu Ser Phe Asp Lys Leu Lys Asn Phe Asn Lys Leu Ala
705                 710                 715                 720

Gly Lys Phe Ser Lys Leu Ile Asp Thr Leu Ile Tyr Asp Lys Lys Asn
                725                 730                 735

Ala Val Asp Phe Met Ser Gln Trp Asn Asp Asn Ile Ser Asn Leu
                740                 745                 750

Asp Ser Val Asn Asn Leu Asp Asp Leu Phe Gln Phe Thr Lys Ile
                755                 760                 765

Phe Asn Leu Asn Ser
        770

<210> SEQ ID NO 31
<211> LENGTH: 794
<212> TYPE: PRT
<213> ORGANISM: Zygosaccharomyces rouxii

<400> SEQUENCE: 31

Met Lys Arg Leu Asn Thr Ile Asp His Ala Cys Asp Ser Cys Arg Gln
1               5                   10                  15

Lys Lys Leu Arg Cys Ser Lys Glu Glu Pro Lys Cys Ala Lys Cys Ile
                20                  25                  30

Gln Asn Gly Trp Glu Cys Cys Tyr Ser Pro Lys Ala Asn Arg Thr Pro
            35                  40                  45

Leu Thr Arg Ala His Met Thr Lys Val Glu Thr Lys Leu Asp Arg Leu
50                  55                  60

Glu Gln Leu Phe Arg Glu Leu Phe Pro Glu Glu Asp Leu Asp Lys Val
65                  70                  75                  80

Leu Asn Asp Arg Asn Thr Gly Gln Leu Lys Glu Arg Leu Lys Arg Phe
                85                  90                  95

Leu Val Arg Arg Ala Lys Gly Val Gly Asn Asp Arg Met Asp Asp His
                100                 105                 110

Glu Ser Val Gly Ile Gly Leu Gly Thr His Ser Asp Ser Asn Gln Glu
            115                 120                 125

His Ile Thr Glu Gly Glu Val Pro Lys Asp Pro Leu Arg Gly Phe Asp
    130                 135                 140

Trp Val Glu Gly Gln Asp Met Pro Ile Gly Ser Asp Arg Val Gly Phe
145                 150                 155                 160

Ile Val Thr Asp Ile Ser Asn Ser Gly Tyr Tyr Gly Gln Glu Cys Pro
                165                 170                 175

Arg Leu Ile Phe Lys Lys Leu Gly Ile Asp Ser Val Pro Leu Leu Thr
                180                 185                 190

Thr Lys Ala Ser Ser Ile Asn Ala Val Thr Asp Pro His Ala Leu Cys
            195                 200                 205

Ser Arg Asn Val Thr Ser Lys Tyr Val Lys Ala Tyr Phe Asp Asn Phe
    210                 215                 220

His Ile Tyr Tyr Pro Leu Ile Asp Thr His Ile Phe Leu Lys Leu Tyr
225                 230                 235                 240

Asp Asn Gln Ala Gly Leu Arg Tyr Val Asp Gln Trp Gln Ile Leu Phe
                245                 250                 255

Asn Thr Val Leu Ala Ile Gly Ala Trp Ser Ser Glu Gly Glu Ser Thr
                260                 265                 270

Asp Ala Asp Leu Phe Tyr Tyr Ser Asn Val Lys Ser His Leu Lys Pro
            275                 280                 285
```

```
Lys Val Phe Glu Ala Gly Ser Val Thr Leu Val Ile Ala Phe His Leu
    290                 295                 300

Leu Ser Arg Tyr Ala Glu Trp Arg Gln Asn Pro Asn Thr Gly Tyr Leu
305                 310                 315                 320

Tyr His Gly His Ala Leu Arg Met Ala Ile Ser Leu Gly Leu His Arg
                325                 330                 335

Asp Leu Pro Pro Glu Gly Ile Pro Asp Val Ile Lys Glu Arg Arg Arg
            340                 345                 350

Arg Ile Trp Thr Cys Leu Tyr Ser His Glu Val His Ser Ala Leu Leu
        355                 360                 365

Asp Gly Arg Pro Leu Gln Tyr Met Phe Phe Asp Gln Val Thr Ile
370                 375                 380

Ser Leu Pro Asn Ser Val Glu Asp Glu Asn Thr Trp Thr Lys Gly Pro
385                 390                 395                 400

Ser Ile Tyr Met Gly Ala Ile Glu Thr Ala Lys Leu Leu Lys Glu Phe
                405                 410                 415

Gly Tyr Val Trp Phe Val Asp Ser Lys Ile Thr Thr Ser Arg Cys Leu
            420                 425                 430

Gln Leu Cys Gln Arg Leu Asp Ala Cys Gln Lys Ala Met Pro Lys Tyr
        435                 440                 445

Leu Gln Ala Asp Glu His Leu Thr Gly Leu Thr Tyr Tyr Leu Lys Lys
450                 455                 460

Tyr Pro Trp Ile Ser Phe Ile Arg Phe Tyr Leu Arg Trp Glu Arg Gln
465                 470                 475                 480

Trp Leu Gln Ile Tyr Val Leu Arg Arg Leu Leu Gln Ser Glu Gly Ala
                485                 490                 495

Leu Lys Val Glu Pro Asn Ser Glu Leu Asp Lys Cys Ala Thr Met Leu
            500                 505                 510

Ser Asp Ile Ala Gln Lys Thr Ile Trp Gly Val Ala Asn Tyr Leu Asn
        515                 520                 525

Asn His His Leu Thr Ser Phe Phe Ala Trp Tyr Cys Thr Phe Tyr Leu
530                 535                 540

Phe Asn Ala Ser Leu Val Pro Leu Ala Gln Ile Tyr Thr Gly Thr Gly
545                 550                 555                 560

Asp Arg Gln Glu Ser Leu Asn Gln Leu Ser Thr Cys Ile Arg Leu Phe
                565                 570                 575

Lys Gln Leu Lys Asp Tyr Asn Leu Ser Thr Cys Glu Lys Tyr Ile His
            580                 585                 590

Ile Leu Asp His Leu Cys Asp Gly Gly Met Asn Thr Thr Asp Ser Ala
        595                 600                 605

Thr Arg Gly Thr Asn Val Glu Val Lys Lys Gln Gln Thr Thr His Ser
610                 615                 620

Pro Pro Leu Pro Thr Met Ser Asn Ala Leu Ser Pro Ser Val Lys Ser
625                 630                 635                 640

Ala Ala Ser Leu Ser Asp Leu Glu Lys Leu Phe Ser Ser Arg Thr Pro
                645                 650                 655

Val Leu Asn Leu Arg Val Pro Ser Gln Pro Ala Gln Tyr Pro Thr Gln
            660                 665                 670

Pro Val Gln Leu Pro Gln Val Ser Pro Ile Ile Pro Ser Thr Thr Ala
        675                 680                 685

Ala Ser Asn Ala Ser Asn Met Pro Gln Pro Pro Ser Gln Leu Ile Arg
690                 695                 700

Gln Thr Thr Pro Ala Ala Ser Leu Pro Gly Asn Glu Cys Ser Pro Ser
```

```
                705                 710                 715                 720
Gly Ser Thr Thr Thr Thr Ala Pro Asn Ser Ala Ile Lys Thr Gly
                    725                 730                 735

His Pro Leu Asp Asn Glu Gly Pro Phe Trp Thr Asp Gln Ala Ala Tyr
                740                 745                 750

Asn Ala Phe Gly Leu Thr Ser Ser Leu Phe Asn Thr Thr Thr Met Asp
            755                 760                 765

Asp Val Tyr Asn Phe Leu Phe Asp Glu Glu Asp His Thr Pro Pro Lys
        770                 775                 780

Ser Lys Ser Trp Gln Asp Ser Asp Arg His
785                 790

<210> SEQ ID NO 32
<211> LENGTH: 881
<212> TYPE: PRT
<213> ORGANISM: Saccharomyces cerevisiae

<400> SEQUENCE: 32

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser Ile Asp Ser Ala Ala His His Asp Asn Ser Thr Ile Pro
145                 150                 155                 160

Leu Asp Phe Met Pro Arg Asp Ala Leu His Gly Phe Asp Trp Ser Glu
                165                 170                 175

Glu Asp Asp Met Ser Asp Gly Leu Pro Phe Leu Lys Thr Asp Pro Asn
            180                 185                 190

Asn Asn Gly Phe Phe Gly Asp Gly Ser Leu Leu Cys Ile Leu Arg Ser
        195                 200                 205

Ile Gly Phe Lys Pro Glu Asn Tyr Thr Asn Ser Asn Val Asn Arg Leu
    210                 215                 220

Pro Thr Met Ile Thr Asp Arg Tyr Thr Leu Ala Ser Arg Ser Thr Thr
225                 230                 235                 240

Ser Arg Leu Leu Gln Ser Tyr Leu Asn Asn Phe His Pro Tyr Cys Pro
                245                 250                 255

Ile Val His Ser Pro Thr Leu Met Met Leu Tyr Asn Asn Gln Ile Glu
            260                 265                 270

Ile Ala Ser Lys Asp Gln Trp Gln Ile Leu Phe Asn Cys Ile Leu Ala
        275                 280                 285
```

```
Ile Gly Ala Trp Cys Ile Glu Gly Glu Ser Thr Asp Ile Asp Val Phe
290                 295                 300

Tyr Tyr Gln Asn Ala Lys Ser His Leu Thr Ser Lys Val Phe Glu Ser
305                 310                 315                 320

Gly Ser Ile Ile Leu Val Thr Ala Leu His Leu Leu Ser Arg Tyr Thr
            325                 330                 335

Gln Trp Arg Gln Lys Thr Asn Thr Ser Tyr Asn Phe His Ser Phe Ser
            340                 345                 350

Ile Arg Met Ala Ile Ser Leu Gly Leu Asn Arg Asp Leu Pro Ser Ser
            355                 360                 365

Phe Ser Asp Ser Ser Ile Leu Glu Gln Arg Arg Ile Trp Trp Ser
370                 375                 380

Val Tyr Ser Trp Glu Ile Gln Leu Ser Leu Leu Tyr Gly Arg Ser Ile
385                 390                 395                 400

Gln Leu Ser Gln Asn Thr Ile Ser Phe Pro Ser Ser Val Asp Asp Val
                405                 410                 415

Gln Arg Thr Thr Thr Gly Pro Thr Ile Tyr His Gly Ile Ile Glu Thr
            420                 425                 430

Ala Arg Leu Leu Gln Val Phe Thr Lys Ile Tyr Glu Leu Asp Lys Thr
            435                 440                 445

Val Thr Ala Glu Lys Ser Pro Ile Cys Ala Lys Lys Cys Leu Met Ile
450                 455                 460

Cys Asn Glu Ile Glu Glu Val Ser Arg Gln Ala Pro Lys Phe Leu Gln
465                 470                 475                 480

Met Asp Ile Ser Thr Thr Ala Leu Thr Asn Leu Leu Lys Glu His Pro
            485                 490                 495

Trp Leu Ser Phe Thr Arg Phe Glu Leu Lys Trp Lys Gln Leu Ser Leu
            500                 505                 510

Ile Ile Tyr Val Leu Arg Asp Phe Phe Thr Asn Phe Thr Gln Lys Lys
            515                 520                 525

Ser Gln Leu Glu Gln Asp Gln Asn Asp His Gln Ser Tyr Glu Val Lys
530                 535                 540

Arg Cys Ser Ile Met Leu Ser Asp Ala Ala Gln Arg Thr Val Met Ser
545                 550                 555                 560

Val Ser Ser Tyr Met Asp Asn His Asn Val Thr Pro Tyr Phe Ala Trp
            565                 570                 575

Asn Cys Ser Tyr Tyr Leu Phe Asn Ala Val Leu Val Pro Ile Lys Thr
            580                 585                 590

Leu Leu Ser Asn Ser Lys Ser Asn Ala Glu Asn Glu Thr Ala Gln
            595                 600                 605

Leu Leu Gln Gln Ile Asn Thr Val Leu Met Leu Leu Lys Lys Leu Ala
610                 615                 620

Thr Phe Lys Ile Gln Thr Cys Glu Lys Tyr Ile Gln Val Leu Glu Glu
625                 630                 635                 640

Val Cys Ala Pro Phe Leu Leu Ser Gln Cys Ala Ile Pro Leu Pro His
            645                 650                 655

Ile Ser Tyr Asn Asn Ser Asn Gly Ser Ala Ile Lys Asn Ile Val Gly
            660                 665                 670

Ser Ala Thr Ile Ala Gln Tyr Pro Thr Leu Pro Glu Gly Asn Val Asn
            675                 680                 685

Asn Ile Ser Val Lys Tyr Val Ser Pro Gly Ser Val Gly Pro Ser Pro
690                 695                 700

Val Pro Leu Lys Ser Gly Ala Ser Phe Ser Asp Leu Val Lys Leu Leu
```

```
              705                 710                 715                 720
Ser Asn Arg Pro Pro Ser Arg Asn Ser Pro Val Thr Ile Pro Arg Ser
                    725                 730                 735

Thr Pro Ser His Arg Ser Val Thr Pro Phe Leu Gly Gln Gln Gln Gln
                740                 745                 750

Leu Gln Ser Leu Val Pro Leu Thr Pro Ser Ala Leu Phe Gly Gly Ala
                755                 760                 765

Asn Phe Asn Gln Ser Gly Asn Ile Ala Asp Ser Ser Leu Ser Phe Thr
                770                 775                 780

Phe Thr Asn Ser Ser Asn Gly Pro Asn Leu Ile Thr Thr Gln Thr Asn
785                 790                 795                 800

Ser Gln Ala Leu Ser Gln Pro Ile Ala Ser Asn Val His Asp Asn
                805                 810                 815

Phe Met Asn Asn Glu Ile Thr Ala Ser Lys Ile Asp Asp Gly Asn Asn
                820                 825                 830

Ser Lys Pro Leu Ser Pro Gly Trp Thr Asp Gln Thr Ala Tyr Asn Ala
                835                 840                 845

Phe Gly Ile Thr Thr Gly Met Phe Asn Thr Thr Met Asp Asp Val
850                 855                 860

Tyr Asn Tyr Leu Phe Asp Asp Glu Asp Thr Pro Pro Asn Pro Lys Lys
865                 870                 875                 880
Glu

<210> SEQ ID NO 33
<211> LENGTH: 994
<212> TYPE: PRT
<213> ORGANISM: Artificial Sequence
<220> FEATURE:
<223> OTHER INFORMATION: consensus

<400> SEQUENCE: 33

Met His His Lys Glu Arg Leu Ile Asp His Ile Ser Ser Glu Ser Asn
1               5                   10                  15

Phe Ser Leu Ser Thr Ser Ser Met Pro Ser Phe Ser His Glu Ser Asn
                20                  25                  30

Gln Ser Pro Asn Pro Met Leu Ile Glu Gln Ala Cys Asp Ser Cys Arg
                35                  40                  45

Lys Arg Lys Leu Arg Cys Ser Lys Glu Tyr Pro Lys Cys Ser Lys Cys
                50                  55                  60

Val Thr His Lys Trp Ser Cys Val Tyr Ser Pro Arg Thr Val Arg Ser
65                  70                  75                  80

Pro Leu Thr Arg Ala His Leu Thr Lys Val Glu Asn Arg Val Arg Met
                85                  90                  95

Leu Glu Asp Leu Leu Glu Arg Val Phe Pro Thr Gln Ser Val Asp Gln
                100                 105                 110

Leu Leu Glu Lys Arg Thr Ser Leu Ser Gly Asn Ser Thr Gly His Ser
                115                 120                 125

Pro Ser Tyr Pro Asn Ser Asn Ser Val Ser Pro Gln Asn Ser Ser Pro
                130                 135                 140

Lys Val Ser Asp Ser Ser Ser Thr Thr Ala Glu Pro Ala Pro Val Leu
145                 150                 155                 160

Pro Ser Lys Pro Lys Ser Ser Phe Arg Pro Ile Val Pro Asp Asp Tyr
                165                 170                 175

Phe Leu Asn Asp Glu Ile Asn Gly Phe Asp Trp Glu Glu Glu Asp Thr
                180                 185                 190
```

```
Pro Asp Gln Leu Leu Val Met Gln Pro Pro Thr Ser Val Asp Ser
        195                 200                 205

Thr Asn Val Ser His Ser Tyr Trp Asn His Ser Arg Arg Ser Gln Lys
    210                 215                 220

Asn Ser Val Thr Ser Leu Asn Ser Leu Ala Glu His Glu Gln Ser Gly
225                 230                 235                 240

Cys Ser Ser Leu Ile Thr Ser Pro Ser Leu Gln Pro Leu Ser Gln Thr
                245                 250                 255

Thr Thr Asn Asp Ser His Pro Asp Gly Met Ala Ala Leu Ser Val Asn
            260                 265                 270

Leu Lys Gly Gly Ser Gly Tyr Phe Gly Phe Ser Ser Ser Gly Leu
            275                 280                 285

Leu Arg Ala Leu Lys Leu Gly Gln Phe Asp Ser Ala Ser Ile Ser Pro
        290                 295                 300

Met Ser Ser Val Arg Asn Ser Val Ser Lys Thr Asn Thr Glu Pro Thr
305                 310                 315                 320

Glu Pro Gln Ser Ile Arg Ser Leu Leu Gly Asp Pro Asn Asp Phe Leu
                325                 330                 335

Glu Pro Glu Lys Lys Ala Glu Phe Pro Gly Tyr Asp Ser His Leu Asn
            340                 345                 350

Asp Pro Asn Asn Gln Ser Gln Tyr Leu Gln Ala Tyr Phe Lys Tyr Tyr
        355                 360                 365

His Thr Ser Tyr Pro Phe Ile His Lys Gly Ser Phe Leu Lys His Tyr
    370                 375                 380

Ala Gly Glu Leu Pro Ile Lys Asn Glu Asn His Trp Gln Ile Leu Leu
385                 390                 395                 400

Asn Val Val Leu Ala Leu Gly Cys Trp Cys Leu Asn Gly Glu Ser Ser
                405                 410                 415

Ser Ile Asp Leu Cys Tyr Tyr Asn Arg Ala Lys Met Leu Leu Lys Gln
            420                 425                 430

Val Gly Ile Phe Glu Cys Gly Asn Ile Met Leu Leu Glu Ser Leu Ile
        435                 440                 445

Leu Leu Ser Asn Tyr Thr Gln Lys Arg Asn Lys Pro Asn Thr Gly Trp
    450                 455                 460

Ser Tyr Leu Gly Ile Ala Ile Arg Met Ala Met Ser Leu Gly Leu Tyr
465                 470                 475                 480

Lys Glu Phe Asn Leu Asp His Thr Glu Lys Asp His Tyr Leu Asn Leu
                485                 490                 495

Glu Ile Arg Arg Arg Leu Trp Trp Gly Leu Tyr Ile Phe Asp Ala Gly
            500                 505                 510

Ala Ser Ile Thr Phe Gly Arg Pro Ile Thr Leu Pro Ser Arg Asp Ser
        515                 520                 525

Cys Asp Ile Gln Leu Cys Ser Asn Ile Asn Asp Ala Glu Leu Glu Glu
    530                 535                 540

Leu Ile Glu Ile Lys Ser Asp Ser Ile Thr Thr Glu Asp Leu Asn Lys
545                 550                 555                 560

Pro Tyr Pro Thr Ala Tyr Ser Gly Leu Ile Gln Gln Thr Gln Phe Thr
                565                 570                 575

Glu Leu Ser Met Lys Ile Tyr Asn Arg Leu Val Ser Lys Pro Ala Pro
            580                 585                 590

Thr Val Glu Glu Cys Leu Asp Met Asn Met Glu Ile Glu Asn Phe Ile
        595                 600                 605
```

```
Lys Gly Leu Pro Ala Tyr Phe His Glu Ser Asn Glu Ile Ala Met Ser
            610                 615                 620

Gln Phe Tyr Lys Val Thr Pro Ser Lys Tyr Tyr Asp Tyr Asp Ser Asn
625                 630                 635                 640

Lys Gln Val Asp Tyr Thr Arg Leu Pro Gln Trp Phe Asp Leu Ser Arg
                645                 650                 655

Ser Arg Leu Ile Trp Arg Tyr Lys Asn Leu Gln Ile Thr Leu Phe Arg
                660                 665                 670

Ala Phe Ile Trp Gln Arg Val Ile Gly Val Thr Asn Pro Lys Val Leu
            675                 680                 685

Gln Gln Cys Lys Thr Ser Arg Gly Lys Glu Cys Arg Thr Ile Cys Leu
            690                 695                 700

Arg Val Ala His Glu Thr Ile Leu Ser Ile Gln Gln Phe Val Asn Ile
705                 710                 715                 720

Asp Asp Asp Asp Asp Phe Ser Arg Leu Ser Val Ile Gly Cys Trp Tyr
                725                 730                 735

Ala Thr Tyr Phe Leu Phe Gln Ala Val Leu Ile Pro Ile Ala Cys Leu
            740                 745                 750

Cys Ser Glu Pro Asp Ser Lys Tyr Ala Pro Ile Trp Ile Glu Asp Ile
            755                 760                 765

Gln Ile Ser Lys Lys Ile Phe Leu Lys Leu Asn Lys Leu Asn Ser Leu
            770                 775                 780

Ala Ser Lys Phe Ala Asn Val Ile Asp Arg Ser Met Ser Gln Val Met
785                 790                 795                 800

Pro Gln Phe Thr Thr Ser Ala Lys Asp Ser Pro Leu Asn Ile Asn Asp
                805                 810                 815

Leu Ile Asp Met His Gly Leu Met Gly Asn Ser Pro Ala Pro Gly Ser
                820                 825                 830

Asn Asn Asn Ser Asn Thr Lys Ser Ser Pro Ser Thr Thr Asn Asn Thr
            835                 840                 845

Arg Thr Pro Asn Thr Ile Asn Lys Asn Ser Asn Met Asn Asn Asn
            850                 855                 860

Ser Ile Asn Asn Tyr Phe Asn Asn Asn Ser Asn Asn Asn Asn Ser Phe
865                 870                 875                 880

Ser Ser Ser Lys Ala Gly Pro Val Lys Gln Phe Glu Asp Tyr Cys
                885                 890                 895

Leu Lys Leu Asp Pro Glu Asp Glu Asp Met Ser Ala Leu Glu Phe Thr
            900                 905                 910

Ala Val Arg Phe Pro Asn Phe Ser Ala Thr Thr Ala Pro Pro Pro
            915                 920                 925

Thr Pro Val Asn Cys Asn Ser Pro Glu Asn Ile Lys Thr Ser Thr Val
            930                 935                 940

Asp Asp Phe Leu Lys Ala Thr Gln Asp Pro Asn Asn Lys Glu Ile Leu
945                 950                 955                 960

Asn Asp Ile Tyr Ser Leu Ile Phe Asp Ser Met Asp Pro Met Ser
                965                 970                 975

Phe Gly Ser Met Glu Pro Arg Asn Asp Leu Glu Val Pro Asp Thr Ile
                980                 985                 990

Met Asp
```